United States Patent
Sher et al.

(10) Patent No.: US 9,254,297 B2
(45) Date of Patent: Feb. 9, 2016

(54) FORMULATIONS AND DOSAGE FORMS OF OXIDIZED PHOSPHOLIPIDS

(71) Applicant: Vascular Biogenics Ltd., Or Yehuda (IL)

(72) Inventors: Naamit Sher, Rohovot (IL); Victor M. Young, Midlothian (GB); Alyn McNaughton, West Lothian (GB); Massoud Bakhshaee, Glasgow (GB); Ian Robert Wilding, Beeston (GB)

(73) Assignee: Vascular Biogenics Ltd., Or Yehuda (IL)

( * ) Notice: Subject to any disclaimer, the term of this patent is extended or adjusted under 35 U.S.C. 154(b) by 11 days.

(21) Appl. No.: 13/792,633

(22) Filed: Mar. 11, 2013

(65) Prior Publication Data

US 2013/0209555 A1 Aug. 15, 2013

Related U.S. Application Data

(63) Continuation of application No. PCT/US2012/053533, filed on Aug. 31, 2012.

(60) Provisional application No. 61/529,989, filed on Sep. 1, 2011.

(51) Int. Cl.
*A61K 31/661* (2006.01)
*A61K 9/48* (2006.01)
(Continued)

(52) U.S. Cl.
CPC .............. *A61K 31/661* (2013.01); *A61K 9/485* (2013.01); *A61K 9/4808* (2013.01);
(Continued)

(58) Field of Classification Search
CPC . A61K 31/661; A61K 31/685; A61K 9/4808; A61K 9/485; A61K 9/4858
USPC ............. 424/456, 451; 514/114, 78; 558/169; 554/79
See application file for complete search history.

(56) References Cited

U.S. PATENT DOCUMENTS 4,450,877 A 5/1984 Walker et al.
4,970,233 A * 11/1990 McHugh ........................ 514/470
(Continued)

FOREIGN PATENT DOCUMENTS

WO WO 02/41827 A2 5/2002
WO WO 2004/106486 A2 12/2004
(Continued)

OTHER PUBLICATIONS

Aeroperl: retrieved from internet: https://www.aerosil.com/product/aerosil/en/products/granulated-products/pages/default.aspx. retrieved on Oct. 21, 2014.*
(Continued)

*Primary Examiner* — Ernst V Arnold
*Assistant Examiner* — Hong Yu
(74) *Attorney, Agent, or Firm* — Sterne, Kessler, Goldstein & Fox P.L.L.C.

(57) ABSTRACT

The current disclosure provides pharmaceutical compositions containing an oxidized phospholipid, such as 1-hexadecyl-2-(4'-carboxybutyl)-glycero-3-phosphocholine (VB-201) and a thermosoftening carrier, e.g., a poloxamer. The pharmaceutical compositions may further comprise an anti-adherent agent, such as talc and/or a thixotropic agent. The current disclosure further provides processes for preparing the pharmaceutical compositions. The disclosure further provides capsules containing the pharmaceutical compositions. Uses of such pharmaceutical compositions and capsules in treating inflammatory disorders are also disclosed.

37 Claims, 10 Drawing Sheets

(51) Int. Cl.
*A61K 31/685* (2006.01)
*C07F 9/02* (2006.01)

(52) U.S. Cl.
CPC ............ *A61K 9/4858* (2013.01); *A61K 9/4866* (2013.01); *A61K 9/4875* (2013.01); *A61K 9/4891* (2013.01); *A61K 31/685* (2013.01)

(56) References Cited

U.S. PATENT DOCUMENTS

| | | |
|---|---|---|
| 6,838,452 B2 | 1/2005 | Harats et al. |
| 7,186,704 B2 | 3/2007 | Harats et al. |
| 7,504,388 B2 | 3/2009 | Harats et al. |
| 7,625,882 B2 | 12/2009 | Harats et al. |
| 7,807,847 B2 | 10/2010 | Halperin et al. |
| 7,893,291 B2 | 2/2011 | Harats et al. |
| 7,902,176 B2 | 3/2011 | Harats et al. |
| 7,973,023 B2 | 7/2011 | Harats et al. |
| 8,124,800 B2 | 2/2012 | Halperin et al. |
| 8,158,611 B2 | 4/2012 | Harats et al. |
| 2003/0225035 A1* | 12/2003 | Harats et al. ............... 514/78 |
| 2006/0068015 A1* | 3/2006 | Holm et al. ............... 424/489 |
| 2011/0189212 A1 | 8/2011 | Harats et al. |
| 2011/0195937 A1 | 8/2011 | Breitbar et al. |
| 2011/0207703 A1 | 8/2011 | Kovalevski-Ishai et al. |
| 2012/0130108 A1 | 5/2012 | Halperin et al. |
| 2012/0329757 A1 | 12/2012 | Harats et al. |
| 2012/0329758 A1 | 12/2012 | Cohen et al. |
| 2013/0079540 A1 | 3/2013 | Halperin et al. |
| 2013/0158283 A1 | 6/2013 | Halperin et al. |
| 2013/0172294 A1 | 7/2013 | Cohen et al. |
| 2013/0190523 A1 | 7/2013 | Halperin et al. |
| 2013/0203707 A1 | 8/2013 | Kovalevski-Ishai et al. |
| 2013/0225525 A1 | 8/2013 | Cohen et al. |

FOREIGN PATENT DOCUMENTS

| | | |
|---|---|---|
| WO | WO 2006/006161 A2 | 1/2006 |
| WO | WO 2008/084472 A2 | 7/2008 |
| WO | WO 2010/041242 A2 | 4/2010 |
| WO | WO 2010/052718 A1 | 5/2010 |
| WO | WO 2011/083465 A1 | 7/2011 |
| WO | WO 2011/083467 A1 | 7/2011 |
| WO | WO 2011/083469 A1 | 7/2011 |
| WO | WO 2013/033642 A1 | 3/2013 |

OTHER PUBLICATIONS

Lombardin, P., et al., "Study of thixotropic bases for the filling of hard capsules," *S.T.P. Pharma Sciences* 10(6):429-437, Editions de Saṅe, France (2000).

International Search Report and Written Opinion for International Patent Application No. PCT/US2012/053533, European Patent Office, Netherlands, mailed Nov. 20, 2012.

Co-pending U.S. Appl. No. 13/833,940, filed Mar. 15, 2013, inventors Halperin, G. and Kovalevski-Ishai, E.

* cited by examiner

FORMULATIONS AND DOSAGE FORMS OF OXIDIZED PHOSPHOLIPIDS

FIELD AND BACKGROUND OF THE INVENTION

The present invention, relates to the field of pharmacology and more particularly, but not exclusively, to novel oral dosage forms of oxidized phospholipids.

Oxidized phospholipids have been previously described as useful in the treatment of medical conditions such as, for example, cardiovascular diseases, cerebrovascular diseases and inflammatory diseases and disorders.

International Patent Application No. PCT/IL2004/000453 (Publication No. WO 04/106486), by the present assignee, describes oxidized lipids for prevention and treatment of inflammation associated with endogenous oxidized lipids. An exemplary such compound is described and known as CI-201 (1-hexadecyl-2-(4'-carboxybutyl)-glycero-3-phosphocholine), also referred to in the art as VB-201. VB-201 was found to be an orally active drug, useful in the treatment of inflammatory disorders such as atherosclerosis, psoriasis, multiple sclerosis, rheumatoid arthritis and inflammatory bowel disease.

International Patent Application No. PCT/IL01/01080 (Publication No. WO 02/41827), by the present assignee, describes oxidized lipids for prevention and treatment of atherosclerosis and related diseases.

Additional background art includes International Patent Application Nos. PCT/IL05/000735 (Publication No. WO 06/006161), PCT/IL02/00005 (Publication No. WO 02/053092) and PCT/IL08/000,013 (Publication No. WO 08/084,472), all being also by the present assignee.

All of the above cited publications are incorporated by reference as if fully set forth herein.

Recently, and in view of the promising therapeutic effect of VB-201, clinical studies were conducted in order to evaluate the toxicity, efficacy and pharmacokinetic parameters of orally administered VB-201. The obtained results showed that daily dosages of 80 mg VB-201 per day or less are safe, well-tolerated, and effective at inhibiting inflammatory processes, that a substantial percentage of VB-201 is absorbed into the bloodstream, and that plasma concentrations of VB-201 are relatively stable when VB-201 is administered once per day, and are described in International Patent Application PCT/IL2011/000008, filed Jan. 5, 2011, which is incorporated by reference as if fully set forth herein.

In view of the potential therapeutic effects of oxidized phospholipids (e.g., VB-201), a need arises for industrially and pharmaceutically applicable formulations containing oxidized phospholipids, such as VB-201, as the active ingredient.

SUMMARY OF THE INVENTION

The present disclosure provides pharmaceutical compositions comprising an oxidized phospholipid (e.g., VB-201, VB-208, VB-221, or VB-219) having a structure as described herein (see, e.g., Formulae (I), (II), and (III)) and a thermosoftening carrier. These compositions are useful as liquid fill compositions, which can be placed into pharmaceutical receptacles, such as capsules (e.g., hard-shell gelatin capsules). The inventors have discovered that certain oxidized phospholipids of the present disclosure tend to be adherent (i.e., sticky) and optionally hygroscopic. These physical properties may arise from undergoing a phase transition at relatively low temperature (e.g., at about 25-30° C.). As a result, these oxidized phospholipids are difficult to formulate into traditional dosage forms, such as tablets or capsules filled with liquid compositions. An exemplary oxidized phospholipid is 1-hexadecyl-2-(4'-carboxybutyl)-glycero-3-phosphocholine (VB-201).

Capsules constitute one of the principal dosage forms for pharmaceutical and health food products. The process of producing liquid-fill capsules is typically associated with various difficulties. For example, in capsule fill compositions which can be used in conjunction with soft capsules, the active ingredient needs to be in the solubilized state in a solvent mixture. Obtaining an appropriate solution of the pharmaceutically active substance may be challenging. Often it is not possible to dissolve the pharmaceutically active substance in a volume of solvent small enough to produce a capsule of appropriate size from the standpoint of economics and patient acceptance. Furthermore, the solvent, carrier or vehicle itself must have sufficient solvating power to dissolve the desired amount of the pharmaceutically active substance to produce a reasonably concentrated solution, while at the same time not hydrolyzing, dissolving or discoloring the capsule shell. Furthermore, the fill composition as a whole must be chemically compatible with the capsule material and avoid degradation of the material once it has been encapsulated, as well as be inert or reduce adverse chemical interaction with the active ingredient. The biological activity of the active ingredient must not be significantly compromised. Accordingly, developmental challenges can arise in balancing all of these characteristics while accounting for the chemical nature of the active ingredient.

The inventors have discovered that capsules containing oxidized phospholipids in a liquid carrier are not sufficiently stable (e.g., leakage and cracking occurred).

Liquid-fill hard capsule technology was contemplated to overcome the substantial challenges associated with producing a commercially viable oxidized phospholipid (e.g., VB-201, VB-208, VB-221, or VB-219) formulation. Hard capsules are typically made from gelatin, hydroxypropylmethyl cellulose (HPMC) or other suitable material and are filled on purpose-built high speed filling machines. The capsules may be filled with materials such as powders, granules, pellets, other capsules, liquids, semi-solids or thermosetting materials.

It was discovered that liquid-fill hard capsule technology is suitable for the formulation of oxidized phospholipids. Experiments were conducted to formulate the oxidized phospholipids into a liquid-fill composition, which contains a thermosoftening carrier. For example, at higher temperature, e.g., above 60° C., the pharmaceutical composition is sufficiently liquid (flowable) for filling the composition into pharmaceutical receptacles, such as capsules. Upon cooling, the composition solidifies sufficiently to preserve homogeneity and prevent leakage and cracking of the receptacle (e.g., capsule). Upon cooling the solidified fill-composition forms a solid or semi-solid matrix of the capsule.

Surprisingly, the inventors have further uncovered that the homogeneity of the pharmaceutical composition, the fill-composition, and consequently batches of capsules containing the oxidized phospholipid (e.g., VB-201, VB-208, VB-221, or VB-219) can be considerably improved by mixing the oxidized phospholipid (e.g., VB-201, VB-208, VB-221, or VB-219) with an anti-adherent agent, e.g., prior to contacting the oxidized phospholipid with the molten thermosoftening carrier. For example, it is surprising that the use of an anti-adherent agent with little or no solubility (e.g., in the molten thermosoftening carrier) increases homogeneity of the final formulation because typically, such addition would be expected to decrease homogeneity of a liquid-fill composition (e.g., by sedimentation and/or coagulation).

Hence, in some embodiments, the above pharmaceutical compositions further comprise an anti-adherent agent. For example, homogeneity of the pharmaceutical composition can be further increased by grinding or milling the oxidized phospholipid (e.g., VB-201, VB-208, VB-221, or VB-219) with the anti-adherent agent, e.g., to form a powder blend. In some embodiments, the oxidized phospholipid (e.g., VB-201, VB-208, VB-221, or VB-219) is mixed (e.g., milled together with) the anti-adherent agent prior to contacting the oxidized phospholipid with the thermosoftening carrier. For example, milling the oxidized phospholipid with an anti-adherent agent increases the homogeneity of the solidified pharmaceutical composition with respect to the spatial distribution of the oxidized phospholipid in the final composition.

The inventors have further discovered that the addition of a thixotropic agent to the pharmaceutical composition (i.e., liquid-fill composition) further increases the above described homogeneity of the final formulation. Thus, in some examples according to any of the above embodiments, the pharmaceutical composition further comprises a thixotropic agent or a gelling agent. For example, adding the thixotropic agent or the gelling agent to the pharmaceutical composition increases the viscosity of the composition and further increases the homogeneity of the pharmaceutical composition, e.g., by preventing separation of ingredients before the composition solidifies upon cooling. Thixotropic agents are particularly useful in the pharmaceutical compositions of the present disclosure, e.g., because they can cause the composition to become "gel-like" when stirring ceases and the composition is allowed to stand prior to filling and final cooling. Thixotropic agents may also allow for a more rapid solidification of the composition once the composition has been filled into the capsule thereby improving homogeneity.

According to some embodiments of the present invention there is provided a liquid-fill capsule comprising an oxidized phospholipid (e.g., VB-201, VB-208, VB-221, or VB-219) and a solid or semi-solid matrix, the matrix comprising a thermosoftening carrier. According to other embodiments of the present invention there is provided a liquid-fill capsule comprising an oxidized phospholipid (e.g., VB-201, VB-208, VB-221, or VB-219) and a solid or semi-solid matrix, the matrix comprising a thermosoftening carrier and an anti-adherent agent. According to other embodiments of the present invention there is provided a liquid-fill capsule comprising an oxidized phospholipid (e.g., VB-201, VB-208, VB-221, or VB-219) and a solid or semi-solid matrix, the matrix comprising a thermosoftening carrier, an anti-adherent agent, and a thixotropic agent.

According to some embodiments of the invention, the capsule comprises a shell material selected from the group consisting of gelatin, pullulan, starch, and hydroxypropyl methyl cellulose (HPMC).

According to some embodiments of the invention, the shell material comprises gelatin.

According to some embodiments of the present invention there is provided a liquid-fill capsule comprising 1-hexadecyl-2-(4'-carboxybutyl)-glycero-3-phosphocholine (VB-201) and a solid or semi-solid matrix, the matrix comprising a thermosoftening carrier.

According to some embodiments of the invention, the thermosoftening carrier has a melting point in a range from about 40° C. to about 100° C.

According to some embodiments of the invention, the thermosoftening carrier is selected from the group consisting of a polyalkylene glycol, a polyalkylene glycol derivative, and a wax. An oil may be added to the thermosoftening carrier.

According to some embodiments of the invention, the polyalkylene glycol is selected from the group consisting of a polyethylene glycol, a polypropylene glycol, and copolymers thereof.

According to some embodiments of the invention, the thermosoftening carrier is a poloxamer.

According to some embodiments of the invention, the poloxamer has a molecular weight in a range of from about 2000 to about 18000 daltons.

According to some embodiments of the invention, the poloxamer has a molecular weight in a range of from about 7000 to about 10000 daltons.

According to some embodiments of the invention, the poloxamer comprises from about 40 to about 90 weight percent polyethylene glycol.

According to some embodiments of the invention, the poloxamer is poloxamer 188.

According to some embodiments of the invention, the thermosoftening carrier is a polyethylene glycol.

According to some embodiments of the invention, the polyethylene glycol has a molecular weight in a range of about 1500 to about 8000 daltons.

According to some embodiments of the invention, the polyethylene glycol has a molecular weight of about 6000.

According to some embodiments of the invention, the anti-adherent agent is talc.

According to some embodiments of the invention, a ratio of an amount of the anti-adherent agent to an amount of the VB-201 is in a range of from about 1:5 to 5:1 (e.g., from about 1:4 to 5:1, from about 1:4 to about 1:1, or from about 1:3 to about 5:1).

According to some embodiments of the invention, a concentration of the anti-adherent agent in the pharmaceutical composition or matrix is in a range of from about 1 to about 30 weight percent.

According to some embodiments of the invention, the pharmaceutical composition or matrix of the capsule further comprises a thixotropic agent and/or a gelling agent.

According to some embodiments of the invention, the pharmaceutical composition or matrix comprises a thixotropic agent.

According to some embodiments of the invention, the thixotropic agent is fumed silica.

According to some embodiments of the invention, the concentration of the thixotropic agent in the pharmaceutical composition or matrix is in a range of from about 0.25 weight percent to about 10 weight percent.

According to some embodiments of the invention, the capsule comprises from about 1 mg to about 100 mg VB-201.

According to some embodiments of the invention, the capsule comprises from about 20 mg to about 80 mg VB-201.

According to some embodiments of the invention, the capsule comprises 20 mg VB-201.

According to some embodiments of the invention, the capsule comprises 40 mg VB-201.

According to some embodiments of the invention, the capsule comprises 80 mg VB-201.

According to some embodiments of the invention, the capsule is a size 0 capsule.

The present disclosure further provides a process for producing a pharmaceutical composition comprising an oxidized phospholipid (e.g., VB-201, VB-208, VB-221, or VB-219) and a thermosoftening carrier. The process comprises heating the thermosoftening carrier to a temperature above the melting point of the thermosoftening carrier, and contacting the oxidized phospholipid with the thermosoftening carrier, to thereby obtain the pharmaceutical composition. The process may further include contacting (e.g., mixing or milling) the oxidized phospholipid with an anti-adherent agent, e.g., prior to contacting the oxidized phospholipid with the thermosoftening carrier. The process may further include admixing the thermosoftening carrier with a thixotropic agent, e.g., prior to contacting the oxidized phospholipid with the thermosoftening carrier.

The present disclosure further provides a process for producing a liquid-fill capsule comprising 1-hexadecyl-2-(4'-carboxybutyl)-glycero-3-phosphocholine (VB-201), the process comprising filling a capsule shell with a liquid-fill composition which comprises VB-201 and a thermosoftening carrier, to thereby produce the capsule.

According to some embodiments of the present disclosure there is provided a process for producing a liquid fill composition which comprises VB-201, the process comprising mixing VB-201 with a thermosoftening carrier at a temperature above room temperature, to thereby obtain the liquid fill composition.

According to some embodiments of the present invention there is provided a liquid-fill capsule prepared by the above-mentioned process for producing a liquid-fill capsule.

According to some embodiments of the invention, the filling is performed at a temperature above room temperature, and the liquid composition forms a solid or semisolid matrix upon being cooled to room temperature.

According to some embodiments of the invention, the process further comprises mixing VB-201 with a carrier to thereby obtain the composition comprising VB-201.

According to some embodiments of the invention, the process further comprises mixing VB-201 with an anti-adherent agent prior to the mixing of VB-201 with the carrier.

According to some embodiments of the invention, the anti-adherent agent is mixed with the VB-201 in a ratio in a range of from about 1:5 to about 5:1 (e.g., from about 1:4 to about 1:1, or from about 1:3 to about 5:1).

According to some embodiments of the invention, a final concentration of the anti-adherent agent in the composition is in a range of from 1 to 30 weight percent.

According to some embodiments of the invention, the process further comprises admixing a thixotropic agent and/or a gelling agent with the carrier and the VB-201.

According to some embodiments of the invention, the process further comprises admixing a thixotropic agent with the carrier and the VB-201.

According to some embodiments of the invention, the process further comprises admixing with the liquid fill composition a thixotropic agent and/or a gelling agent.

According to some embodiments of the invention, the process further comprises admixing with the liquid fill composition a thixotropic agent.

According to some embodiments of the invention, the thixotropic agent is added such that a final concentration of the thixotropic agent in the composition is in a range of from 0.25 weight percent to 10 weight percent.

According to some embodiments of the invention, the carrier has a melting point in a range of from 40° C. to 100° C., and the mixing is performed above the melting point.

According to some embodiments of the invention, the capsule is for use in the treatment of an inflammatory disease or disorder.

According to some embodiments of the present disclosure there is provided a method of treating an inflammatory disease or disorder, the method comprising administering to a subject in need thereof a pharmaceutical composition or a capsule described herein.

According to some embodiments of the invention, the inflammatory disease or disorder is associated with an endogenous oxidized lipid.

According to some embodiments of the invention, the inflammatory disease or disorder is selected from the group consisting of an idiopathic inflammatory disease or disorder, a chronic inflammatory disease or disorder, an acute inflammatory disease or disorder, an autoimmune disease or disorder, an infectious disease or disorder, an inflammatory malignant disease or disorder, an inflammatory transplantation-related disease or disorder, an inflammatory degenerative disease or disorder, a disease or disorder associated with a hypersensitivity, an inflammatory cardiovascular disease or disorder, an inflammatory cerebrovascular disease or disorder, a peripheral vascular disease or disorder, an inflammatory glandular disease or disorder, an inflammatory gastrointestinal disease or disorder, an inflammatory cutaneous disease or disorder, an inflammatory hepatic disease or disorder, an inflammatory neurological disease or disorder, an inflammatory musculo-skeletal disease or disorder, an inflammatory renal disease or disorder, an inflammatory reproductive disease or disorder, an inflammatory systemic disease or disorder, an inflammatory connective tissue disease or disorder, an inflammatory tumor, necrosis, an inflammatory implant-related disease or disorder, an inflammatory aging process, an immunodeficiency disease or disorder, a proliferative disease or disorder and an inflammatory pulmonary disease or disorder.

According to some embodiments of the invention, the disease or disorder is selected from the group consisting of psoriasis, rheumatoid arthritis, multiple sclerosis, inflammatory bowel disease, atherosclerosis, and inflammation of an artery.

In other embodiments, the present disclosure provides a pharmaceutical formulation comprising VB-201, wherein the formulation, when orally administered to a human subject at a single oral dose of about 40 mg of VB-201, provides a mean maximum plasma concentration ($C_{max}$) of VB-201 from about 1,000 ng/mL to about 1,600 ng/mL, and a median time to mean maximum plasma concentration ($T_{max}$) of VB-201 from about 5 hours to about 10 hours.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 1A presents kinetic data showing both weight percentage uptake (Wt (% d.b.)) and relative humidity (RH (%)) as a function of time. FIG. 1B shows the equilibrium values for weight percentage uptake as a function of relative humidity, during sorption (Iso 01 Sorp) and desorption (Iso 01 Desorp);

DESCRIPTION OF SPECIFIC EMBODIMENTS OF THE INVENTION

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The present inventors have put ample efforts into identifying and overcoming many obstacles to formulation of oxidized phospholipids, such as VB-201, in a unit dosage form that is convenient for administration, can be produced readily at low cost, and is safe, long-lasting and reliable. The identification and solution of several obstacles is described in the Examples section.

VB-201 (also referred to herein and in the art as CI-201) has shown considerable promise as a therapeutically active agent in various in vitro models and in vivo animal models of inflammatory conditions. VB-201 is currently undergoing Phase II clinical trials for the treatment of various inflammatory conditions.

In an attempt to facilitate treatment with VB-201 and other oxidized phospholipids, the present inventors have devised suitable formulations and unit dosage forms for such compounds.

Figure 1A:
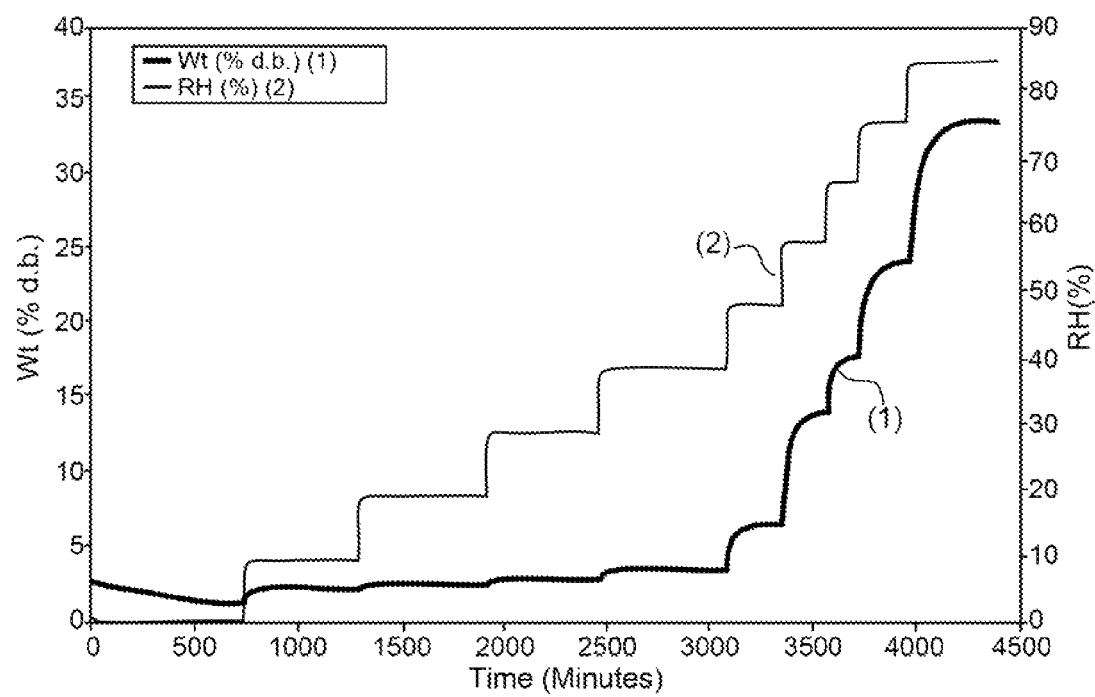
FIGS. 1A and 1B are graphs showing uptake of water by VB-201 at various relative humidities, as determined by gravimetric vapor sorption analysis.
Figure 1B:
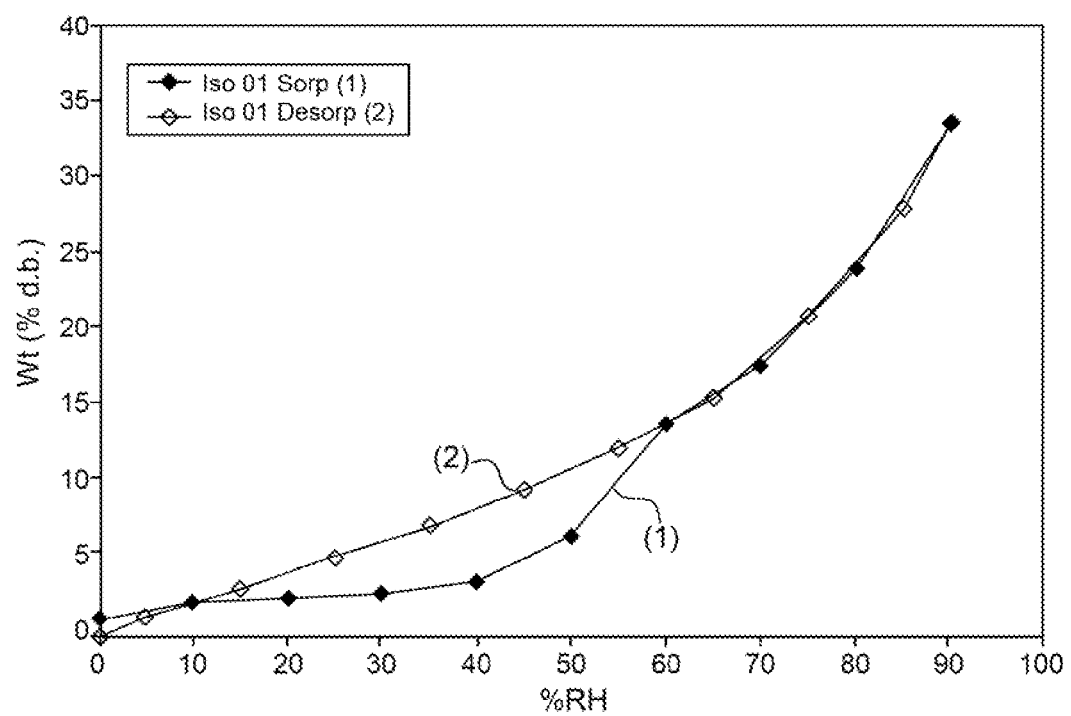

Referring now to the drawings, FIGS. 1A and 1B show that certain oxidized phospholipids, such as VB-201, are hygroscopic and absorb considerable amounts of water from the surroundings, especially at a relative humidity of 40% or higher.

Figure 2:
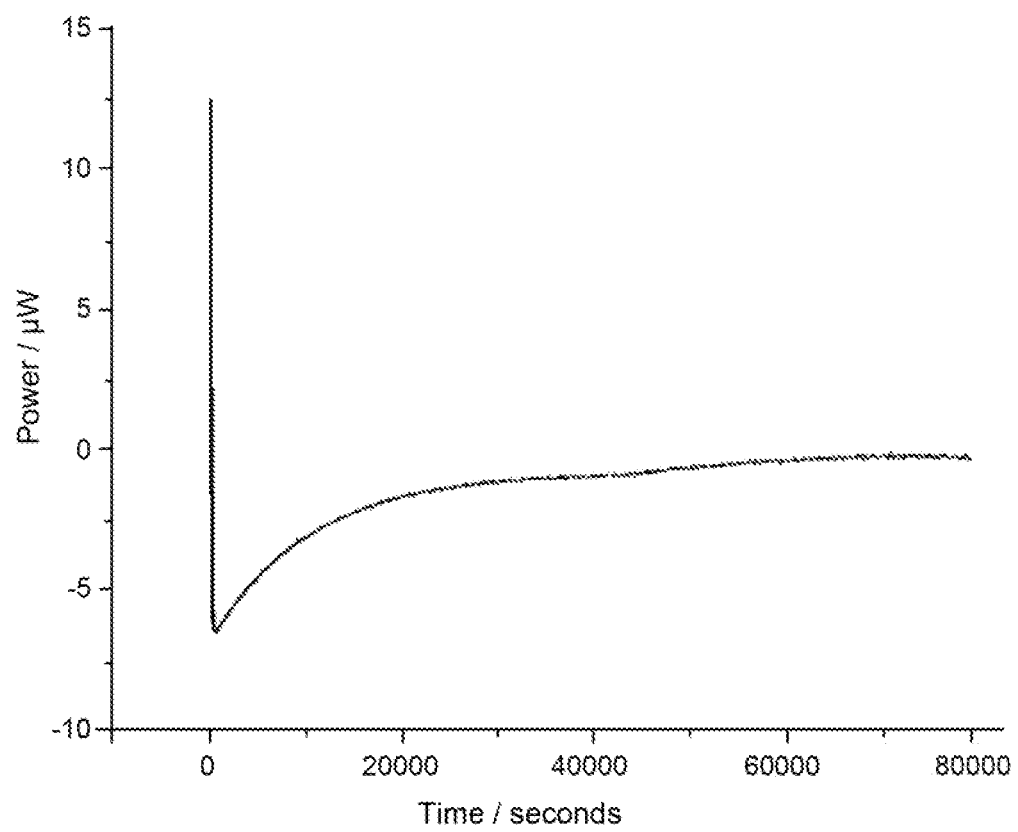
FIG. 2 is a graph showing the results of isothermal calorimetry of 88 mg VB-201.
Figure 3:
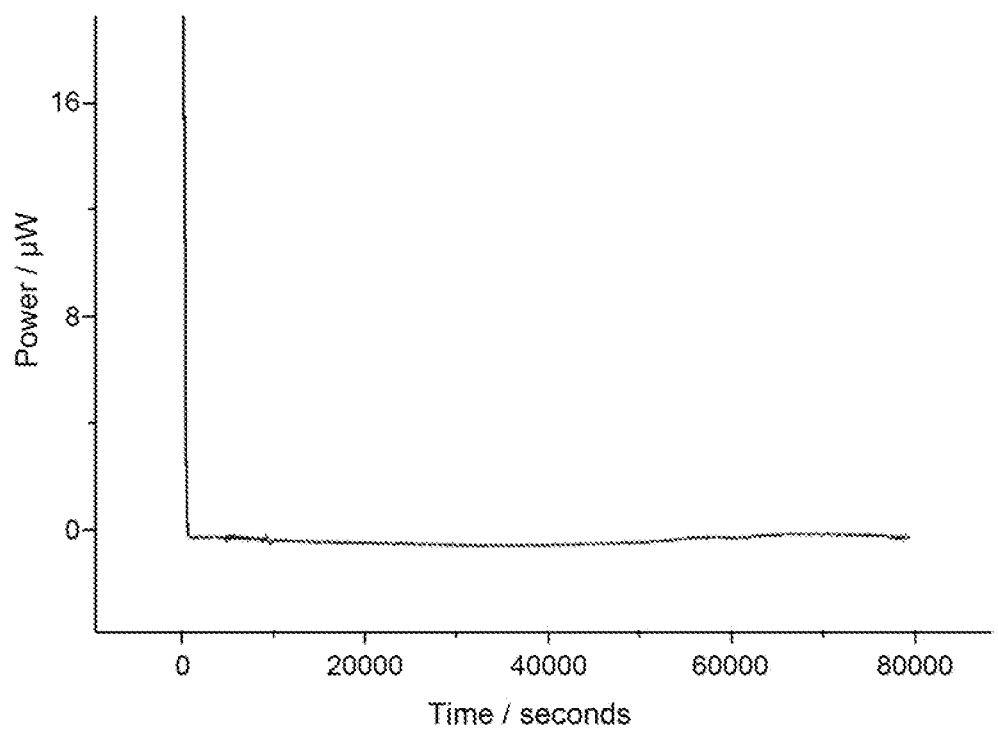
FIG. 3 is a graph showing the results of isothermal calorimetry of 262 mg Lauroglycol FCC.
Figure 4:
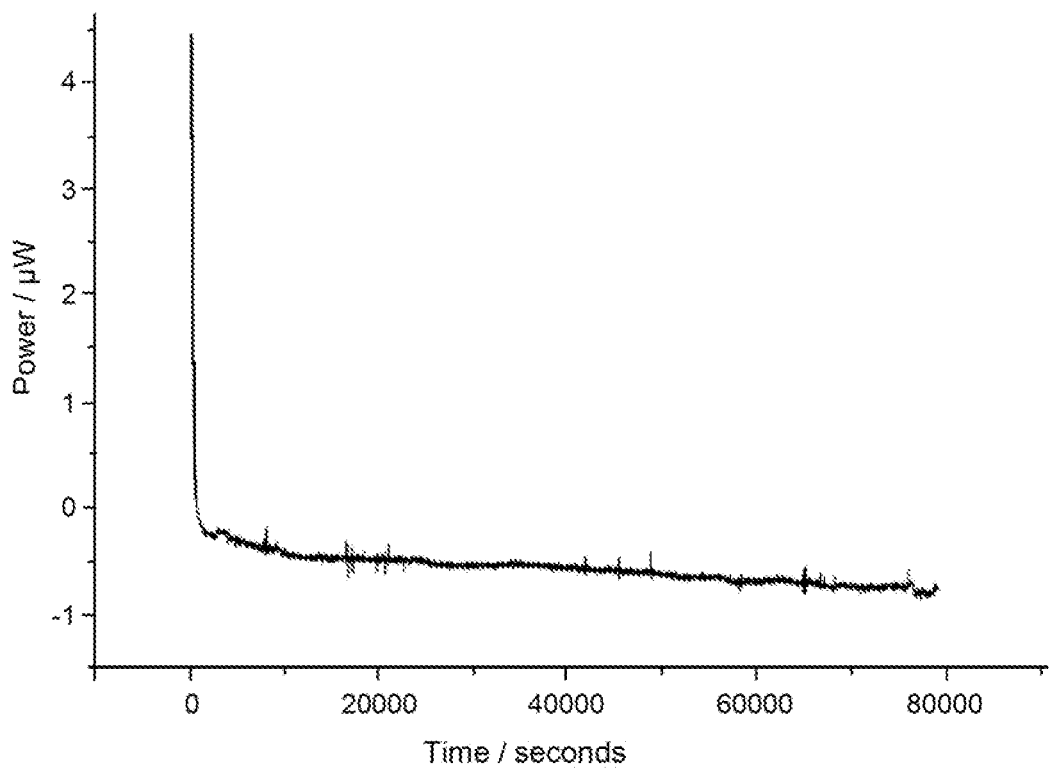
FIG. 4 is a graph showing the results of isothermal calorimetry of 88 mg VB-201 mixed with 262 mg Lauroglycol FCC, showing power as a function of time.

FIG. 2 shows isothermal calorimetry data which indicates that VB-201 undergoes a transition when exposed to the surrounding environment. FIGS. 3 and 4 show isothermal calorimetry data which indicates that Lauroglycol FCC (a non-polar solvent) does not undergo such a transition and is capable of preventing VB-201 dissolved therein from undergoing such a transition. FIGS. 2-4 confirm the abovementioned finding that VB-201 is hygroscopic, and suggest that absorption of water by VB-201 can be prevented by providing a non-aqueous environment.

Figure 5:
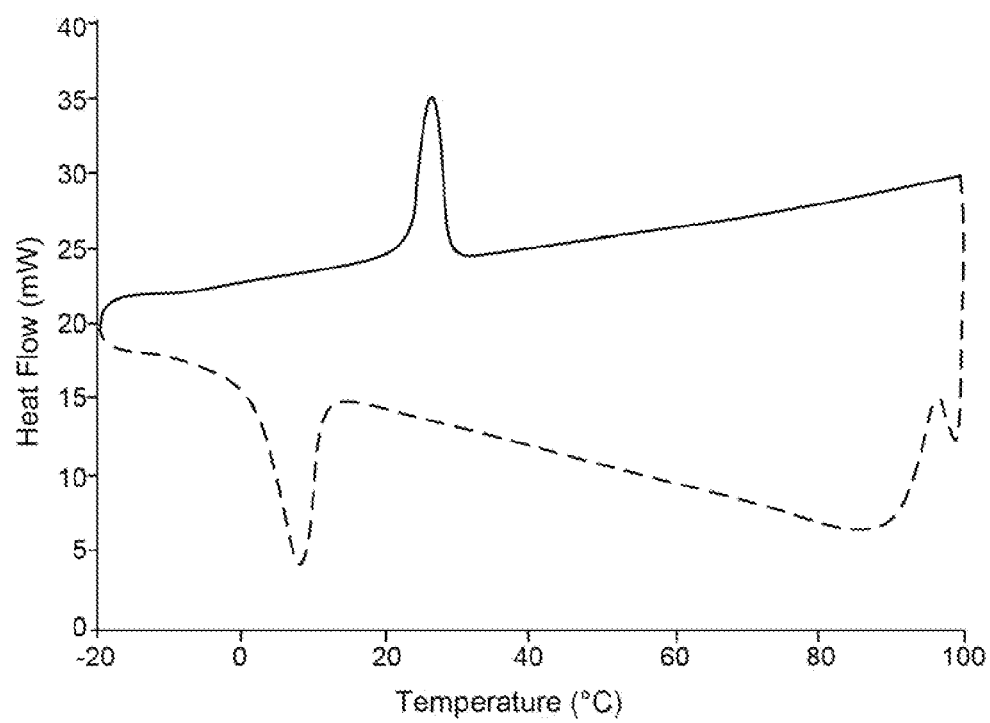
FIG. 5 is a differential scanning calorimetry thermograph obtained by heating (solid line) and then cooling (dotted line) VB-201 at a rate of 10° C. per minute.
Figure 6:
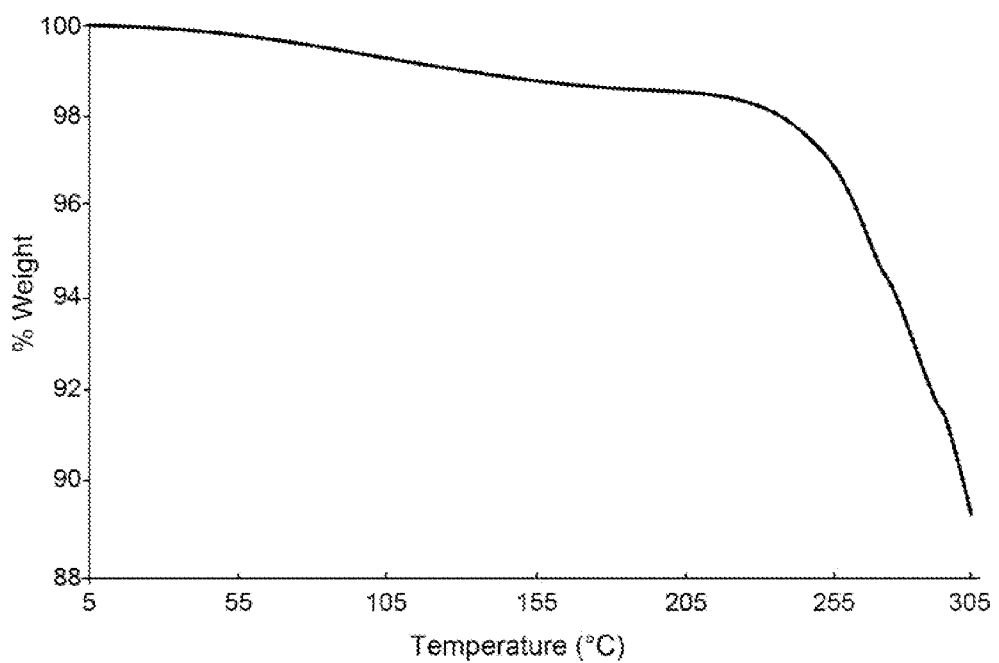
FIG. 6 is a graph showing the weight loss profile of VB-201 obtained upon heating VB-201 at a rate of 10° C. per minute.

FIG. 5 shows differential scanning calorimetry data which indicates that VB-201 undergoes a phase transition when heated to above about 25° C. FIG. 6 shows that the observed transition is not associated with removal of a volatile compound from the VB-201 sample.

Figure 7:
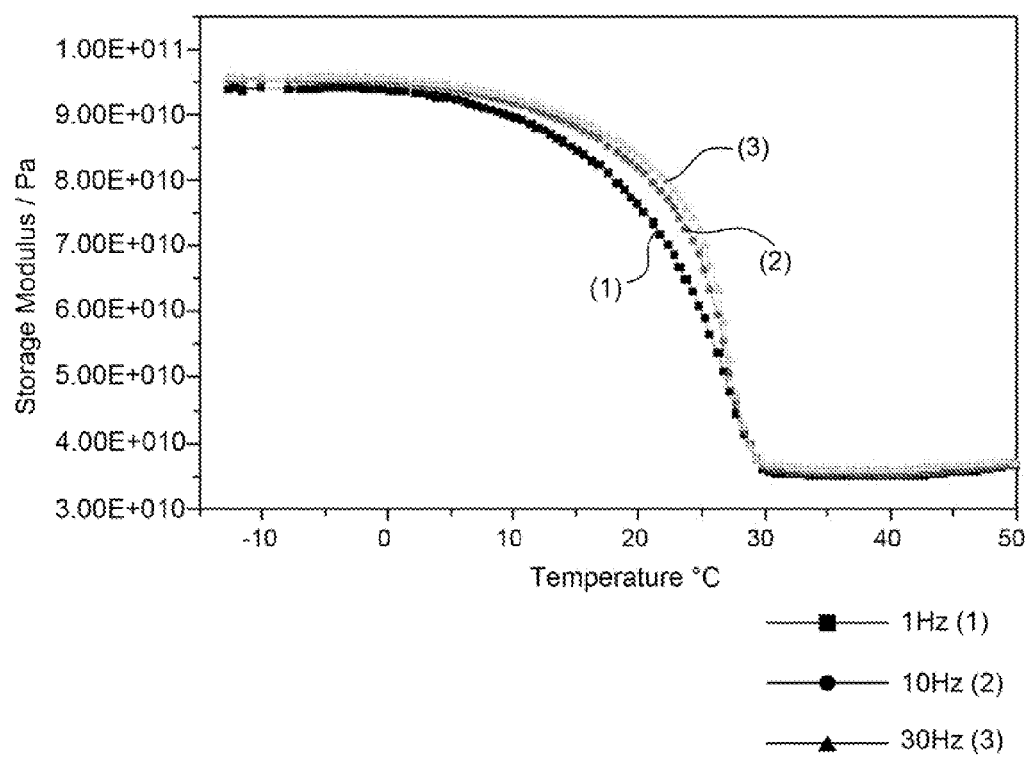
FIG. 7 is a graph showing the storage modulus of VB-201 as a function of temperature, using a maximum displacement of 0.05 mm at 1, 10 and 30 Hz, and a heating rate of 2° C. per minute.
Figure 8:
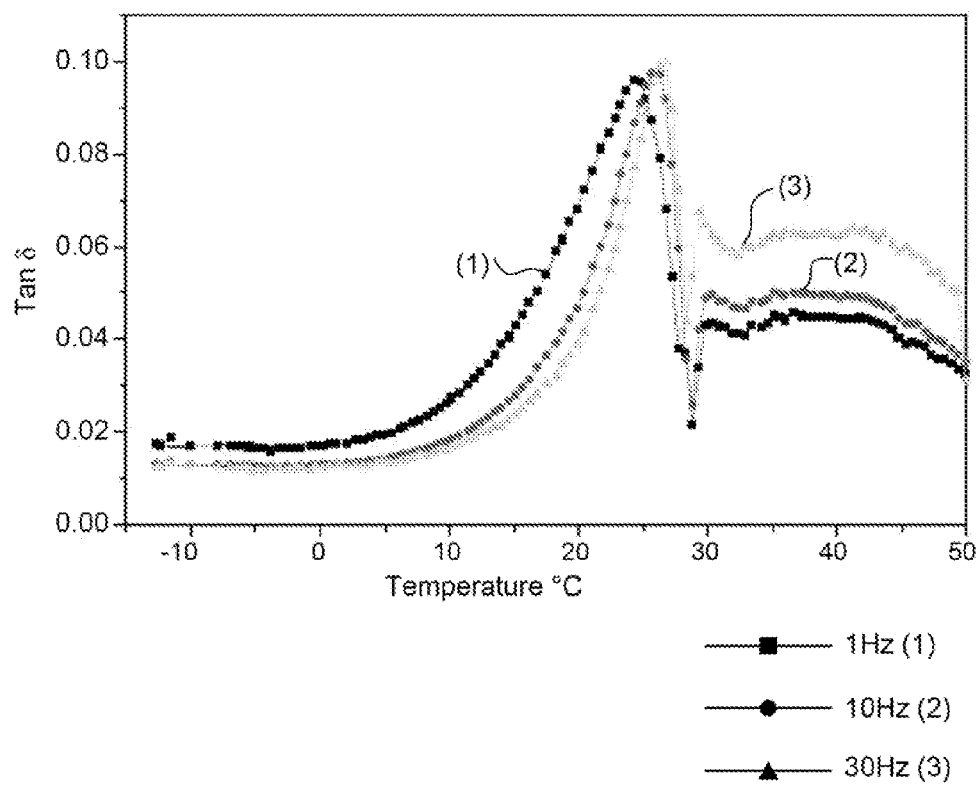
FIG. 8 is a graph showing the damping parameter (tan δ) of VB-201 as a function of temperature, using a maximum displacement of 0.05 mm at 1, 10 and 30 Hz; and a heating rate of 2° C. per minute.

FIG. 7 shows that the storage modulus of VB-201 decreases considerably when VB-201 is heated to about 30° C. FIG. 8 shows that the damping parameter (tan δ) of VB-201 peaks at about 25° C. when VB-201 is heated, and that the temperature at which the damping parameter peaks is dependent upon the frequency of oscillation.

FIGS. 5-8 indicate that VB-201 undergoes a phase transition at a temperature range of about 25-30° C. The data presented in FIGS. 7 and 8 suggest that the transition is a glass transition. These results confirm the visual observation that VB-201 becomes sticky and cohesive at 25-30° C.

Because certain oxidized phospholipids of the present disclosure (e.g., VB-201) are sticky and cohesive at room temperature, formulating these substances (e.g., VB-201) into conventional oral solid dosage forms (e.g. tablet or powder blend capsules) was not feasible, i.e., for large-scale production. Accordingly, studies were conducted for developing either liquid fill capsules of solubilized drug (which stays liquid) or liquid-fill capsules of molten carrier which becomes solid or semi-solid upon cooling.

As described in the experimental results presented in the Examples section below, an exemplary oxidized phospholipid, VB-201, was stable in a liquid carrier, but such formulation resulted in leakage and cracking of the capsule containing the VB-201 in the liquid carrier. The hygroscopic nature of VB-201 may be responsible for the instability of the liquid formulation filled capsule.

As further described herein, the aforementioned leakage and cracking was circumvented by encapsulating the oxidized phospholipid (e.g., VB-201) by liquid-filling with a molten carrier that solidifies at room temperature to form a solid matrix (thermosoftening carrier). However, the uniformity of VB-201 content in the capsules was not optimal.

Following considerable experimentation, the present inventors have uncovered that the stickiness and cohesiveness of certain oxidized phospholipids (e.g. VB-201) result in a decrease of capsule uniformity when the oxidized phospholipid (e.g., VB-201) is mixed with a molten carrier. The stickiness and cohesiveness of the oxidized phospholipid (e.g., VB-201) also make encapsulation of the oxidized phospholipid (e.g., VB-201) by solid-filling (e.g., using powdered VB-201) a less preferred method of encapsulation.

As further demonstrated in the Examples section, the present inventors have devised novel methodologies for overcoming the stickiness and cohesiveness of oxidized phospholipids (e.g., VB-201), thereby allowing for the production of oxidized phospholipid (e.g., VB-201) formulations characterized by a high uniformity. In some examples, the improved formulations are capsules having a solid or semi-solid matrix.

The matrix reduces water absorption by the oxidized phospholipid (e.g., VB-201), thereby preventing adverse effects of absorption, such as cracking and leakage.

Pharmaceutical Compositions

Hence, the current disclosure provides pharmaceutical compositions (e.g., liquid-fill compositions) comprising an oxidized phospholipid as the active pharmaceutical ingredient (e.g., VB-201, VB-208, VB-221, or VB-219) and a thermosoftening carrier as described herein. Oxidized phospholipids and thermosoftening carrier that are useful in the above pharmaceutical compositions are described herein. In one example, the pharmaceutical composition is suitable to be filled into a pharmaceutical receptacle, such as a capsule (e.g., a liquid-fill hard shell capsule); e.g., upon heating to produce a liquid composition.

In some embodiments, the disclosure provides pharmaceutical compositions (e.g., liquid-fill compositions) comprising an oxidized phospholipid as the active pharmaceutical ingredient (e.g., VB-201, VB-208, VB-221, or VB-219), a thermosoftening carrier as described herein, and an anti-adherent agent as described herein.

In other embodiments, the disclosure provides pharmaceutical compositions (e.g., liquid-fill compositions) comprising an oxidized phospholipid as the active pharmaceutical ingredient (e.g., VB-201, VB-208, VB-221, or VB-219), a thermosoftening carrier as described herein, an anti-adherent agent as described herein, and a thixotropic agent as described herein.

Thus, in some embodiments the present disclosure provides a pharmaceutical composition comprising VB-201 and a thermosoftening carrier. Exemplary thermosoftening carrier are disclosed herein.

In other embodiments the present disclosure provides a pharmaceutical composition comprising VB-201, a thermosoftening carrier, and an anti-adherent agent. Exemplary thermosoftening carrier and anti-adherent agents are described herein. Any combination of the disclosed thermosoftening carriers and anti-adherent agents is contemplated.

In other embodiments the present disclosure provides a pharmaceutical composition comprising VB-201, a thermosoftening carrier, an anti-adherent agent, and a thixotropic agent. Exemplary thermosoftening carrier, anti-adherent agents, and thixotropic agents are described herein. Any combination of the disclosed thermosoftening carriers, anti-adherent agents, and thixotropic agents is contemplated.

In some embodiments the current disclosure provides a pharmaceutical composition comprising:
a thermosoftening carrier;
a thixotropic agent at a concentration from about 0.25 weight percent to about 10 weight percent relative to the combined weight of the thermosoftening carrier and the thixotropic agent;
an oxidized phospholipid (e.g., VB-201, VB-208, VB-221, or VB-219), e.g., at a concentration from about 0.1 weight percent to about 25 weight percent relative to the total weight of the pharmaceutical composition; and
an anti-adherent agent at a weight ratio from about 1:5 to about 5:1 anti-adherent agent:oxidized phospholipid (e.g., VB-201, VB-208, VB-221, or VB-219).

In some embodiments the current disclosure provides a pharmaceutical composition comprising:
a thermosoftening carrier,
a thixotropic agent at a concentration from about 0.5 weight percent to about 5 weight percent (e.g., from about 1 weight percent to about 3 weight percent) relative to the combined weight of the thermosoftening carrier and the thixotropic agent;
an oxidized phospholipid (e.g., VB-201, VB-208, VB-221, or VB-219), e.g., at a concentration from about 4 weight percent to about 18 weight percent relative to the total weight of the pharmaceutical composition; and
an anti-adherent agent at a weight ratio from about 1:4 to about 2:1 anti-adherent agent:oxidized phospholipid (e.g., VB-201, VB-208, VB-221, or VB-219).

Liquid-Fill Capsules

In some embodiments, the present disclosure provides a formulation, e.g., a liquid-fill capsule, comprising a solid or semi-solid matrix, wherein the matrix comprises a thermosoftening carrier and an oxidized phospholipid as described herein. The liquid-fill capsule may further include an anti-adherent agent as described herein, and optionally a thixotropic agent as described herein.

According to some embodiments of the present disclosure there is provided a liquid-fill capsule comprising:
a thermosoftening carrier (e.g., poloxamer 188);
an oxidized phospholipid (e.g., VB-201) from about 1 mg to about 100 mg (e.g., from about 20 mg to about 80 mg);
an anti-adherent agent at a weight ratio from about 1:5 to 5:1 (anti-adherent agent:oxidized phospholipid (e.g., VB-201); and
a thixotropic agent (e.g., fumed silicon dioxide) at a concentration relative to the combined weight of the thermosoftening carrier and the thixotropic agent from about 0.25 weight percent to about 10 weight percent (e.g., 1 weight percent to about 3 weight percent).

According to other embodiments of the present disclosure there is provided a liquid-fill capsule comprising:
a thermosoftening carrier (e.g., poloxamer 188);
VB-201 from about 1 mg to about 100 mg (e.g., from about 20 mg to about 80 mg);
talc at a weight ratio from about 1:5 to 5:1 (talc:VB-201); and
a thixotropic agent (e.g., fumed silicon dioxide) at a concentration relative to the combined weight of said thermosoftening carrier and said thixotropic agent from about 0.5 weight percent to about 5 weight percent (e.g., from about 1 weight percent to about 3 weight percent).

According to some embodiments of the present disclosure there is provided a liquid-fill capsule comprising:
a thermosoftening carrier selected from a poloxamer (e.g., poloxamer 188) and a polyethylene glycol having a molecular weight from about 6000 to about 8000;
VB-201 from about 1 mg to about 100 mg (e.g., from about 20 mg to about 80 mg);
talc at a weight ratio from about 1:4 to about 1:1 (talc:VB-201); and
a thixotropic agent (e.g., fumed silicon dioxide) at a concentration relative to the combined weight of said thermosoftening carrier and said thixotropic agent from about 0.5 weight percent to about 5 weight percent (e.g., from about 1 weight percent to about 3 weight percent).

According to some embodiments of the present disclosure there is provided a liquid-fill capsule comprising:
a thermosoftening carrier selected from a poloxamer (e.g., poloxamer 188) and a polyethylene glycol having a molecular weight from about 6000 to about 8000;
VB-201 from about 20 mg to about 100 mg (e.g., about 20 mg to about 80 mg);
talc at a weight ratio from about 1:4 to about 1:1 (talc:VB-201); and
a thixotropic agent (e.g., fumed silicon dioxide) at a concentration relative to the combined weight of said thermosoftening carrier and said thixotropic agent from about 1 weight percent to about 3 weight percent.

According to some embodiments of the present disclosure there is provided a liquid-fill capsule comprising from about 400 mg to about 600 mg of a solid or semi-solid matrix, the matrix consisting of:
VB-201 from about 20 mg to about 100 mg (e.g., about 20 mg to about 80 mg);
An anti-adherent agent (e.g., talc) from about 5 mg to about 100 mg (e.g., from about 10 mg to about 80 mg);
a thixotropic agent (e.g., fumed silicon dioxide) from about 2 mg to about 20 mg (e.g., from about 4 mg to about 12 mg); and
the remainder being a thermosoftening carrier. The thermosoftening carrier may be selected, e.g., from a poloxamer (e.g., poloxamer 188) and a polyethylene glycol having a molecular weight from about 6000 to about 8000.

According to some embodiments there is provided a liquid-fill capsule comprising a capsule shell and a fill composition (matrix), the fill composition comprising:
a thermosoftening carrier;
an oxidized phospholipid at a concentration from about 0.1 weight percent to about 25 weight percent;
an anti-adherent agent at a weight ratio from about 1:5 to about 5:1 anti-adherent agent:oxidized phospholipid; and
a thixotropic agent at a concentration from about 0.25 weight percent to about 10 weight percent relative to the combined weight of the thermosoftening carrier and the thixotropic agent.

According to some embodiments there is provided a liquid-fill capsule comprising a capsule shell and a fill composition (matrix), the fill composition comprising:
a thermosoftening carrier;
VB-201 at a concentration from about 0.1 weight percent to about 25 weight percent;
an anti-adherent agent at a weight ratio from about 1:5 to about 5:1 anti-adherent agent:VB-201; and
a thixotropic agent at a concentration from about 0.25 weight percent to about 10 weight percent relative to the combined weight of the thermosoftening carrier and the thixotropic agent.

According to some embodiments there is provided a liquid-fill capsule comprising a capsule shell and a fill composition (matrix), the fill composition comprising:
a thermosoftening carrier,
VB-201 at a concentration from about 4 weight percent to about 25 weight percent;
an anti-adherent agent at a weight ratio from about 1:4 to about 2:1 anti-adherent agent:VB-201; and
a thixotropic agent at a concentration from about 1 weight percent to about 5 weight percent relative to the combined weight of the thermosoftening carrier and the thixotropic agent.

Optionally, the capsule comprises from about 400 mg to about 600 mg of a fill composition comprising the abovementioned ingredients. Optionally, the capsule comprises from about 440 mg to about 600 mg of the fill composition comprising the abovementioned ingredients. Optionally, the capsule comprises from about 440 mg to about 480 mg of a fill composition comprising the abovementioned ingredients. Optionally, the capsule comprises about from about 560 mg to about 600 mg of a fill composition comprising the abovementioned ingredients.

In some examples according to any of the above embodiments, the total weight of the thermosoftening carrier and the thixotropic agent (if present) in the capsule is about 400 mg. In some embodiments, such a capsule comprises from about 1 mg to about 100 mg of oxidized phospholipid (e.g., VB-201, VB-208, VB-221, or VB-219).

In some embodiments, the ratio of anti-adherent agent (e.g., talc) to VB-201 is 1:1, such that the capsule comprises, for example, 20 mg each of VB-201 and anti-adherent agent, 40 mg each of VB-201 and anti-adherent agent, 80 mg each of VB-201 and anti-adherent agent, or 100 mg each of VB-201 and anti-adherent agent.

In some embodiments the capsule comprises 20 mg of VB-201, 20 mg anti-adherent agent (e.g., talc), and 400 mg of a thermosoftening carrier with a thixotropic agent (e.g., 440 mg fill composition per capsule). In other embodiments the capsule comprises 40 mg of VB-201, 40 mg of an anti-adherent agent (e.g., talc) and 400 mg of a thermosoftening carrier with a thixotropic agent (e.g., 480 mg fill composition per capsule). In other embodiments the capsule comprises 80 mg of VB-201, 80 mg of an anti-adherent agent (e.g., talc) and 400 mg of a thermosoftening carrier with a thixotropic agent (e.g., 560 mg fill composition per capsule). In other embodiments the capsule comprises 100 mg of VB-201, 100 mg of an anti-adherent agent (e.g., talc) and 400 mg of a thermosoftening carrier with a thixotropic agent (e.g., 600 mg fill composition per capsule).

In other embodiments, the ratio of anti-adherent agent (e.g., talc) to VB-201 is 1:2, such that the capsule comprises, for example, 20 mg VB-201 and 10 mg anti-adherent agent, 40 mg VB-201 and 20 mg anti-adherent agent, 60 mg VB-201 and 30 mg anti-adherent agent, 80 mg VB-201 and 40 mg anti-adherent agent, or 100 mg VB-201 and 50 mg anti-adherent agent.

In some embodiments the capsule comprises 20 mg of VB-201, 10 mg of an anti-adherent agent (e.g., talc) and 400 mg of a thermosoftening carrier with a thixotropic agent (e.g., 430 mg fill composition per capsule). In other embodiments the capsule comprises 40 mg of VB-201, 20 mg of an anti-adherent agent (e.g., talc) and 400 mg of a thermosoftening carrier with a thixotropic agent (e.g., 460 mg fill composition per capsule). In other embodiments the capsule comprises 60 mg of VB-201, 30 mg of an anti-adherent agent (e.g., talc) and 400 mg of a thermosoftening carrier with a thixotropic agent (e.g., 490 mg fill composition per capsule). In other embodiments the capsule comprises 80 mg of VB-201, 40 mg of an anti-adherent agent (e.g., talc) and 400 mg of a thermosoftening carrier with a thixotropic agent (e.g., 520 mg fill composition per capsule). In other embodiments the capsule comprises 100 mg of VB-201, 50 mg of an anti-adherent agent (e.g., talc) and 400 mg of a thermosoftening carrier with a thixotropic agent (e.g., 550 mg fill composition per capsule).

In other embodiments, the ratio of anti-adherent agent (e.g., talc) to VB-201 is 1:4, such that the capsule comprises, for example, 20 mg VB-201 and 5 mg anti-adherent agent, 40 mg VB-201 and 10 mg anti-adherent agent, 60 mg VB-201 and 15 mg anti-adherent agent, 80 mg VB-201 and 20 mg anti-adherent agent, or 100 mg VB-201 and 25 mg anti-adherent agent.

In some embodiments the capsule comprises 20 mg of VB-201, 5 mg of an anti-adherent agent (e.g., talc) and 400 mg of a thermosoftening carrier with a thixotropic agent (e.g., 425 mg fill composition per capsule). In other embodiments the capsule comprises 40 mg of VB-201, 10 mg of an anti-adherent agent (e.g., talc) and 400 mg of a thermosoftening carrier with a thixotropic agent (e.g., 450 mg fill composition per capsule). In other embodiments the capsule comprises 60 mg of VB-201, 15 mg of an anti-adherent agent (e.g., talc) and 400 mg of a thermosoftening carrier with a thixotropic agent (e.g., 475 mg fill composition per capsule). In other embodiments the capsule comprises 80 mg of VB-201, 20 mg of an anti-adherent agent (e.g., talc) and 400 mg of a thermosoftening carrier with a thixotropic agent (e.g., 500 mg fill composition per capsule). In other embodiments the capsule comprises 100 mg of VB-201, 25 mg of an anti-adherent agent (e.g., talc) and 400 mg of a thermosoftening carrier with a thixotropic agent (e.g., 525 mg fill composition per capsule).

In one example according to any of the above embodiments, the carrier is a poloxamer (e.g., poloxamer 188). Optionally, the carrier is a polyethylene glycol having a molecular weight of about 6000 (e.g., ±10%).

In embodiments where a capsule comprises about 400 mg of thermosoftening carrier and thixotropic agent, the capsule comprises, for example, 20 mg of VB-201, 20 mg anti-adherent agent, and a total of 440 mg of fill composition per capsule; 40 mg of VB-201, 40 mg anti-adherent agent, and 480 mg of fill composition per capsule; or 80 mg of VB-201, 80 mg anti-adherent agent and 560 mg of fill composition per capsule. Optionally, the carrier is a poloxamer (e.g., poloxamer 188). Optionally, the carrier is a polyethylene glycol having a molecular weight of 6000 (+10%). The 400 mg of thermosoftening carrier with thixotropic agent may consist of, for example, 12 mg thixotropic agent with 388 mg carrier, 10 mg thixotropic agent with 390 mg carrier, or 4 mg thixotropic agent with 396 mg of thermosoftening carrier.

The thixotropic agent is optionally from about 1 to about 5 weight percent, e.g., from about 1 to about 3, from about 2 to about 3, or from about 2.5 to about 3 weight percent thixotropic agent (e.g., fumed silica) relative to the combined weight of the thixotropic agent and the thermosoftening carrier. For example, the fill composition may contain 12 mg thixotropic agent and 388 mg thermosoftening carrier, 10 mg thixotropic agent and 390 mg thermosoftening carrier, 9 mg thixotropic agent and 351 mg thermosoftening carrier, or 7 mg thixotropic agent and 273 mg thermosoftening carrier. In other examples, the fill composition may contain 9 mg thixotropic agent and 391 mg thermosoftening carrier, 8 mg thixotropic agent and 392 mg thermosoftening carrier, 7 mg thixotropic agent and 393 thermosoftening carrier, 6 mg thixotropic agent and 394 mg thermosoftening carrier, 5 mg thixotropic agent and 395 mg thermosoftening carrier, 4 mg thixotropic agent and 396 mg thermosoftening carrier, or 3 mg thixotropic agent and 397 mg thermosoftening carrier.

In some embodiments, the thermosoftening carrier is a polyethylene glycol carrier and the fill composition comprises about 2.5 weight percent of a thixotropic agent (e.g., fumed silica), for example, 390 mg of a polyethylene glycol carrier (e.g., PEG 6000) with 10 mg thixotropic agent. In other embodiments, the fill composition comprises a polyethylene glycol carrier (e.g., PEG 6000) and about 1 weight percent thixotropic agent (e.g., fumed silica), for example, 396 mg carrier with 4 mg thixotropic agent.

In some embodiments, the thermosoftening carrier is a poloxamer (e.g., poloxamer 188) and the fill composition comprises about 3 weight percent thixotropic agent (e.g., fumed silica), for example, 388 mg carrier with 12 mg thixotropic agent. In some embodiments, the thermosoftening carrier is a poloxamer (e.g., poloxamer 188) and the fill composition comprises about 1 weight percent thixotropic agent (e.g., fumed silica), for example, 396 mg thermosoftening carrier and 4 mg thixotropic agent.

According to some embodiments of the present disclosure there is provided a liquid-fill capsule comprising:
VB-201 at a concentration that ranges from 0.1 weight percent to 25 weight percent;
an anti-adherent agent at a weight ratio in a range of from 1:3 to 5:1 anti-adherent agent:VB-201;
a thixotropic agent at a concentration in a range of from 0.25 weight percent to 10 weight percent; and
the balance being a thermosoftening carrier.

According to some embodiments of the present disclosure there is provided a liquid-fill capsule comprising:
from about 20 mg to about 100 mg VB-201;
5 mg to about 100 mg of an anti-adherent agent;
2 mg to about 12 mg of a thixotropic agent; and
388 mg to about 398 mg of a thermosoftening carrier.

According to some embodiments of the present disclosure there is provided a liquid-fill capsule comprising:
20 mg VB-201;
20 mg of an anti-adherent agent;
12 mg of a thixotropic agent; and
388 mg of a thermosoftening carrier.

According to some embodiments of the present disclosure there is provided a liquid-fill capsule comprising:
20 mg VB-201;
20 mg talc;
12 mg fumed silica; and
388 mg of poloxamer 188.

According some embodiments of the present disclosure there is provided a liquid-fill capsule comprising:
40 mg VB-201;
40 mg of an anti-adherent agent;
12 mg of a thixotropic agent; and
388 mg of a thermosoftening carrier.

According some embodiments of the present disclosure there is provided a liquid-fill capsule comprising:
40 mg VB-201;
40 mg talc;
12 mg of fumed silicon dioxide; and
388 mg of a poloxamer.

According some embodiments of the present disclosure there is provided a liquid-fill capsule comprising:
40 mg VB-201;
40 mg talc;
12 mg fumed silicon dioxide; and
388 mg of poloxamer 188.

According some embodiments of the present disclosure there is provided a liquid-fill capsule comprising:
40 mg VB-201;
10 mg of an anti-adherent agent;
4 mg of a thixotropic agent; and
396 mg of a thermosoftening carrier.

According some embodiments of the present disclosure there is provided a liquid-fill capsule comprising:
40 mg VB-201;
10 mg talc;
4 mg of fumed silicon dioxide; and
396 mg of a poloxamer.

According some embodiments of the present disclosure there is provided a liquid-fill capsule comprising:
40 mg VB-201;
10 mg talc;
4 mg fumed silicon dioxide; and
396 mg of poloxamer 188.

According some embodiments of the present disclosure there is provided a liquid-fill capsule comprising:
60 mg VB-201;
15 mg of an anti-adherent agent;
4 mg of a thixotropic agent; and
396 mg of a thermosoftening carrier.

According some embodiments of the present disclosure there is provided a liquid-fill capsule comprising:
60 mg VB-201;
15 mg talc;

4 mg of fumed silicon dioxide; and
396 mg of a poloxamer.

According some embodiments of the present disclosure there is provided a liquid-fill capsule comprising:
60 mg VB-201;
15 mg talc;
4 mg fumed silicon dioxide; and
396 mg of poloxamer 188.

According to some embodiments of the present invention there is provided a liquid-fill capsule comprising:
80 mg VB-201;
80 mg of an anti-adherent agent;
12 mg of a thixotropic agent; and
388 mg of a thermosoftening carrier.

According to some embodiments of the present invention there is provided a liquid-fill capsule comprising:
80 mg VB-201;
80 mg talc;
12 mg fumed silica; and
388 mg of poloxamer 188.

According some embodiments of the present disclosure there is provided a liquid-fill capsule comprising:
80 mg VB-201;
20 mg of an anti-adherent agent;
4 mg of a thixotropic agent; and
396 mg of a thermosoftening carrier.

According some embodiments of the present disclosure there is provided a liquid-fill capsule comprising:
80 mg VB-201;
20 mg talc;
4 mg of fumed silicon dioxide; and
396 mg of a poloxamer.

According some embodiments of the present disclosure there is provided a liquid-fill capsule comprising:
80 mg VB-201;
20 mg talc;
4 mg fumed silicon dioxide; and
396 mg of poloxamer 188.

In other embodiments the present disclosure provides a capsule comprising VB-201 and a thermosoftening carrier.

Liquid-Fill Compositions

The liquid-fill composition is a pharmaceutical composition of the present disclosure suitable to be filled into a pharmaceutical receptacle (e.g., liquid-fill capsule). According to some embodiments of the present disclosure, there is provided a liquid fill composition comprising VB-201, VB-208, VB-219, and/or VB-221 and a thermosoftening carrier, as described herein, and optionally one or more of an anti-adherent agent, a thixotropic agent and/or a gelling agent, as described herein. Optionally, the liquid fill composition is liquid only at a temperature above room temperature (i.e., above 25° C.). According to other embodiments of the present disclosure, there is provided a liquid fill composition comprising VB-201 and a thermosoftening carrier, as described herein, and optionally one or more of an anti-adherent agent, a thixotropic agent and/or a gelling agent, as described herein. Optionally, the liquid-fill composition is liquid only at a temperature above room temperature (i.e., above 25° C.).

Amounts, proportions and concentrations of the ingredients of the liquid fill composition are described herein in the context of the pharmaceutical compositions. Also described herein are methods and procedures for mixing the ingredients to obtain the liquid fill composition.

Formulations Providing Pharmacokinetic Parameters

In some embodiments, the pharmaceutical composition or the liquid-fill capsule according to any of the embodiments described herein, when orally administered to a human subject, e.g., at a single oral dose of about 40 mg of VB-201, provides a mean maximum plasma concentration ($C_{max}$) of VB-201 from about 1,000 ng/mL to about 1,600 ng/mL (e.g., from about 1,100 ng/mL to about 1,500 ng/mL, or from about 1,200 ng/mL to about 1,400 ng/mL, or from about 1,200 ng/mL to about 1,300 ng/mL.

In some embodiments, the pharmaceutical composition or the liquid-fill capsule according to any of the embodiments described herein, when orally administered to a human subject, e.g., at a single oral dose of about 40 mg of VB-201, provides a median time to mean maximum plasma concentration (Tmax) of VB-201 from about 5 hours to about 10 hours (e.g., from about 5 hours to about 7.5 hours, or from about 6 hours to about 6.5 hours).

In some embodiments, the pharmaceutical composition or the liquid-fill capsule according to any of the embodiments described herein, when orally administered to a human subject, e.g., at a single oral dose of about 40 mg of VB-201, provides a plasma concentration time curve with a mean area under the curve ($AUC_\infty$) ranging from about 45,000 to about 70,000 ng h/mL, e.g., from about 50,000 to about 65,000 ng h/mL, or from about 55,000 to about 60,000 ng h/mL.

In some embodiments, the pharmaceutical composition or the liquid-fill capsule according to any of the embodiments described herein, when orally administered to a human subject, e.g., at a single oral dose of about 40 mg of VB-201, provides a mean terminal half-live ($t_{1/2}$) between about 32 and about 42 hours (e.g., between about 35 and about 40 hours, or between about 36 and about 38 hours, or about 37 hours).

In some embodiments, the pharmaceutical composition or the liquid-fill capsule according to any of the embodiments described herein, when orally administered to a human subject, e.g., at a single oral dose of about 40 mg of VB-201, provides a mean maximum plasma concentration ($C_{max}$) of VB-201 from about 1,000 ng/mL to about 1,600 ng/mL (e.g., from about 1,100 ng/mL to about 1,500 ng/mL, or from about 1,200 ng/mL to about 1,400 ng/mL, or from about 1,200 ng/mL to about 1,300 ng/mL), and a median time to mean maximum plasma concentration (Tmax) of VB-201 from about 5 hours to about 10 hours (e.g., from about 5 hours to about 7.5 hours, or from about 6 hours to about 6.5 hours).

In some embodiments, the pharmaceutical composition or the liquid-fill capsule according to any of the embodiments described herein, when orally administered to a human subject, e.g., at a single oral dose of about 40 mg of VB-201, provides a mean maximum plasma concentration ($C_{max}$) of VB-201 from about 1,000 ng/mL to about 1,600 ng/mL (e.g., from about 1,100 ng/mL to about 1,500 ng/mL, or from about 1,200 ng/mL to about 1,400 ng/mL, or from about 1,200 ng/mL to about 1,300 ng/mL), a median time to mean maximum plasma concentration (Tmax) of VB-201 from about 5 hours to about 10 hours (e.g., from about 5 hours to about 7.5 hours, or from about 6 hours to about 6.5 hours), and a mean area under the curve ($AUC_\infty$) ranging from about 45,000 to about 70,000 ng h/mL (e.g., from about 50,000 to about 65,000 ng h/mL, or from about 55,000 to about 60,000 ng h/mL).

In some embodiments, the pharmaceutical composition or the liquid-fill capsule according to any of the embodiments described herein, when orally administered to a human subject, e.g., at a single oral dose of about 40 mg of VB-201, provides a mean maximum plasma concentration ($C_{max}$) of VB-201 from about 1,000 ng/mL to about 1,600 ng/mL (e.g., from about 1,100 ng/mL to about 1,500 ng/mL, or from about 1,200 ng/mL to about 1,400 ng/mL, or from about 1,200 ng/mL to about 1,300 ng/mL), a median time to mean maximum plasma concentration (Tmax) of VB-201 from about 5 hours to about 10 hours (e.g., from about 5 hours to about 7.5 hours, or from about 6 hours to about 6.5 hours), a mean area under the curve (AUCC$_\infty$) ranging from about 45,000 to about 70,000 ng h/mL (e.g., from about 50,000 to about 65,000 ng h/mL, or from about 55,000 to about 60,000 ng h/mL), and a mean terminal half-live (t%) between about 32 and about 42 hours (e.g., between about 35 and about 40 hours, or between about 36 and about 38 hours, or about 37 hours).

In some embodiments, the present disclosure provides a VB-201 formulation, wherein the formulation when orally administered to a human subject, e.g., at a single oral dose of about 40 mg of VB-201, provides a mean maximum plasma concentration ($C_{max}$) of VB-201 from about 1,000 ng/mL to about 1,600 ng/mL (e.g., from about 1,100 ng/mL to about 1,500 ng/mL, or from about 1,200 ng/mL to about 1,400 ng/mL, or from about 1,200 ng/mL to about 1,300 ng/mL).

In some embodiments, the present disclosure provides a VB-201 formulation, wherein the formulation when orally administered to a human subject e.g., at a single oral dose of about 40 mg of VB-201, provides a median time to mean maximum plasma concentration ($T_{max}$) of VB-201 from about 5 hours to about 10 hours (e.g., from about 5 hours to about 7.5 hours, or from about 6 hours to about 6.5 hours).

In some embodiments, the present disclosure provides a VB-201 formulation, wherein the formulation when orally administered to a human subject, e.g., at a single oral dose of about 40 mg of VB-201, provides a plasma concentration time curve with a mean area under the curve (AUC$_\infty$) ranging from about 45,000 to about 70,000 ng h/mL (e.g., from about 50,000 to about 65,000 ng h/mL, or from about 55,000 to about 60,000 ng h/mL).

In some embodiments, the present disclosure provides a VB-201 formulation, wherein the formulation when orally administered to a human subject, e.g., at a single oral dose of about 40 mg of VB-201, provides a mean terminal half-live ($t_{1/2}$) between about 32 and about 42 hours (e.g., between about 35 and about 40 hours, or between about 36 and about 38 hours, or about 37 hours).

In some embodiments, the present disclosure provides a formulation, wherein the formulation when orally administered to a human subject, e.g., at a single oral dose of about 40 mg of VB-201, provides a mean maximum plasma concentration ($C_{max}$) of VB-201 from about 1,000 ng/mL to about 1,600 ng/mL (e.g., from about 1,100 ng/mL to about 1,500 ng/mL, or from about 1,200 ng/mL to about 1,400 ng/mL, or from about 1,200 ng/mL to about 1,300 ng/mL), and a median time to mean maximum plasma concentration ($T_{max}$) of VB-201 from about 5 hours to about 10 hours (e.g., from about 5 hours to about 7.5 hours, or from about 6 hours to about 6.5 hours.

In some embodiments, the present disclosure provides a formulation, wherein the formulation when orally administered to a human subject, e.g., at a single oral dose of about 40 mg of VB-201, provides a mean maximum plasma concentration ($C_{max}$) of VB-201 from about 1,000 ng/mL to about 1,600 ng/mL (e.g., from about 1,100 ng/mL to about 1,500 ng/mL, or from about 1,200 ng/mL to about 1,400 ng/mL, or from about 1,200 ng/mL to about 1,300 ng/mL), a median time to mean maximum plasma concentration ($T_{max}$) of VB-201 from about 5 hours to about 10 hours (e.g., from about 5 hours to about 7.5 hours, or from about 6 hours to about 6.5 hours), and a plasma concentration time curve with a mean area under the curve (AUC$_\infty$) ranging from about 45,000 to about 70,000 ng h/mL (e.g., from about 50,000 to about 65,000 ng h/mL, or from about 55,000 to about 60,000 ng h/mL).

In other embodiments the present disclosure provides a pharmaceutical formulation comprising VB-201, wherein the formulation, when orally administered to a human subject, e.g., at a single oral dose of about 40 mg VB-201, provides a mean maximum plasma concentration ($C_{max}$) of VB-201 from about 1,000 ng/mL to about 1,600 ng/mL (e.g., from about 1,100 ng/mL to about 1,500 ng/mL, or from about 1,200 ng/mL to about 1,400 ng/mL, or from about 1,200 ng/mL to about 1,300 ng/mL) a median time to mean maximum plasma concentration ($T_{max}$) of VB-201 from about 5 hours to about 10 hours (e.g., from about 5 hours to about 7.5 hours, or from about 6 hours to about 6.5 hours), a plasma concentration time curve with a mean area under the curve (AUC$_\infty$) ranging from about 45,000 to about 70,000 ng h/mL (e.g., from about 50,000 to about 65,000 ng h/mL, or from about 55,000 to about 60,000 ng h/mL), and a mean terminal half-live ($t_{1/2}$) between about 32 and about 42 hours (e.g., between about 35 and about 40 hours, or between about 36 and about 38 hours, or about 37 hours).

In other embodiments the present disclosure provides a pharmaceutical formulation comprising VB-201, wherein the formulation, when orally administered to a human subject, e.g., at a single oral dose of about 40 mg VB-201, provides the following mean values for $C_{max}$, $T_{max}$, AUC and $t_{1/2}$ with the indicated standard deviations (SD):

$C_{max}$ (ng/mL): 1289.74 (SD: 232.25)
$T_{max}$ (h): 6.00 (mean) (from 5.00-10.00)
$AUC_T$ (ng·h/mL): 53200 (SD: 12500)
$AUC_\infty$ (ng·h/mL): 57500 (SD: 12000)
t½ (h): 37.4 (SD: 4.98)
$C_{max}$ (ng/mL): 1298.08 (SD: 230.97)
$T_{max}$ (h): 6.50 (mean) (from 5.00-9.00)
$AUC_T$ (ng·h/mL): 55000 (SD: 13900)
$AUC_\infty$ (ng·h/mL): 58900 (SD: 14500)
t½ (h): 37.2 (SD: 6.07)

In some examples, according to any of the above embodiments the VB-201 formulation is selected from the liquid-fill capsule formulations described herein (e.g., a liquid-fill capsules containing about 40 mg VB-201). In some examples according to any of the above embodiments, the formulation is selected from formulation 10 of example 13, formulation 4 of example 11, and formulation 7 of example 12.

In some embodiments, the above described pharmacokinetic parameters are measured as described in Example 15.

Oxidized Phospholipids

In some embodiments, the active pharmaceutical ingredients useful in the formulations, pharmaceutical compositions, liquid-fill compositions, capsules, and methods of the present disclosure include at least one oxidized phospholipid. The oxidized phospholipid may be characterized by at least a certain degree of adhesiveness or stickiness at room temperature (i.e., 25° C.).

In one example according to any of the embodiments described herein, the oxidized phospholipid has a structure according to Formula (I):

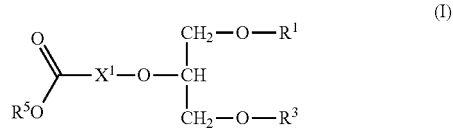

In Formula (I), $R^1$ is $C_{10}$-$C_{30}$ straight or branched alkyl. In some examples, $R^1$ is $C_{12}$-$C_{30}$ straight or branched alkyl. In some examples, $R^1$ is $C_{14}$-$C_{30}$ straight or branched alkyl. In other examples, $R^1$ is $C_{12}$-$C_{25}$ straight or branched alkyl. In other examples, $R^1$ is $C_{12}$-$C_{20}$ straight or branched alkyl. In other examples, $R^1$ is $C_{14}$-$C_{20}$ straight or branched alkyl. In other examples, $R^1$ is $C_{16}$-$C_{20}$ straight or branched alkyl. In other examples, $R^1$ is selected from tetradecyl, pentadecyl, hexadecyl, heptadecyl, octadecyl, nonadecyl, eicosanyl, cis-9-hexadecenyl, and (2-octyl)dodecyl. In other examples, $R^1$ is a branched $C_{10}$-$C_{30}$ alkyl. In another example, $R^1$ is a branched $C_2$-$C_{20}$ alkyl. In yet another example, $R^1$ in Formula (I) is hexadecyl (—$C_{16}H_{33}$).

In Formula (I), $R^3$ is selected from phosphatidylethanolamine, phosphatidylcholine, thiophosphatidylcholine, phosphatitylethanolamine-N-glutaric acid, and phosphatidylserine. In one example, $R^3$ is selected from phosphatidylethanolamine and phosphatidylcholine. In some embodiments $R^3$ is phosphatidylcholine.

$R^5$ in Formula (I) is a member selected from H, a negative charge, and $C_1$-$C_6$ straight or branched alkyl. In some examples, $R^5$ is $C_1$-$C_4$ straight or branched alkyl. In other examples, $R^5$ is selected from H, a negative charge, methyl, and ethyl. In some examples, $R^5$ is selected from H and a negative charge. In other examples, $R^5$ in Formula (I) is H. In yet other examples, $R^5$ in Formula (I) is methyl.

In Formula (I), $X^1$ is $C_2$-$C_6$ alkylene. In some examples, $X^1$ is $C_3$-$C_6$ alkylene. In other examples, $X^1$ is $C_3$, $C_4$, $C_5$ or $C_6$ alkylene. In other examples, $X^1$ is $C_4$ or $C_5$ alkylene. In other examples, $X^1$ in Formula (I) is $C_4$ alkylene (—$CH_2$—$CH_2$—$CH_2$—$CH_2$—).

In some examples, $R^3$ in Formula (I) is phosphatidylcholine and the oxidized phospholipid has a structure according to Formula (II):

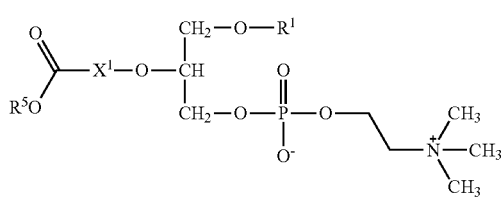

wherein $R^1$, $R^5$, and $X^1$ are defined as for Formula (I). In one example in Formula (II), $R^1$ is selected from tetradecyl, pentadecyl, hexadecyl, heptadecyl, octadecyl, nonadecyl, eicosanyl, cis-9-hexadecenyl, and (2-octyl)dodecyl. In yet another example, $R^1$ in Formula (II) is hexadecyl (—$C_6H_{33}$). In another example in Formula (II), $X^1$ is $C_4$ or $C_5$ alkylene. In another example $X^1$ in Formula (II) is $C_4$ alkylene (—$CH_2$—$CH_2$—$CH$—$CH_2$—). In one example in Formula (II), $R^5$ is H, a negative charge or methyl. In another example in Formula (II), $R^1$ is selected from tetradecyl, pentadecyl, hexadecyl, heptadecyl, octadecyl, nonadecyl, eicosanyl, cis-9-hexadecenyl, and (2-octyl)dodecyl, $X^1$ is $C_4$ or $C_5$ alkylene, and $R^5$ is H, a negative charge or methyl.

In other examples, $X^1$ in Formula (II) is $C_4$ alkylene (—$CH_2$—$CH_2$—$CH_2$—$CH_2$—), and the oxidized phospholipid has a structure according to Formula (III):

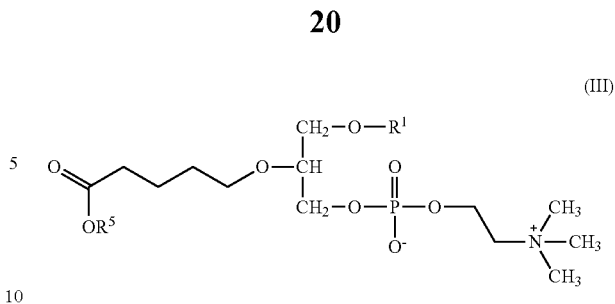

wherein $R^1$ and $R^5$ are defined as for Formula (I). In one example in Formula (III), $R^1$ is selected from tetradecyl, pentadecyl, hexadecyl, heptadecyl, octadecyl, nonadecyl, eicosanyl, cis-9-hexadecenyl, and (2-octyl)dodecyl. In another example in Formula (II), $R^5$ is H, a negative charge or methyl. In another example in Formula (III), $R^5$ is H or a negative charge. In another example in Formula (III), $R^1$ is selected from tetradecyl, pentadecyl, hexadecyl, heptadecyl, octadecyl, nonadecyl, eicosanyl, cis-9-hexadecenyl, and (2-octyl) dodecyl, and $R^5$ is H, a negative charge or methyl. In yet another example, $R^1$ in Formula (III) is hexadecyl (—$C_{16}H_{33}$). In yet another example, $R^1$ in Formula (III) is hexadecyl (—$C_{16}H_{33}$), and $R^5$ is H, a negative charge or methyl.

The structures of Formulae (I), (II), and (III) are meant to include all stereoisomers and mixtures thereof.

In some embodiments, the oxidized phospholipid is VB-201 [1-hexadecyl-2-(4'-carboxybutyl)-glycero-3-phosphocholine] having the formula:

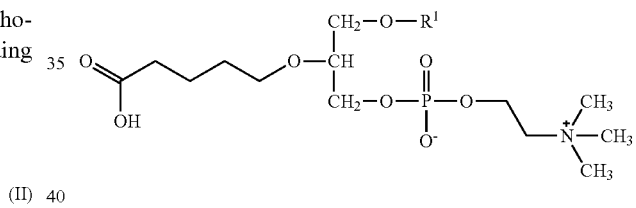

In some embodiments, the oxidized phospholipid is VB-208 [1-hexadecyl-2-(4'-methyl-carboxybutyl)-glycero-3-phosphocholine] having the formula:

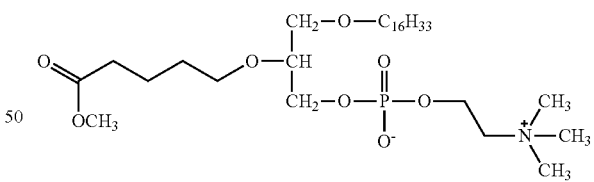

In some embodiments, the oxidized phospholipid is VB-219 [1-eicosanyl-2-(4'-carboxybutyl)-glycero-3-phosphocholine] having the formula:

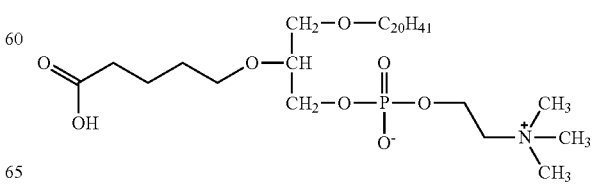

In some embodiments, the oxidized phospholipid is VB-221 [1-(2'-octyl)dodecyl-2-(4'-carboxybutyl)-glycero-3-phosphocholine] having the formula:

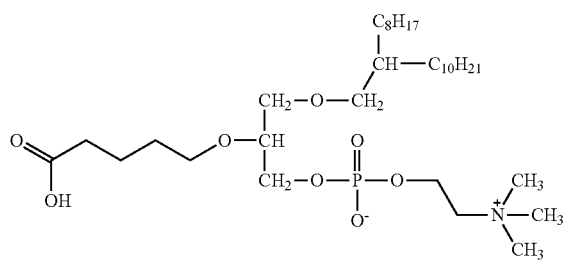

VB-201 according to embodiments of the present invention may be a chiral enantiomer of 1-hexadecyl-2-(4'-carboxybutyl)glycero-3-phosphocholine, i.e., either the (R)-enantiomer ((R)-1-hexadecyl-2-(4'-carboxybutyl)-sn-glycero-3-phosphocholine) or the (S)-enantiomer ((S)-1-hexadecyl-2-(4'-carboxybutyl)-glycero-3-phosphocholine), or a mixture thereof (e.g., a racemate). According to exemplary embodiments, VB-201 is (R)-1-hexadecyl-2-(4'-carboxybutyl)-sn-glycero-3-phosphocholine.

In some embodiments, the compositions of the present disclosure include more than one oxidized phospholipid, e.g., two, three, or more oxidized phospholipids, each independently selected from those described herein.

Capsules

As used herein, the general term "capsule" or "capsules" is intended to encompass any suitable capsular container or case adapted for oral ingestion, e.g., those adapted for use in conjunction with liquid fill compositions. The term "capsule" includes capsules having a shell composed of soft and/or hard materials, such as gelatin, starches, celluloses, cellulose derivatives (e.g., hydroxypropyl methyl cellulose), hydrocolloids, gums, carrageenans, or any other natural or synthetic material which can be used to encapsulate the liquid composition and be ingested by an animal. Optionally, the shell material is gelatin and/or hydroxypropyl methyl cellulose. In optional embodiments, the shell material is gelatin. The term "capsule" is intended to include a variety of capsule shapes and sizes, and is not intended to limit the dosage form to a specific type or shape. Any commercially available capsule shells or shell materials are contemplated.

In some embodiments, the capsule is a size 0 capsule. In some embodiments, the capsule is a size 1 capsule. In some embodiments, the capsule is a size 2 capsule. In some embodiments, the capsule is a size 3 capsule. Other capsule sizes are also contemplated.

The capsule may be formulated, for example, for oral administration or as a suppository. According to exemplary embodiments, the capsule is formulated for oral administration.

A capsule, according to the present embodiments, is therefore composed of a matrix containing therein a pharmaceutically active ingredient (e.g., VB-201, VB-208, VB-221, or VB-219) and a shell which encapsulates the matrix.

In some embodiments, the capsule is a liquid-fill capsule.

The term "liquid-fill capsule" refers to a capsule that is filled with a fill composition that is a liquid during the encapsulation process. It is to be appreciated that the fill composition need not remain a liquid after encapsulation, and that the term "liquid-fill" therefore does not necessarily indicate that the final capsule contains any liquid. In one example, the liquid-fill capsule is a hard-shell capsule (e.g., a hard-shell gelatin capsule).

In some embodiments, the liquid-fill capsule which comprises the active pharmaceutical ingredient (e.g., VB-201, VB-208, VB-221, or VB-219) is a solubilized form within a matrix that contains the active ingredient (e.g., a pharmaceutically acceptable carrier).

In some embodiments, the liquid-fill capsule is such that the matrix containing the active pharmaceutical ingredient (e.g., VB-201, VB-208, VB-221, or VB-219) is a solid or semi-solid.

The phrase "solid or semi-solid matrix" refers herein to a matrix that is a solid or semi-solid at room temperature (e.g., 25° C.). The term "semi-solid" encompasses gels and highly viscous substances, for example, substances characterized by a viscosity of at least about 50,000 centipoise, and optionally at least about 200,000 centipoise.

Typically, the solid or semi-solid matrix is formed from components of the liquid fill composition (e.g., by cooling).

It is to be appreciated that a capsule comprising a solid or semi-solid matrix is resistant to leakage, as a solid or semi-solid matrix will not readily leak from the capsule.

Without being bound by any particular theory, it is also believed that a solid or semi-solid matrix will prevent cracking of the capsule and leakage of the capsule contents by shielding the oxidized phospholipid (e.g., VB-201, VB-208, VB-221, or VB-219) from moisture, thereby preventing the absorption of moisture by the oxidized phospholipid (e.g., VB-201, VB-208, VB-221, or VB-219) from the surroundings (e.g., from the capsule shell) which promotes cracking.

Carrier

As used herein, the term "carrier" refers to a substance or mixture of substances, optionally an inert substance, added to facilitate preparation of the capsule and administration of the oxidized phospholipid (e.g., VB-201, VB-208, VB-221, or VB-219). In some embodiments, the carrier is a pharmaceutically acceptable carrier. Herein, the phrase "pharmaceutically acceptable carrier" describes a carrier or a diluent that does not cause significant irritation to the subject and does not abrogate the biological activity and properties of the active pharmaceutical ingredient (e.g., VB-201, VB-208, VB-221, or VB-219). The carrier includes a thermosoftening carrier and may include additional components, such as other excipients, diluents, coloring agents, and the like.

Thermosoftening Carrier

As used herein, the term "thermosoftening carrier" refers to a carrier which becomes soft (e.g., a fluid) upon heating to a temperature above room temperature. A thermosoftening carrier becomes soft at a temperature which does not damage the active pharmaceutical ingredient (e.g., by oxidation) or the thermosoftening carrier itself. The softening upon heating may be either characterized by a phase transition (e.g., a solid-to-liquid transition), or not characterized by a phase transition (e.g., softening of an amorphous material). The thermosoftening is reversible, such that the softened carrier becomes harder upon being cooled back to room temperature. In some embodiments, the thermosoftening carrier is a mixture of two or more agents.

The thermosoftening carrier facilitates preparation of a liquid fill composition and filling of capsules therewith at a temperature at which the thermosoftening carrier is soft, as well as formation of a solid or semi-solid matrix following cooling (e.g., cooling to room temperature). In one example, the thermosoftening carrier is a solid or a semi-solid at a temperature below 35° C., or below 30° C. (e.g., at room temperature, i.e., 25° C.). In one example, the thermosoftening carrier is non-hygroscopic. The thermosoftening carrier is a pharmaceutically acceptable carrier.

Optionally, the thermosoftening carrier becomes soft at a temperature of no more than about 150° C., and optionally at a temperature of no more than about 100° C., or 90° C.

In some embodiments, the thermosoftening carrier has a melting point in a range of from about 40° C. to about 100° C. Optionally, the melting point is in a range of from about 50° C. to about 80° C. In other examples, the melting point of the thermosoftening carrier is from about 50° C. to about 70° C., or from about 50° C. to about 60° C., and optionally in a range of from about 55° C. to about 65° C. Accordingly, at such temperatures, the thermosoftening carrier undergoes transformation from a hard to a soft material, and vice versa. In one example, the thermosoftening carrier at a temperature above its melting point is sufficiently soft for filling the carrier into a capsule (e.g., into a hard gelatin capsule).

Examples of thermosoftening carriers include waxes, poloxamers (e.g., Poloxamer 188), macrogol glycerides, high-molecular weight PEGs (e.g., PEG6000 or PEG 8000), glycerol monooleates or monostearates, hydrogenated or partially hydrogenated glycerides (e.g., hydrogenated palm kernel oil or hydrogenated cotton seed oil)), Gelucires™, and hard fats such as beeswax. Other exemplary thermosoftening carriers include Softisan™ and hexadecane-1-ol.

The thermosoftening carrier may be a polyalkylene glycol. In one example, the polyalkylene glycol has a high molecular weight, e.g., a molecular weight that is sufficient to render the polyalkylene glycol carrier non-hygroscopic (e.g., a polyalkylene glycol having a molecular weight of at least about 1000 daltons, or at least about 1500 daltons). In one example, the polyalkylene glycol has a molecular weight of at least about 2000 daltons. In another example, the polyalkylene glycol has a molecular weight of at least about 3000 daltons. In another example, the polyalkylene glycol has a molecular weight of at least about 4000 daltons. In another example, the polyalkylene glycol has a molecular weight of at least about 5000 daltons. In another example, the polyalkylene glycol has a molecular weight of at least about 6000 daltons. It is to be understood that a molecular weight in connection with polyalkylene glycols described herein is meant to represent an average molecular weight in accordance with commonly used nomenclature for such compounds. Suitable polyalkylene glycols include, without limitation, polyethylene glycols, polypropylene glycols and copolymers thereof, such as poloxamers (e.g., poloxamers 188, 237, 338 and 407).

In some embodiments, the polyalkylene glycol is a poloxamer. Accordingly, in some embodiments, the thermosoftening carrier is a poloxamer.

Poloxamers are triblock polyalkylene glycols, comprising a central polypropylene glycol chain, which is relatively hydrophobic, flanked by two polyethylene glycol chains, which are relatively hydrophilic. This combination of hydrophobic and hydrophilic chains provides poloxamers with surfactant properties.

Poloxamers are typically characterized by molecular weight of the polypropylene glycol core of the poloxamer and by the proportion of polyethylene glycol versus polypropylene glycol. These parameters are commonly described by characterizing a poloxamer with a three-digit number, wherein the first two digits, when multiplied by 100, give the molecular weight (in daltons) of the polypropylene glycol core, whereas the last digit, when multiplied by 10, gives the percentage of polyethylene glycol. Thus, for example, poloxamer 188 has a polypropylene glycol core with a molecular weight of 1800 daltons and is 80% polyethylene glycol (and thus has a total molecular weight of approximately 9000 daltons), whereas poloxamer 407 has a polypropylene glycol core with a molecular weight of 4000 daltons and is 70% polyethylene glycol (and thus has a total molecular weight of approximately 13000 daltons).

According to some embodiments, the poloxamer has a molecular weight in a range of from about 2000 to about 18000 daltons. Optionally, the poloxamer has a molecular weight in a range of from about 4000 to 15000 daltons, and optionally from about 6000 to about 12000 daltons. In exemplary embodiments, the molecular weight of the poloxamer is in a range of from about 7000 to about 10000 daltons. In other examples, the poloxamer has a molecular weight from about 4000 to about 18,000 daltons, from about 6000 to about 18,000 daltons, from about 6000 to about 14,000 daltons, or from about 8000 to about 10,000 daltons. In one example, the poloxamer has a molecular weight of about 9000 daltons.

According to some embodiments, the polypropylene core of the poloxamer has a molecular weight in a range of from about 1000 to about 5000 daltons. Optionally the polypropylene core of the poloxamer has a molecular weight in a range of from about 1200 to about 2400 daltons, and optionally from about 1500 to about 2100 daltons. In exemplary embodiments, the molecular weight of the polypropylene core of the poloxamer is about 1800 daltons.

According to some embodiments, the poloxamer comprises at least about 20 weight percent of polyethylene glycol, optionally at least about 30 weight percent, optionally at least about 40 weight percent, optionally at least about 50 weight percent, optionally at least about 60 weight percent, optionally at least about 70 weight percent, and optionally at least about 80 weight percent of polyethylene glycol.

In some embodiments the proportion of polyethylene glycol in the poloxamer is in a range of from 40 to 90 weight percent, optionally from 50 to 90 weight percent, optionally from 60 to 90 weight percent, and optionally from 70 to 90 weight percent. In exemplary embodiments the poloxamer comprises about 80 weight percent polyethylene glycol.

Poloxamer 188 is an exemplary poloxamer. Accordingly, in some embodiments, the thermosoftening carrier is poloxamer 188.

In some embodiments, the thermosoftening carrier is a polyethylene glycol. Optionally, the polyethylene glycol has a molecular weight in a range of from about 1500 to about 10,000 daltons, or about 1500 to about 8000 daltons, optionally from about 4000 to about 8000 daltons, and optionally from about 5000 to about 7000 daltons. In exemplary embodiments, the polyethylene glycol has a molecular weight of about 6000 daltons. In one example, the polyethylene glycol has a molecular weight of at least about 2000 daltons. In another example, the polyethylene glycol has a molecular weight of at least about 3000 daltons. In another example, the polyethylene glycol has a molecular weight of at least about 4000 daltons. In another example, the polyethylene glycol has a molecular weight of at least about 5000 daltons. In another example, the polyethylene glycol has a molecular weight of at least about 6000 daltons.

In one embodiment, the thermosoftening carrier is selected from PEG6000, poloxamer 188, and combinations thereof.

The phrase "poly(alkylene glycol)" or "polyalkylene glycol", as used herein, encompasses a family of polyether polymers which share the following general formula:

—O—[(CR$_2$)m-O—]n-, wherein each R is independently hydrogen or alkyl, m represents the number of carbon atoms in the backbone of the polymer in each alkylene glycol unit, and n represents the number of repeating units.

For example, when m=2 and R is hydrogen, the polymer is referred to as a polyethylene glycol. When m=3 and R is hydrogen, or when m=2 and one R in each unit is methyl (and the other R groups are hydrogen), the polymer is referred to as a polypropylene glycol.

In some embodiments, m is an integer greater than 1 (e.g., m=2, 3, 4, etc.).

Optionally, m varies among the units of the poly(alkylene glycol) chain. For example, a poly(alkylene glycol) chain may comprise both ethylene glycol and propylene glycol units linked together.

The thermosoftening carrier may also be a polyalkylene glycol derivative. The phrase "polyalkylene glycol derivative" refers herein to a polyalkylene glycol as defined herein, of which at least a portion (e.g., 1-50%) is modified so as to include moieties other than an alkylene glycol, as defined herein. In some embodiments, a polyalkylene glycol derivative is a polyalkylene glycol modified at one or both termini thereof so as to include additional moieties. Exemplary polyalkylene glycol derivatives which are suitable for use in the context of embodiments of the invention include, without limitation, polyalkylene glycol glycerides, such as Gelucires™ (e.g., Gelucire 40/01™)) and tocopherol polyethylene glycol succinate.

The thermosoftening carrier may also comprise an oil or a combination of one or more oils. Many oils suitable for use as a thermosoftening carrier for therapeutic applications are known in the art. Examples include, without limitation, esters of fatty acids, such as triglycerides and diesters of a glycol (e.g., propylene glycol). Other oils may be added to the thermosoftening carrier to decrease/fine tune viscosity, e.g., fractioned coconut oil or soybean oil.

As exemplified in the Examples section herein, the use of a thermosoftening carrier in a liquid fill capsule prevented cracking and leakage of the capsules, but was associated with non-homogeneity of the liquid fill composition used to fill the capsules.

Anti-Adherent Agent

As further described hereinabove and exemplified in the Examples section that follows, the present inventors have surprisingly uncovered that the homogeneity of batches of capsules containing oxidized phospholipids (e.g., VB-201, VB-208, VB-221, or VB-219) can be considerably improved by mixing the oxidized phospholipid (e.g., VB-201, VB-208, VB-221, or VB-219) with an anti-adherent agent.

Hence, according to some embodiments of the invention, the solid or semi-solid matrix further comprises an anti-adherent agent.

It is to be appreciated that inclusion of anti-adherent agents in liquid fill compositions of capsules has not been suggested nor practiced heretofore. It is to be further appreciated that typically, when utilizing liquid fill techniques for encapsulation, a problem of adherence does not arise.

As used herein, the phrase "anti-adherent agent" refers to an agent which reduces the cohesion between particles of a substance (e.g., VB-201, VB-208, VB-221, or VB-219) and/or an adherence of such particles to a solid surface (e.g., of a container and/or encapsulation machinery). For example, the reduction of cohesion caused by an anti-adherent agent is greater than a reduction of cohesion caused by mere dilution of the substance by addition of an agent.

Optionally, the anti-adherent agent is a material (e.g., a solid, such as a powder) with little or no solubility in the other components of the capsule (e.g., the thermosoftening carrier). The anti-adherent agent may act by adhering to the oxidized phospholipid (e.g., VB-201, VB-208, VB-221, or VB-219) e.g., VB-201, VB-208, VB-221, or VB-219 thereby forming, e.g., grains and/or powder particles. As a result, the adherence of the oxidized phospholipid (e.g., VB-201, VB-208, VB-221, or VB-219) to other surfaces (e.g., other VB-201 grains and/or powder particles, surfaces of containers and/or encapsulation machinery) is reduced.

It is to be appreciated that the use of a material with little or no solubility to increase homogeneity in a liquid fill composition is novel and surprising, as insoluble materials typically increase inhomogeneity (e.g., by sedimentation, coagulation) in a liquid, and would therefore not be expected to increase homogeneity.

Without being bound to any particular theory, it is suggested that the anti-adherent agent results in the formation of uniform dispersion of grains and/or powder particles of the oxidized phospholipid (e.g., VB-201, VB-208, VB-221, or VB-219) that are adhered to the anti-adherent agent.

Examples of anti-adherent agents include, but are not limited to, talc, magnesium stearate, cellulose (e.g., microcrystalline cellulose), cellulose derivatives (e.g., hydroxypropyl methylcellulose (HPMC)), lactose, gelatin, alginates, aluminium hydroxide, magnesium oxide, clays, attapulgite, bentonite, carrageenan, copovidone, hectorite, polymethacrylates, sodium docusate, erythritol, povidones, croscarmellose sodium, dextrates, starches, iron oxide, kaolin, silicates (e.g., magnesium aluminium silicate), corn flour, sugars, calcium carbonate, magnesium carbonate, calcium phosphate, calcium sulfate, bicarbonates (e.g., of potassium or sodium), citrate salts (e.g., potassium citrate) and titanium dioxide.

As exemplified in the Examples section, talc is an example for an effective anti-adherent agent.

In one example, the weight ratio of the anti-adherent agent to the oxidized phospholipid (e.g., VB-201, VB-208, VB-221, or VB-219), e.g., in the pharmaceutical composition (i.e., liquid-fill composition), is in a range of from about 1:5 to about 5:1 (anti-adherent agent:oxidized phospholipid). In other examples, the weight ratio of the anti-adherent agent to the oxidized phospholipid (e.g., VB-201, VB-208, VB-221, or VB-219) is in the range from about 1:4 to about 5:1, from about 1:3 to about 5:1, from about 1:2 to about 5:1, or from about 1:1 to about 5:1.

In other examples, the weight ratio of the anti-adherent agent to the oxidized phospholipid (e.g., VB-201, VB-208, VB-221, or VB-219) is from about 1:5 to about 4:1, from about 1:5 to about 3:1, from about 1:5 to about 2:1, or from about 1:5 to about 1:1.

In other examples, the weight ratio of the anti-adherent agent to the oxidized phospholipid (e.g., VB-201, VB-208, VB-221, or VB-219) is from about 1:4 to about 4:1, from about 1:4 to about 3:1, from about 1:4 to about 2:1, or from about 1:4 to about 1:1.

In other examples, the weight ratio of the anti-adherent agent to the oxidized phospholipid (e.g., VB-201, VB-208, VB-221, or VB-219) is from about 1:3 to about 4:1, from about 1:3 to about 3:1, from about 1:3 to about 2:1, or from about 1:3 to about 1:1.

In other examples, the weight ratio of the anti-adherent agent to the oxidized phospholipid (e.g., VB-201, VB-208, VB-221, or VB-219) is from about 1:2 to about 4:1, from about 1:2 to about 3:1, from about 1:2 to about 2:1, or from about 1:2 to about 1:1, or from about 1:2 to about 1.5:1.

In other examples, the weight ratio of the anti-adherent agent to the oxidized phospholipid (e.g., VB-201, VB-208, VB-221, or VB-219) is in the range from about 1:1 to about 5:1, from about 1:1 to about 4:1, from about 1:1 to about 3:1, from about 1:1 to about 2:1, or from about 1:1 to about 1.5:1.

In other examples, the weight ratio of the anti-adherent agent to the oxidized phospholipid (e.g., VB-201, VB-208, VB-221, or VB-219) is about 1:1. In other examples, the weight ratio of the anti-adherent agent to the oxidized phospholipid (e.g., VB-201, VB-208, VB-221, or VB-219) is about 1:2. In other examples, the weight ratio of the anti-adherent agent to the oxidized phospholipid (e.g., VB-201, VB-208, VB-221, or VB-219) is about 1:3. In other examples, the weight ratio of the anti-adherent agent to the oxidized phospholipid (e.g., VB-201, VB-208, VB-221, or VB-219) is about 1:4. In other examples, the weight ratio of the anti-adherent agent to the oxidized phospholipid (e.g., VB-201, VB-208, VB-221, or VB-219) is about 1:5.

Thus, an anti-adherent agent: oxidized phospholipid (e.g., VB-201, VB-208, VB-221, or VB-219) ratio can be, for example, about 1:5, 1:4, 1:3, 1:2, 1:1, 1:1.2, 1:1.4, 1:1.5, 1:1.6, 1:1.8, 1.2:1, 1.4:1, 1.5:1, 1.6:1, 1.8:1, 2:1, 2.5:1, 3:1, 3.5:1, 4:1, 4.5:1, or 5:1. Other ratio values are also contemplated.

In one example according to any of the above embodiments, the anti-adherent agent is talc. In another example according to any of the above embodiments, the anti-adherent agent is talc and the oxidized phospholipid is VB-201. For example, the oxidized phospholipid (e.g., VB-201, VB-208, VB-221, or VB-219) is milled with an equal amount of talc (1:1 weight ratio). In another example, the oxidized phospholipid (e.g., VB-201, VB-208, VB-221, or VB-219) is milled with talc in a talc:oxidized phospholipid weight ratio of about 1:2, about 1:3, about 1:4, or about 1:5. In other examples, the oxidized phospholipid (e.g., VB-201, VB-208, VB-221, or VB-219) is milled with talc in a talc:oxidized phospholipid weight ratio of about 2:1, about 3:1, or about 4:1.

The inventors have recognized that the weight ratio of the anti-adherent agent to the oxidized phospholipid has an effect on the homogeneity (i.e., a sufficient dose content uniformity), e.g., with respect to the distribution of the oxidized phospholipid in the thermsoftening carrier or the final composition, and/or on the long-term stability of the final formulation. Hence, in some embodiments, the anti-adherent agent to oxidized phospholipid (e.g., VB-201, VB-208, VB-221, or VB-219) weight ratio is about 1:1 or less (e.g., 1:2 or less, or 1:3 or less).

In other embodiments, the anti-adherent agent to oxidized phospholipid (e.g., VB-201, VB-208, VB-221, or VB-219) weight ratio is about 1:1.1, 1:1.2, 1:1.3, 1:1.4, 1:1.5, 1:1.6, 1:1.7, 1:1.8, 1:1.9, or about 1:2. In some embodiments, the anti-adherent agent to oxidized phospholipid (e.g., VB-201, VB-208, VB-221, or VB-219) weight ratio is about 1:2 or less.

In other embodiments, the anti-adherent agent to oxidized phospholipid (e.g., VB-201, VB-208, VB-221, or VB-219) ratio is at least about 1:1, at least about 2:1, at least about 3:1, at least about 4:1, or at least about 5:1. For example, in the case of VB-201, a ratio of at least about 1:2 (e.g., at least about 1:1) was associated with satisfactory dose content uniformities.

Optionally, a ratio of an amount of anti-adherent agent to an amount of VB-201 in the capsule is in a range of from 1:3 to 5:1 (anti-adherent agent:VB-201), and optionally from 1:2 to 3:1. Thus, an anti-adherent agent:VB-201 ratio can be, for example, 1:3, 1:2, 1:1.5, 1:1.2, 1:1, 1.2:1, 1.5:1, 2:1, 2.5:1, 3:1, 4:1 or 5:1. Other ratio values are also contemplated.

In exemplary embodiments the anti-adherent agent to VB-201 ratio is about 1:1.

Herein, ratios of anti-adherent agent to oxidized phospholipid (e.g., VB-201, VB-208, VB-221, or VB-219) refer to weight ratios.

In some embodiments, the concentration of the anti-adherent agent in the pharmaceutical composition (i.e., matrix) is in a range of from about 1 to about 50 weight percent, from about 1 to about 40 weight percent, or about 1 to about 30 weight percent, optionally from about 2 to about 25 weight percent, and optionally from about 3 to about weight percent. Such percentages of anti-adherent agent may optionally correspond to a ratio of anti-adherent agent to oxidized phospholipid (e.g., VB-201, VB-208, VB-221, or VB-219) as described herein. In some embodiments, the concentration of the anti-adherent agent in the pharmaceutical composition (i.e., matrix) is in a range of from about 2 to about 20 weight percent, from about 2 to about 15 weight percent, from about 2 to about 10 weight percent, or from about 2 to about 5 weight percent. In other embodiments, the concentration of the anti-adherent agent in the pharmaceutical composition (i.e., matrix of the capsule) is in a range of from about 1 to about 20 weight percent, from about 1 to about 10 weight percent, or from about 1 to about 5 weight percent. In some embodiments, the concentration of the anti-adherent agent in the pharmaceutical composition (i.e., matrix) is in a range of from about 5 to about 40 weight percent, from about 5 to about 30 weight percent, from about 5 to about 20 weight percent, or from about 5 to about 15 weight percent. In other embodiments, the concentration of the anti-adherent agent in the pharmaceutical composition (i.e., matrix of the capsule) is in a range of from about 7 to about 15 weight percent.

Talc

In one example according to any of the above embodiments, the anti-adherent agent is talc. Any pharmaceutical-grade or food-grade talc (e.g., powdered talc) may be used. Exemplary grades of talc, which can be used in the pharmaceutical compositions, liquid-fill compositions, capsules and other are embodiments herein are disclosed in Dawoodbhai et al., "Pharmaceutical and Cosmetic Uses of Talc," Drug Development and Industrial Pharmacy, 16(16):2409-2429 (1990); and Dawoodbhai et al., "Glidants and Lubricant Properties of Several Types of Talcs," Drug Development and Industrial Pharmacy, 13(13):2441-2467 (1987), each of which is incorporated herein by reference in its entirety. In some examples, the talc is powdered talc. In some examples, the talc is of USP grade. In other example, the talc is powdered talc and of USP grade.

Thixotropic Agent

In some embodiments, the pharmaceutical composition or the capsule of the present disclosure further includes a thixotropic agent (also referred to herein as a thixotrop), a gelling agent, or a combination thereof. In some embodiments, the pharmaceutical composition or the capsule of the present disclosure further includes a thixotropic agent. As exemplified in the Examples section that follows, inclusion of a thixotropic agent (e.g., fumed silica) in capsules results in capsules having a greater uniformity of oxidized phospholipid (e.g., VB-201, VB-208, VB-221, or VB-219) content.

Without being bound by any particular theory, it is believed that the increase in viscosity of the fill composition, which is caused by the thixotropic agent, prevents separation of ingredients of the fill composition (e.g., VB-201, VB-208, VB-221, or VB-219 and/or talc) from the carrier before a solid or semi-solid matrix is formed, thereby increasing homogeneity of the fill composition.

Hence, according to some embodiments, the matrix further comprises an agent which increases the viscosity of the thermosoftening carrier softened by heating (e.g., a molten carrier), such as a thixotropic agent and/or a gelling agent. In one example, the thixotropic agent and/or gelling agent is capable of increasing the viscosity of the pharmaceutical composition (i.e., a fill composition) at a temperature at which the fill composition is prepared (e.g., at the temperature to which the fill composition is heated prior to filling into a capsule (e.g., the agent should not decompose at such a temperature).

As used herein, a "gelling agent" refers to an agent which forms a gel when added to a liquid.

As used herein, a "thixotropic agent" refers to an agent which increases a viscosity of a liquid when added to a liquid. As known in the art "thixotropy" is a reversible behaviour of viscous liquids (e.g., gels) that liquefy when subjected to shear stress such as shaking or stirring, or otherwise disturbed.

A viscous liquid containing a thixotropic agent exhibits thixotropy, wherein the viscosity is reduced under stress (e.g., stirring, heating and/or application of shear forces). The ingredients in a liquid fill composition (e.g., carrier, VB-201, thixotropic agent, and/or anti-adherent agent) can therefore be readily mixed by stirring, as the viscosity is reduced during stirring, yet the fill composition is relatively resistant to separation of components, as the viscosity increases when stirring ceases.

Examples of thixotropic agents suitable for use in the context of the present embodiments include, but are not limited to, fumed silica (available, for example as Aerosils® and Cab-O-Sil® products), kieselguhr, gums (e.g., xanthan gum, guar gum, locust bean gum, alginates), cellulose derivatives (e.g., hydroxypropyl methyl cellulose), starches, polymers (e.g., polyvinyl alcohol, polyacrylates, hydrophobically-modified polyacrylates), emulsifiers, and clay derivatives (e.g., amine treated magnesium aluminum silicate, bentonite colloidal silicic acid, white smectite clays and bleaching earth, attapulgite, mica, synthetic magnesium phyllosilicates (Laponite), layered silicates, modified smectites, hectorite, and sepiolite. Optionally, the thixotropic agent comprises fumed silica and/or attapulgite.

The concentration of the thixotropic agent in the pharmaceutical composition (i.e., liquid-fill composition or matrix of the capsule) unless otherwise indicated is determined relative to the combined weight of the thermosoftening carrier and the thixotropic agent. For example, at 2.5 weight percent of thixotropic agent, the pharmaceutical composition may contain 10 mg thixotropic agent and 390 mg of a thermosoftening carrier (10/400=2.5%).

In some embodiments, the concentration of the thixotropic agent is from about 0.1 weight percent to about 10 weight percent, or from about 0.25 to 10 weight percent, or from about 0.5 weight percent to about 5 weight percent, or from about 0.5 weight percent to about 4 weight percent, or from about 0.5 weight percent to about 3 weight percent, or from about 1 weight percent to about 10 weight percent, or from about 1 weight percent to about 5 weight percent, or from about 1 weight percent to about 4 weight percent, or from about 1 weight percent to about 3 weight percent, optionally from about 2 weight percent to about 3 weight percent.

In one example according to any of the above embodiments, the thixotropic agent is a different substance than the thermosoftening agent (i.e., the thixotropic agent is chemically distinct from the thermosoftening agent). In another example according to any of the above embodiments, the thixotropic agent is a different substance than the anti-adherent agent (i.e., the thixotropic agent is chemically distinct from the anti-adherent agent). In other examples according to any of the above embodiments, the thixotropic agent is a different substance than the thermosoftening agent and the anti-adherent agent (i.e., the thixotropic agent is chemically distinct from both the thermosoftening agent and the anti-adherent agent).

Unit Dosage Forms

The pharmaceutical compositions or fill-compositions of the current disclosure may be used to produce unit dosage forms (e.g., capsules) comprising a certain amount of active ingredient. In some embodiments, the current disclosure provides a unit dosage form comprising from about 1 mg to about 100 mg of active pharmaceutical ingredient.

The active pharmaceutical ingredient is selected from oxidized phospholipids described herein and combinations thereof. Hence, in some embodiments, the current disclosure provides a unit dosage form comprising from about 1 mg to about 100 mg of oxidized phospholipid (e.g., VB-201, VB-208, VB-219, or VB-221), or from about 10 mg to about 100 mg of oxidized phospholipid, or from about 20 mg to about 100 mg of oxidized phospholipid, or from about 20 mg to about 80 mg of oxidized phospholipid.

In one example according to any of the above embodiments, the active pharmaceutical ingredient is VB-201. Hence, in some embodiments, the current disclosure provides a unit dosage form comprising from about 1 mg to about 100 mg of VB-201, or from about 10 mg to about 100 mg of VB-201, or from about 20 mg to about 100 mg of VB-201, or from about 20 mg to about 80 mg of VB-201.

In some embodiments, the unit dosage form is a capsule. Accordingly, in some embodiments, a capsule as described herein comprises from about 1 mg to about 100 mg of oxidized phospholipid (e.g., VB-201, VB-208, VB-221, or VB-219) per capsule, or about 10 mg to about 100 mg of oxidized phospholipid per capsule, or from about 20 mg to about 100 mg of oxidized phospholipid per capsule, or from about 20 mg to about 80 mg of oxidized phospholipid per capsule. According to some embodiments, a capsule as described herein comprises from about 1 mg to about 100 mg of VB-201 per capsule, or from about 10 mg to about 100 mg of VB-201 per capsule, or from about 20 mg to about 80 mg of VB-201 per capsule.

According to other embodiments of the present disclosure, a capsule as described herein comprises about 20 mg of oxidized phospholipid. In some embodiments, a capsule as described herein comprises about 20 mg of VB-201. According to other embodiments, a capsule as described herein comprises about 40 mg of oxidized phospholipid. In some embodiments, a capsule as described herein comprises about 40 mg of VB-201. According to other embodiments, a capsule as described herein comprises about 80 mg of oxidized phospholipid. In some embodiments, a capsule as described herein comprises about 80 mg of VB-201.

According to some embodiments, a capsule as described herein comprises about 100 mg of oxidized phospholipid. In some embodiments, a capsule as described herein comprises about 100 mg of VB-201. Capsules containing higher amounts of oxidized phospholipids (e.g., VB-201, VB-208, VB-221, or VB-219), e.g., about 110 mg, about 120 mg, about 130 mg, about 140 mg, about 150 mg, or about 200 mg are also contemplated. It is noted however that higher amounts of oxidized phospholipid (e.g., VB-201, VB-208, VB-221, or VB-219) may require larger capsules.

According to some embodiments, a capsule as described herein comprises oxidized phospholipid from about 0.1 weight percent to about 25 weight percent of the total weight of the fill composition or matrix, and optionally from about 1 weight percent to about 25 weight percent. In some embodiments, a capsule comprises oxidized phospholipid from about 2 weight percent to about 23 weight percent of the total weight of the fill composition or matrix. In other embodiments, a capsule comprises oxidized phospholipid from about 4 weight percent to about 18 weight percent of the total weight of the fill composition or matrix.

In other embodiments, a capsule comprises oxidized phospholipid from about 4 weight percent to about 5 weight percent of the total weight of the fill composition or matrix. In other embodiments, a capsule comprises oxidized phospholipid from about 8 weight percent to about 9 weight percent of the total weight of the fill composition or matrix. In other embodiments, a capsule comprises oxidized phospholipid from about 14 weight percent to about 17 weight percent of the total weight of the fill composition or matrix.

According to some embodiments, a capsule as described herein comprises from about 0.1 weight percent to about 25 weight percent of VB-201, and optionally from about 1 weight percent to about 25 weight percent of VB-201 relative to the total weight of the fill composition or matrix. In some embodiments, a capsule comprises from about 2 weight percent to about 23 weight percent of VB-201 in the fill composition or matrix. In other embodiments, a capsule comprises from about 4 weight percent to about 18 weight percent of VB-201 in the fill composition or matrix.

In some embodiments, a capsule comprises oxidized phospholipid at a concentration of about 4.5 weight percent of the total weight of the fill composition. In some embodiments, a capsule comprises VB-201 at a concentration of about 4.5 weight percent of the total weight of the fill composition.

In some embodiments, a capsule comprises oxidized phospholipid at a concentration of about 8 weight percent of the total weight of the fill composition. In some embodiments, a capsule comprises VB-201 at a concentration of about 8 weight percent of the total weight of the fill composition. In some embodiments, a capsule comprises VB-201 at a concentration of about 9 weight percent of the total weight of the fill composition.

In some embodiments, a capsule comprises oxidized phospholipid at a concentration of about 14 weight percent of the total weight of the fill composition. In some embodiments, a capsule comprises VB-201 at a concentration of about 14 weight percent of the total weight of the fill composition. In some embodiments, a capsule comprises VB-201 at a concentration of about 17 weight percent of the total weight of the fill composition. In some embodiments, a capsule comprises VB-201 at a concentration of about 18 weight percent of the total weight of the fill composition.

In some embodiments, a capsule comprises VB-201 at a concentration of about 23 weight percent of the total weight of the fill composition.

In some embodiments, a capsule comprises VB-201 at a concentration of about 28 weight percent of the total weight of the fill composition.

Additional Components of the Compositions

The pharmaceutical compositions, fill-compositions or capsule matrices described herein may optionally further include additional chemical components, including, but not limited to, excipients, lubricants, buffering agents, antibacterial agents, bulking agents (e.g. mannitol), antioxidants (e.g., ascorbic acid or sodium bisulfite), and the like. Herein the term "excipient" refers to an inert substance added to a pharmaceutical composition to further facilitate administration of an active ingredient. These or other ingredients can be contained in the shell of the capsule.

As exemplified in the Examples section that follows, the capsules may be coated with a coating (e.g., an enteric coating). Any such coating known in the art is contemplated. Suitable materials for forming a coating include, but are not limited to, Eudragit®, Opadry® (e.g., Opadry® AMB) and Acryl-Eze®, which may be used alone or in combination to form an enteric coating.

Exemplary excipients and techniques for formulation and administration of drugs may be found in "Remington's Pharmaceutical Sciences" Mack Publishing Co., Easton, Pa., latest edition, which is incorporated herein by reference in its entirety.

Processes

As exemplified in the Examples section, the inventors have developed a process for encapsulation of oxidized phospholipids (e.g., VB-201, VB-208, VB-221, or VB-219) which provides liquid fill capsules with excellent content uniformity and which do not deteriorate upon storage (e.g., by leakage or cracking).

Thus, in some embodiments, the present disclosure provides a process for producing a pharmaceutical composition comprising a thermosoftening carrier and an oxidized phospholipid having a structure according to Formula (I):

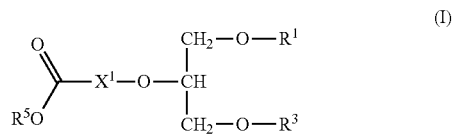

wherein $R^1$, $R^3$, $R^5$, and $X^1$ are defined as for Formula (I) herein above. The process comprises heating said thermosoftening carrier to a temperature above the melting point of the thermosoftening carrier, and contacting the oxidized phospholipid with the thermosoftening carrier, to thereby obtain said pharmaceutical composition.

Oxidized phospholipids useful in the above process are selected from those described herein. In some embodiments, the oxidized phospholipid in the above process can have a structure according to Formula (II) or Formula (II) as described hereinabove. In one example, the oxidized phospholipid is VB-201.

The thermosoftening carrier useful in the above process is selected from those described herein. In some examples according to any of the above embodiments, the thermosoftening carrier has a melting point from about 40° C. to about 100° C. In other examples according to any of the above embodiments, the thermosoftening carrier is selected from a polyalkylene glycol, a polyalkylene glycol derivative, and a wax. In some examples according to any of the above embodiments, the thermosoftening carrier is a member selected from polyethylene glycol, polypropylene glycol, and copolymers thereof. In other examples according to any of the above embodiments, the thermosoftening carrier is a poloxamer. In other examples according to any of the above embodiments, the poloxamer has a molecular weight from about 2000 to about 18000 daltons. In other examples, the poloxamer has a molecular weight from about 7000 to about 10000 daltons. In other examples, the poloxamer comprises from about 40 to about 90 weight percent of polyethylene glycol. In other examples, the poloxamer is poloxamer 188 (i.e., Lutrol F68).

In other examples according to any of the above embodiments, the thermosoftening carrier is polyethylene glycol, e.g., a polyethylene glycol having a molecular weight from about 1500 to about 8000 daltons, or about 6000 daltons.

In some embodiments the above process further comprises milling, grinding or mixing the oxidized phospholipid (e.g., VB-201, VB-208, VB-221, or VB-219) with an anti-adherent agent, e.g., prior to contacting the oxidized phospholipid (e.g., VB-201, VB-208, VB-221, or VB-219) with the thermosoftening carrier.

The anti-adherent agent useful in the above process can be any anti-adherent agent known in the art and may be selected from those described herein. In some examples according to the above embodiment, the anti-adherent agent is selected from talc, magnesium stearate, cellulose, cellulose derivatives, lactose, gelatin, alginates, aluminium hydroxide, magnesium oxide, clays, attapulgite, bentonite, carrageenan, copovidone, hectorite, polymethacrylates, sodium docusate, erythritol, povidones, croscarmellose sodium, dextrates, starches, iron oxide, kaolin, silicates, corn flour, sugars, calcium carbonate, magnesium carbonate, calcium phosphate, calcium sulfate, bicarbonates, citrate salts, and titanium dioxide. In some examples according to any of the above embodiments, the anti-adherent agent is talc.

In some examples according to any of the above embodiments, the anti-adherent agent is milled with the oxidized phospholipid in a weight ratio as described herein (see section "Anti-Adherent Agent") e.g., from about 1:5 to about 5:1, from about 1:4 to about 2:1, or from about 1:4 to about 1:1. In some examples, the final concentration of the anti-adherent agent in the pharmaceutical composition is from about 1 to about 30 weight percent. Other exemplary anti-adherent agent:oxidized phospholipid weight ratios are described herein.

In some examples according to any of the above embodiments, the above process further comprises admixing the thermosoftening carrier with a thixotropic agent, a gelling agent, or a combination thereof. In some examples according to any of the above embodiments, the above process further comprises admixing the thermosoftening carrier with a thixotropic agent, e.g., prior to contacting the thermosoftening carrier with the oxidized phospholipid. In some examples according to any of the above embodiments, the thixotropic agent is a fumed silicon dioxide (also referred to as fumed silica). In some examples according to any of the above embodiments, the thixotropic agent is Aerosil 200.

In some examples according to any of the above embodiments, the concentration of the thixotropic agent (relative to the combined weight of the thermosoftening carrier and the thixotropic agent) is from about 0.25 weight percent to about 10 weight percent. Other useful weight percentages are described herein.

In some embodiments, the above process further comprises filling the pharmaceutical composition into a capsule shell to thereby form a capsule. In some examples, the filling is performed at a temperature above the melting point of the thermosoftening carrier and the pharmaceutical composition forms a solid or semi-solid matrix upon cooling below the melting point of the thermosoftening carrier. In some examples, the capsule comprises a shell material selected from the group consisting of gelatin, pullulan, starch, and hydroxypropyl methyl cellulose (HPMC). In other examples, the shell material is gelatin.

In one example according to any of the above embodiments of the above described process, the oxidized phospholipid is VB-201.

In some embodiments, the current disclosure provides a liquid-fill capsule prepared by the above process or any of its embodiments and examples. According to other embodiments of the present disclosure there is provided a process of producing a liquid fill composition which comprises an oxidized phospholipid (e.g., VB-201, VB-208, VB-221, or VB-219), the process comprising contacting (e.g., mixing) the oxidized phospholipid (e.g. VB-201) with a thermosoftening carrier (e.g., a carrier as described herein) at a temperature above room temperature, as described herein. Optionally, the process further comprises adding an anti-adherent agent. For example, the process may further include mixing (e.g., milling) the oxidized phospholipid with an anti-adherent agent, e.g., prior to contacting the oxidized phospholipid with the thermosoftening carrier. The process can further include adding a thixotropic agent. For example, the process may further include admixing the thermosoftening carrier with a thixotropic agent, a gelling agent, or a combination thereof, e.g., prior to contacting the oxidized phospholipid (e.g., which has been milled with the anti-adherent agent) with the thermosoftening carrier.

According to some embodiments the present disclosure provides a process of producing a liquid fill capsule comprising an oxidized phospholipid (e.g., VB-201). In one embodiment, the process comprises filling a capsule shell with a liquid fill composition (e.g., a composition as described herein) which comprises an oxidized phospholipid (e.g., VB-201, VB-208, VB-221, or VB-219) and a thermosoftening carrier as described herein (e.g., a polyalkylene glycol described herein). Optionally, the filling is performed at a temperature above room temperature (e.g., at least 40° C., at least 50° C., at least 60° C.), and the liquid fill composition forms a solid or semi-solid matrix upon being cooled to room temperature.

In some examples according to any of the above embodiments, the capsule shell optionally comprises gelatin, HPMC, pullulan, starch and/or any shell material described herein.

In some embodiments, the process further comprises contacting (e.g., mixing) the oxidized phospholipid (e.g., VB-201, VB-208, VB-221, or VB-219) (e.g., granulated VB-201 or powdered VB-201) with the thermosoftening carrier to obtain the liquid fill composition. The thermosoftening carrier is optionally heated so as to soften the carrier (e.g., by melting) prior to mixing the oxidized phospholipid (e.g., VB-201, VB-208, VB-221, or VB-219) with the thermosoftening carrier.

In some embodiments, the process further comprises mixing (e.g., milling or grinding) the oxidized phospholipid (e.g., VB-201, VB-208, VB-221, or VB-219) with an anti-adherent agent (e.g., an anti-adherent agent as described herein) prior to contacting (e.g., mixing) the oxidized phospholipid (e.g., VB-201, VB-208, VB-221, or VB-219) with the thermosoftening carrier. The oxidized phospholipid (e.g., VB-201, VB-208, VB-221, or VB-219) and the anti-adherent agent may be mixed in any weight ratio described herein, for example in a ratio from about 1:3 to about 5:1 anti-adherent agent:oxidized phospholipid (e.g., VB-201, VB-208, VB-221, or VB-219). Optionally, the oxidized phospholipid (e.g., VB-201, VB-208, VB-221, or VB-219) and the anti-adherent agent are in powder form, and are mixed to form a powder blend, or are milled together to form a powder-blend.

Mixing the oxidized phospholipid (e.g., VB-201, VB-208, VB-221, or VB-219) and the anti-adherent agent may be accomplished according to any suitable method known in the art. Optionally, the mixing is performed by a method selected so as to provide a homogeneous mixture (e.g., a homogeneous powder blend). In an exemplary method, the oxidized phospholipid (e.g. VB-201) and the anti-adherent agent are ground or milled together to form a homogeneous powder blend. In some examples according to any of the above embodiments, the oxidized phospholipid (e.g. VB-201) and the anti-adherent agent are ground or milled using a mill/grinder that is suitable to minimize a potential temperature increase of the material being ground. Suitable machines include bladed grinders, such as those that work on the principle of rapidly rotating blades (e.g., about 9000 rpm at full speed). An exemplary mill is the Fitzpatrick mill. Ideally, the mill is equipped with an output sieve or screen for retaining any oversize remnant of the grinding process. The screen can have various mesh sizes. In some examples according to any of the above embodiments, the screen has from about 20 mesh to about 80 mesh, or from about 30 mesh to about 80 mesh, or from about 40 mesh to about 80 mesh, or from about 40 mesh to about 60 mesh or about 50 mesh.

The mixture of the oxidized phospholipid (e.g., VB-201, VB-208, VB-221, or VB-219) and the anti-adherent agent is then contacted with or combined with (e.g., added to) the thermosoftening carrier (e.g., molten carrier) to form a composition at an amount which provides a desired concentration (e.g., a concentration described herein) of the oxidized phospholipid (e.g., VB-201, VB-208, VB-221, or VB-219) and/or anti-adherent agent in the fill composition.

Alternatively, the anti-adherent agent is combined with (e.g., added to) the thermosoftening carrier so as to form a mixture and then the oxidized phospholipid (e.g., VB-201, VB-208, VB-221, or VB-219) is combined with (e.g., added to) the mixture.

Optionally, a final concentration of the anti-adherent agent in the composition is in a range of from about 1 to about 30 weight percent, optionally from about 2 to about 25 weight percent, and optionally from about 3 to about 20 weight percent. Such percentages of anti-adherent agent may optionally correspond to a ratio of anti-adherent agent to oxidized phospholipid (e.g., VB-201, VB-208, VB-221, or VB-219) described herein.

According to optional embodiments, the process further comprises adding a thixotropic gel and/or gelling agent (e.g., an agent described herein) to the other ingredients of the fill composition, such that the fill composition comprises a thixotropic gel and/or gelling agent. The thixotropic gel and/or gelling agent may be mixed with VB-201 and/or with the carrier at any stage of the process, for example, prior to mixing of VB-201 with the carrier, concurrently with mixing of VB-201 with the carrier, and/or subsequently to mixing of VB-201 with the carrier. In an exemplary embodiment, the thixotropic gel and/or gelling agent is added to the carrier prior to mixing of VB-201 with the carrier.

Optionally, the thixotropic agent is added to the composition to obtain a final concentration of thixotropic agent as described herein, for example, a final concentration of thixotropic agent in a range of from 0.25 weight percent to 10 weight percent.

The ingredients of the fill composition (e.g., VB-201, carrier, anti-adherent agent, thixotropic gel and/or gelling agent) may be mixed in amounts and proportions, so as to obtain a fill composition suitable for filling a capsule with any final amount and/or concentration of ingredient described herein.

Mixing the ingredients can be performed by utilizing any technique known in the art, including, for example, a high shear mixer, a paddle mixer, a blender, a ribbon blender, a double cone blender, a planetary mixer, a static mixer, and sonication.

According to other embodiments of the current disclosure, there is provided a liquid fill capsule prepared according to the process described herein, for example, using a liquid fill composition as described herein.

Filling of Capsules

Filling of the capsules with the fill composition and encapsulating the composition so as to obtain a capsule as described herein may be performed according to any method known in the art.

Various designs of hard shell capsules are known in the art, and can be used in embodiments of the present invention. Techniques for filling capsules of any given design will be known to one of skill in the relevant art.

The following describes an exemplary method of obtaining the capsule. Empty capsules are generally supplied to the filling machine in a "prelocked" condition, wherein the capsule body has a cap which is loosely attached thereto. Generally, a series of rings or protrusions are provided in the mating surfaces of the cap or body which enable the cap to be loosely attached to the body so that the cap and body are held together during storage but enabling the cap to be removed prior to filling of the capsule. Once the capsule has been filled, the cap is replaced and forced beyond the prelocked position into a fully locked position. Alternatively, other types of capsule filling machines are designed to accept separate supplies of capsule bodies and caps.

The capsules are closed at high speed after filling and, although most have some form of air vent in their cap or body design, this may not be totally effective at normal filling speeds in eliminating the trapping of air or other gas within the capsule, thereby leaving the filled capsule in a pressurized state (e.g. up to 1 bar) until the pressure equilibrates with the exterior.

During closure of the capsule, the cap is fitted over the body and the body is pushed up until it locks on the cap. The cap is close fitting and normally approximately half the length of the body, so it travels for a considerable distance down the capsule body before locking. This has the effect of a piston in trapping and pressurizing the capsule. The excess gas normally escapes through the gap between the cap and the body, and vents may be provided in this region so as to facilitate the escape of excess pressure. Alternatively, the capsule may utilize a particularly tight locking mechanism rather than vents (e.g., as in Capsugel Licaps® capsules).

In some embodiments, the capsule is banded by applying a band of polymer solution around the junction between cap and body. The polymer solution is optionally a solution of the same polymer as the capsule cap and/or body in a solvent therefor. Banding is particularly suitable, for example, for providing a smooth capsule surface for coating, which prevents movement between the cap and body of the capsule (which would break the coating).

In cases where the capsule is filled with a molten liquid which sets to a solid state prior to administration, the filling is optionally performed under conditions such that the solid state in the capsule in the capsule is in a predetermined shape (e.g., a plug shape). A predetermined shape may enhance the predictability of a release profile for the pharmaceutically active agent contained therein.

Packaging and Kits

Optionally, the capsules are packaged in a packaging material and identified for use, in or on the packaging material, for use in the treatment of a disease or disorder, e.g., an inflammatory disease or disorder.

Capsules according to the present embodiments may, if desired, be presented in a pack or dispenser device, such as an FDA (the U.S. Food and Drug Administration) approved kit, which may contain one or more capsules containing the oxidized phospholipid (e.g., VB-201, VB-208, VB-221, or VB-219). The pack or dispenser device may, for example, comprise metal or plastic foil, such as, but not limited to a blister pack. The pack or dispenser device may be accompanied by instructions for administration. The pack may also be accompanied by a notice associated with the container in a form prescribed by a governmental agency regulating the manufacture, use or sale of pharmaceuticals, which notice is reflective of approval by the agency of the form of the compositions for human administration. Such notice, for example, may be of labeling approved by the U.S. Food and Drug Administration for prescription drugs or of an approved product insert. Capsules may also be prepared, placed in an appropriate container, and labeled for treatment of an inflammatory disease or disorder, as defined herein.

Methods of Treatment

According to some embodiments, the pharmaceutical compositions, fill-compositions and capsules described herein are for use in the treatment of an inflammatory disease or disorder.

The present disclosure further provides a method of treating an inflammatory disease or disorder, comprising administering (e.g., orally) to a subject in need thereof a pharmaceutical composition of the present disclosure, i.e., a pharmaceutical composition comprising an oxidized phospholipid (e.g., VB-201, VB-208, VB-219, or VB-221), a thermosoftening carrier, and optionally an anti-adherent agent as described herein.

The present disclosure further provides a method of treating an inflammatory disease or disorder, comprising administering (e.g., orally) to a subject in need thereof a capsule which comprises an oxidized phospholipid (e.g., VB-201, VB-208, VB-219, or VB-221), as described herein.

According to optional embodiments, the inflammatory disease or disorder is an inflammatory disease or disorder associated with an endogenous oxidized lipid.

As used herein, the phrase "an endogenous oxidized lipid" refers to one or more oxidized lipids that are present or formed in vivo, as a result of inflammatory and other cell- or humoral-mediated processes. Oxidized low-density lipoprotein (oxidized-LDL) is an example of an endogenous oxidized lipid associated with an inflammatory disease or disorder.

Inflammatory diseases or disorders according to exemplary embodiments of the present invention include psoriasis (e.g., plaque psoriasis), rheumatoid arthritis, and atherosclerosis and related conditions, such as vascular inflammation, i.e., inflammation of an artery (e.g., inflammation of a carotid artery and/or inflammation of an aorta).

Additional examples of inflammatory diseases or disorders according to exemplary embodiments of the present invention include multiple sclerosis and inflammatory bowel disease (e.g., chronic inflammatory bowel disease).

Representative inflammatory diseases and disorders according to embodiments of the present invention include, for example, idiopathic inflammatory diseases or disorders, chronic inflammatory diseases or disorders, acute inflammatory diseases or disorders, autoimmune diseases or disorders, infectious diseases or disorders, inflammatory malignant diseases or disorders, inflammatory transplantation-related diseases or disorders, inflammatory degenerative diseases or disorders, diseases or disorders associated with a hypersensitivity, inflammatory cardiovascular diseases or disorders, inflammatory cerebrovascular diseases or disorders, peripheral vascular diseases or disorders, inflammatory glandular diseases or disorders, inflammatory gastrointestinal diseases or disorders, inflammatory cutaneous diseases or disorders, inflammatory hepatic diseases or disorders, inflammatory neurological diseases or disorders, inflammatory musculoskeletal diseases or disorders, inflammatory renal diseases or disorders, inflammatory reproductive diseases or disorders, inflammatory systemic diseases or disorders, inflammatory connective tissue diseases or disorders, inflammatory tumors, necrosis, inflammatory implant-related diseases or disorders, inflammatory aging processes, immunodeficiency diseases or disorders, proliferative diseases and disorders and inflammatory pulmonary diseases or disorders, as is detailed herein below.

Non-limiting examples of hypersensitivities include Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity, delayed type hypersensitivity, helper T lymphocyte mediated hypersensitivity, cytotoxic T lymphocyte mediated hypersensitivity, TH1 lymphocyte mediated hypersensitivity, and TH2 lymphocyte mediated hypersensitivity.

Non-limiting examples of inflammatory cardiovascular disease or disorder include occlusive diseases or disorders, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune disease or disorder, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease or disorder, and anti-helper T lymphocyte autoimmunity.

Stenosis is an occlusive disease of the vasculature, commonly caused by atheromatous plaque and enhanced platelet activity, most critically affecting the coronary vasculature.

Restenosis is the progressive re-occlusion often following reduction of occlusions in stenotic vasculature. In cases where patency of the vasculature requires the mechanical support of a stent, in-stent-stenosis may occur, re-occluding the treated vessel.

Non-limiting examples of cerebrovascular diseases or disorders include stroke, cerebrovascular inflammation, cerebral hemorrhage and vertebral arterial insufficiency.

Non-limiting examples of peripheral vascular diseases or disorders include gangrene, diabetic vasculopathy, ischemic bowel disease, thrombosis, diabetic retinopathy and diabetic nephropathy.

Non-limiting examples of autoimmune diseases or disorders include all of the diseases caused by an immune response such as an autoantibody or cell-mediated immunity to an autoantigen and the like. Representative examples are chronic rheumatoid arthritis, juvenile rheumatoid arthritis, systemic lupus erythematosus, scleroderma, mixed connective tissue disease, polyarteritis nodosa, polymyositis/dermatomyositis, Sjogren's syndrome, Bechet's disease, multiple sclerosis, autoimmune diabetes, Hashimoto's disease, psoriasis, primary myxedema, pernicious anemia, myasthenia gravis, chronic active hepatitis, autoimmune hemolytic anemia, idiopathic thrombocytopenic purpura, uveitis, vasculitides and heparin induced thrombocytopenia.

Non-limiting examples of inflammatory glandular diseases or disorders include pancreatic diseases or disorders, Type I diabetes, thyroid diseases or disorders, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Non-limiting examples of inflammatory gastrointestinal diseases or disorders include colitis, ileitis, Crohn's disease, chronic inflammatory intestinal disease, inflammatory bowel syndrome, inflammatory bowel disease, celiac disease, ulcerative colitis, an ulcer, a skin ulcer, a bed sore, a gastric ulcer, a peptic ulcer, a buccal ulcer, a nasopharyngeal ulcer, an esophageal ulcer, a duodenal ulcer and a gastrointestinal ulcer.

Non-limiting examples of inflammatory cutaneous diseases or disorders include acne, an autoimmune bullous skin disease, pemphigus vulgaris, bullous pemphigoid, pemphigus foliaceus, contact dermatitis and drug eruption.

Non-limiting examples of inflammatory hepatic diseases or disorders include autoimmune hepatitis, hepatic cirrhosis, and biliary cirrhosis.

Non-limiting examples of inflammatory neurological diseases or disorders include multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease or disorder, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, Huntington's disease, AIDS associated dementia, amyotrophic lateral sclerosis (AML), multiple sclerosis, stroke, an inflammatory retinal disease or disorder, an inflammatory ocular disease or disorder, optic neuritis, spongiform encephalopathy, migraine, headache, cluster headache, and stiff-man syndrome.

Non-limiting examples of inflammatory connective tissue diseases or disorders include autoimmune myositis, primary Sjogren's syndrome, smooth muscle autoimmune disease or disorder, myositis, tendinitis, a ligament inflammation, chondritis, a joint inflammation, a synovial inflammation, carpal tunnel syndrome, arthritis, rheumatoid arthritis, osteoarthritis, ankylosing spondylitis, a skeletal inflammation, an autoimmune ear disease or disorder, and an autoimmune disease or disorder of the inner ear.

Non-limiting examples of inflammatory renal diseases or disorders include autoimmune interstitial nephritis and/or renal cancer.

Non-limiting examples of inflammatory reproductive diseases or disorders include repeated fetal loss, ovarian cyst, or a menstruation associated disease or disorder.

Non-limiting examples of inflammatory systemic diseases or disorders include systemic lupus erythematosus, systemic sclerosis, septic shock, toxic shock syndrome, and cachexia.

Non-limiting examples of infectious disease or disorder include chronic infectious diseases or disorders, a subacute infectious disease or disorder, an acute infectious disease or disorder, a viral disease or disorder, a bacterial disease or disorder, a protozoan disease or disorder, a parasitic disease or disorder, a fungal disease or disorder, a mycoplasma disease or disorder, gangrene, sepsis, a prion disease or disorder, influenza, tuberculosis, malaria, acquired immunodeficiency syndrome, and severe acute respiratory syndrome.

Non-limiting examples of inflammatory transplantation-related diseases or disorders include graft rejection, chronic graft rejection, subacute graft rejection, acute graft rejection hyperacute graft rejection, and graft versus host disease or disorder. Exemplary implants include a prosthetic implant, a breast implant, a silicone implant, a dental implant, a penile implant, a cardiac implant, an artificial joint, a bone fracture repair device, a bone replacement implant, a drug delivery implant, a catheter, a pacemaker, an artificial heart, an artificial heart valve, a drug release implant, an electrode, and a respirator tube.

Non-limiting examples of inflammatory tumors include a malignant tumor, a benign tumor, a solid tumor, a metastatic tumor and a non-solid tumor.

Non-limiting examples of inflammatory pulmonary diseases or disorders include asthma, allergic asthma, emphysema, chronic obstructive pulmonary disease or disorder, sarcoidosis and bronchitis.

An example of a proliferative disease or disorder is cancer.

In some examples according to any of the above embodiments, the pharmaceutical compositions of the present disclosure or the capsules of the present disclosure are administered to the subject concomitantly with another active pharmaceutical agent that is other than an oxidized phospholipid as described herein (co-therapy). For example, the pharmaceutical composition or the capsule of the current disclosure is administered to the subject concomitantly with a statin (i.e., the subject undergoes statin therapy at the time the oxidized phospholipid is administered to the subject). In one embodiment, the statin is administered in a separate dosage form. The oxidized phospholipid can be administered at the same time of the day as the statin or at a different time of the day.

Other Definitions

As used herein the term "about" refers to ±10%.

The terms "comprises", "comprising", "includes", "including", "having" and their conjugates mean "including but not limited to".

The term "consisting of" means "including and limited to".

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition, or substantially preventing the appearance of clinical or aesthetical symptoms of a condition.

As used herein the term "alkyl" means, unless otherwise stated, a straight or branched chain hydrocarbon radical having the number of carbon atoms designated (e.g., $C_1$-$C_{10}$ means one to ten carbon atoms). In the context of this application, e.g., with respect to the variable $R^1$ in Formulae (I), (II), and (III), an alkyl group will typically have from 1 to 30 carbon atoms, for example having from 10 to 30 carbon atoms, from 12 to 30 carbon atoms or from 14 to 30 carbon atoms. Other exemplary alkyl groups have from 14 to 20 carbon atoms. Exemplary alkyl groups include tetradecyl, pentadecyl, hexadecyl, heptadecyl, octadecyl, nonadecyl, eicosanyl, cis-9-hexadecenyl, and (2-octyl)dodecyl. In other examples, e.g., with respect to the variable $R^5$ in Formulae (I), (II), and (III), the alkyl group is a "lower alkyl" group having from 1 to 10 carbon atoms, from 1 to 8 carbon atoms, from 1 to 6 carbon atoms, or from 1 to 4 carbon atoms. Examples of "lower alkyl" radicals include, but are not limited to, methyl, ethyl, n-propyl, iso-propyl, n-butyl, tert-butyl, iso-butyl, sec-butyl, as well as homologs and isomers of, for example, n-pentyl, n-hexyl, n-heptyl and n-octyl. The term "alkyl" includes di- and multivalent radicals. For example, the term "alkyl" includes "alkylene" wherever appropriate, e.g., when the formula indicates that the alkyl group is divalent. The term "alkyl" includes "alkenyl" and "alkynyl" as defined herein.

The term "alkylene" means a divalent (diradical) alkyl group, wherein alkyl is defined herein. Typically, an "alkylene" group will have from 1 to 30 carbon atoms. Other exemplary ranges for the number of carbon atoms are those described for "alkyl". "Alkylene" is exemplified, but not limited, by butylene (—$CH_2CH_2CH_2CH_2$—).

The term "alkenyl" refers to a straight or branched chain hydrocarbon radical having from 2 to 30 carbon atoms and at least one double bond. Other exemplary ranges for the number of carbon atoms are those described for "alkyl". A typical "alkenyl" group has from 12 to 30 carbon atoms and at least one double bond. In one embodiment, "alkenyl" groups have from 14 to 30 carbon atoms or from 14 to 20 carbon atoms and at least one double bond. An exemplary "alkenyl" group is cis-9-hexadecenyl. Exemplary "lower alkenyl" groups having from 2 to 10, from 2 to 8, from 2 to 6, or from 2 to 4 carbon atoms include vinyl, 2-propenyl, 1-but-3-enyl, crotyl, 2-(butadienyl), 2,4-pentadienyl, 3-(1,4-pentadienyl), 2-isopentenyl, 1-pent-3-enyl, 1-hex-5-enyl and the like.

The term "alkynyl" refers to a straight or branched chain, unsaturated or polyunsaturated hydrocarbon radical having from 2 to 30 carbon atoms and at least one triple bond. Other exemplary ranges for the number of carbon atoms are those described for "alkyl". In the context of this application, an "alkynyl" group typically has from 12 to carbon atoms and at least one triple bond. In some examples of the present disclosure, "alkynyl" groups have from 12 to 20 carbon atoms and at least one triple bond. An "alkynyl" group may additionally include one or more double bonds. Other "alkynyl" groups are "lower alkynyl" groups having from 2 to 10 carbon atoms (e.g., 2 to 6 carbon atoms), which include prop-1-ynyl, prop-2-ynyl (i.e., propargyl), ethynyl and 3-butynyl.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Materials and Methods

Materials:
Acryl-EZE® was obtained from Colorcon;
Gelatin was obtained from DG Stoess;
Lauroglycol FCC was obtained from Gattefosse;
Magnesium stearate was obtained from Procter & Gamble;
Opadry® AMB was obtained from Colorcon;
PEG6000 was obtained from BASF;
Poloxamer 188 (Lutrol® F 68) was obtained from BASF;
Size 0 gelatin capsules were obtained from Qualicaps and from Capsugel;
Talc (Ph Eur) was obtained from Fluka;
Tocopherol polyethyleneglycol succinate (TPGS) was obtained from Eastman Chemical Co.;
TWEEN 80 was obtained from Riedel-de-Haën; and
VB-201 was obtained from Cordenpharma (previously Genzyme).

Gravimetric Vapor Sorption:
Sorption was analyzed using an IGAsorp Moisture Sorption Analyser (Hiden Analytical). A sample of VB-201 was carefully placed on the ultra-microbalance of the instrument and dried in a stream (250 standard cubic centimeters per minute) of dry nitrogen (<0.1% relative humidity) until equilibration had been attained. The sample was then exposed to the following water relative humidity profile: 10, 20, 30, 40, 50, 60, 70, 80 and 90% relative humidity, allowing equilibration to be attained at each step (99.5% step completion). The study was continued for a period of 3 days. The sorption isotherm was calculated from the equilibrium mass values at each step.

Isothermal Calorimetry:
Samples of 88 mg VB-201, 262 mg Lauroglycol FCC, and 88 mg VB-201 combined with 262 mg Lauroglycol FCC were freshly prepared and loaded immediately into a calorimeter (TAM, Thermometric AB, Sweden), and the unit was then allowed to equilibrate at 25° C. for a period of 30 minutes. Data were collected every 15 seconds for a period of 24 hours using the dedicated software package Digitam 4.1. Samples containing 350 mg water were used as the reference. Data analysis was performed using the graphical software package Origin (Microcal Software Inc., USA). The calorimeter was calibrated using the electrical substitution method and was run with an amplifier range of 300 μW.

Differential Scanning Calorimetry (DSC):
Approximately 5 mg of sample was placed in an aluminum DSC pan and sealed with a pin-hole lid. The sample was loaded into a Pyris 1 differential scanning calorimeter (Perkin Elmer) held at 10° C., and then cooled to −20° C. After equilibration, the sample was heated from −20° C. to 100° C. at a rate of 10° C. per minute, held at 100° C. for 1 minute, and cooled from 100° C. to −20° C. at a rate of 20° C. per minute.

During the temperature cycles, the sample was purged with nitrogen at a flow rate of 20 ml per minute to prevent oxidation.

Prior to analysis, the calorimeter was temperature-calibrated and heat flow-calibrated using an indium reference standard.

Thermogravimetric Analysis (TGA):

Approximately 5-10 mg of sample was laced in a platinum pan and loaded into a TGA 1 Thermogravimetric analyzer held at ambient temperature. The sample was then heated from 5° C. to 300° C. at rate of 10° C. per minute while monitoring the weight of the sample. Nitrogen was used to purge the sample at a flow rate of 20 ml/minute to prevent oxidation upon heating.

Prior to analysis, the instrument was temperature calibrated using an alumel reference standard, and weight calibrated using a 100 mg calibration weight.

Powder-Pocket Dynamic Mechanical Analysis:

Dynamic mechanical analysis (DMA) measures the mechanical properties of a sample as a function of temperature. The solid sample is subjected to an oscillating stress which results in oscillating strain within the sample. The applied force and the amplitude and phase of the resultant displacement are measured.

Most materials behave viscoelastically, such that the oscillating strain lags behind the applied oscillating stress by a phase difference $\delta$. The modulus (the ratio of the force or stress to the deformation or strain) thus has an in-phase component, which corresponds to an elastic response and is defined as the storage modulus, as well as an out-of-phase viscous component, defined as the loss modulus. The ratio of loss modulus to storage modulus equals the damping parameter tan $\delta$, which is proportional to the ratio of dissipated mechanical energy (primarily as heat) to stored mechanical energy for each cycle.

Powder-pocket DMA allows analysis of powder by holding the powder between to thin plates of steel. Experiments were performed using a Perkin Elmer DMA 8000 apparatus. Approximately 50 mg of sample powder was loaded into metal pockets, which were closed to form a thin sandwich of approximately 0.4 mm of powder encased in the pocket. The pocket was then clamped directly into the instrument, one end on end into a rigid frame and the other end attached to a moving driveshaft. The experimental geometry used to determine the force data in the software was a rectangular cross-section in a single cantilever bending using a single frequency deformation mode. The pocket was subjected to a bending oscillatory motion in and out of the plane, forcing horizontal shearing of the powder between the two plates of the pocket.

The samples were heated from −20° C. to 50° C. at a rate of 2° C. per minute. Optimized experimental conditions were used, namely, a dynamic displacement of 0.05 mm under frequencies of 1 Hz, 10 Hz and 30 Hz. The modulus was then calculated from the measured dynamic displacement amplitude.

The instrument was calibrated for temperature using the melting point of indium (156.6° C.), and for force by placing a known weight of approximately 100 grams on the driveshaft according to the manufacturer's instructions.

Overview:

VB-201 is synthetically prepared via published procedures (see, e.g., U.S. patent application Ser. No. 11/650,973), dried from solvents by evaporation under reduced pressure and oven dried. It is obtained as a waxy solid material which shatters and powders easily at room temperature, 18-22° C. VB-201 was further characterized as highly hygroscopic. These physicochemical properties of the API (active pharmaceutical ingredient) suggest that conventional oral solid dosage form (e.g. tablet or powder blend capsule) could not be developed. Accordingly, studies were made for developing either liquid fill capsules of solubilized drug (which stay as liquid) or liquid fill capsules of molten carrier which become solid on cooling.

The following examples describe the route for developing suitable oral dosage forms of VB-201.

Example 1

Encapsulation of VB-201 in Gelatin Capsules Using a Lauroglycol FCC Carrier

The solubility of VB-201 in Lauroglycol FCC (propylene glycol laurate) was tested, and was found to be at least 255 mg per gram. VB-201 was also found to be stable in Lauroglycol FCC over the course of 66 days (data not shown). Based on these results, Lauroglycol FCC was considered to be a suitable liquid carrier for VB-201.

In order to test the stability of VB-201 in gelatin capsules, size 0 capsules were filled with 255 mg/gram VB-201 in Lauroglycol FCC and then sealed. Capsules were stored under the following storage conditions; a) ambient relative humidity at 4° C.; b) 65% relative humidity at room temperature; and c) 75% relative humidity at 40° C.

As shown in Table 1, VB-201 content in the capsules was reduced, in contrast to the results obtained for VB-201 in Lauroglycol FCC in the absence of capsules.

In order to determine whether the VB-201 interacted with the gelatin in a way which caused the VB-201 to be refractory to the analysis, VB-201 was extracted from gelatin capsules in order to recover any VB-201 which interacted with the gelatin. Capsules were removed from storage after 24 days or 59 days.

As shown in Table 1 below, when VB-201 was assayed by extraction of the capsules, no significant loss of VB-201 were observed even after 59 days of storage at 4° C. with ambient relative humidity or at room temperature with 65% relative humidity. The VB-201 content of capsules stored at 40° C. with 75% relative humidity decreased by approximately 20%.

TABLE 1

Stability of VB-201 in gelatin capsules, as determined by sampling unsealed capsules and by extraction of VB-201 from capsules

| Initial recovery (no storage) | Storage condition | Recovery of VB-201 after different storage times (%) | | | |
|---|---|---|---|---|---|
| | | Sampling unsealed capsules | | Extraction of capsules | |
| | | 10 days | 16 days | 24 days | 59 days |
| 96.74% | 4° C., ambient relative humidity | 87.7 | 84.7 | 96.7 | 96.8 |
| | Room temperature, 65% relative humidity | 87.0 | 91.8 | 90.9 | 99.1 |
| | 40° C., 75% relative humidity | 56.3 | 62.6 | 92.1 | 79.6 |

The above results suggest that VB-201 interacts with the gelatin capsule during storage, but that the VB-201 is recovered when the capsule breaks down. Hence, the VB-201 would be available for absorption when a capsule breaks down in the gut.

VB-201 was then encapsulated on a larger scale. VB-201 was dissolved in Lauroglycol FCC at a temperature of approximately 40° C. The solution was then encapsulated in gelatin capsules at a similarly slightly elevated temperature, using a Bosch 1500 L filling machine. The capsules were then banded with gelatin on a Qualiseal S100 banding machine. Capsules with 5, 20, 25 and 100 mg VB-201 were prepared. Placebo capsules containing Lauroglycol FCC without VB-201 were also prepared.

The capsules were then leak tested under reduced pressure and, where appropriate, transferred for coating with Acryl-EZE®, a pharmaceutical enteric coat formulation, in a Manesty Accelacota coating machine. An undercoat of Opadry4 AMB, a moisture barrier sub-coat, was applied to prevent moisture migration through the Acryl-EZE® coat, which softens and distorts capsules during dissolution testing.

It was noticed that leaks developed in capsules prior to coating with an enteric coat. The source of the leaks was identified as progressive cracking of the capsules, which was capable of leading to loss of all the VB-201 in the capsule. Cracking was not observed in coated capsules or in uncoated placebo capsules (i.e., without VB-201).

The above results indicate that VB-201 may be encapsulated in liquid-fill gelatin capsules, but that VB-201 causes cracking of uncoated gelatin capsules.

Example 2

Hygroscopicity of VB-201

The physical properties of VB-201 were examined in order to understand the mechanism whereby VB-201 causes cracking of gelatin capsules, as described in Example 1.

The aqueous solubility of VB-201 was determined by suspending VB-201 in aqueous solutions of 0.1 M HCl (pH 1) or in 50 mM phosphate buffers (pH 5 and 7). After initial hand mixing, the preparations were further mixed by vortexing and bath sonication to try to bring about dissolution of the drug. Optical microscopy was used to examine for the presence of undissolved material. Using this method, it was determined that the solubility of VB-201 at each of the tested pH values is in excess of 225 mg/gram. Thus, VB-201 is relatively water-soluble.

Absorption of humidity by VB-201 was determined by gravimetric vapor sorption analysis, as described in the Materials and Methods section.

As shown in FIGS. 1A and 1B, a slight weight loss was observed when VB-201 was exposed to 0% relative humidity.

This result indicates that the VB-201 contained some absorbed water.

As further shown in FIGS. 1A and 1B, the VB-201 increased slightly (by approximately 3.5%) in weight as the relative humidity was increased gradually to 40%, followed by a large increase (>30%) in weight as the relative humidity was increased beyond 40%, particularly in the range of 40% to 60% relative humidity.

These results suggest that a phase transition occurred in the VB-201 at relative humidities of 40% to 60%, with the formation of a hydrated state, or formation of a supersaturated solution.

As further shown in FIG. 1B, the sorption and desorption profiles were similar in the range of 60% to 90% relative humidity, whereas there was a considerable difference between the profiles (hysteresis) in the range of 0% to 60% relative humidity.

These results suggest that between 60% and 90% relative humidity, the water is simply absorbed into the bulk of the structure without chemically interacting with the sample (physisorption), whereas between 0% and 60% relative humidity, there was sorption and desorption of a more strongly bound water species from the sample.

The above results further indicate that VB-201 is highly hygroscopic. The VB-201 is physically stable with regards to hygroscopicity as long as the relative humidity is maintained below 40%. Relative humidities greater than 40% result in the formation of a supersaturated solution, with possible deliquescence of the VB-201.

As highly hygroscopic substances can potentially absorb water from an outside environment even when dissolved in a hydrophobic oil phase (e.g., Lauroglycol FCC), the hygroscopicity can affect the stability of a formulation and/or capsule, especially if soft gelatin capsules are used. The relative humidity range at which gelatin capsules are stable lies between 35% and 65%, and VB-201 is highly hygroscopic in this range.

As nearly all chemical or physical processes are accompanied by a change in heat, VB-201 and Lauroglycol FCC (alone and in combination) were also examined using isothermal calorimetry, as described in the Materials and Methods section. Preliminary results are shown in FIGS. 2, 3 and 4.

As shown in FIG. 2, VB-201 exhibited an endothermic signal of approximately −6 μW over the first 11 hours. This result indicates instability of VB-201.

As shown in FIGS. 3 and 4, no significant signal was observed for either Lauroglycol FCC (FIG. 3) or for Lauroglycol FCC with VB-201 (FIG. 4).

These results indicate that VB-201 undergoes a change, but that Lauroglycol FCC prevents this change. The results are consistent with a mechanism wherein VB-201 absorbs moisture and Lauroglycol FCC excludes moisture, thereby limiting absorption by VB-201.

The above results, along with the interaction between VB-201 and gelatin described in Example 1, suggest that the VB-201-associated cracking of gelatin capsules and subsequent leakage, as described in Example 1, is due to the hygroscopic properties of VB-201.

Example 3

Encapsulation of VB-201 in Gelatin Capsules Using a Solid Carrier

In order to provide a more stable gelatin capsule containing VB-201, VB-201 was incorporated into a solid excipient having a low melting point, by adding VB-201 to the molten excipient.

The solid formulation was expected to be advantageous because no leakage is possible, the VB-201 is immobilized and therefore prevented from interacting with the gelatin shell wall, and absorption of water by VB-201 would be limited.

In order to facilitate HPLC analysis, the excipient was selected to have little UV absorption and to be water-soluble. The excipient was further selected so as to be FDA-approved. Based on the aforementioned criteria, PEG6000 (polyethylene glycol with a molecular weight of 6000 daltons) and TPGS (tocopherol polyethylene glycol succinate) were selected as suitable excipients, and tested in order to determine which excipient provides the best stability. The melting point of TPGS is about 40° C., and the melting point of PEG6000 is about 60° C.

Binary mixes were prepared at 20% (w/w) VB-201 in TPGS and PEG6000, matching the VB-201 concentration in a 100 mg dosage unit. The excipient was melted in an oil bath and ground VB-201 was incorporated into the mix with high shear mixing. Both blends appeared by visual examination to form a uniform mix. Samples of both excipients (without VB-201) and binary mixes were stored in sealed amber glass bottles at 40° C. with 75% relative humidity or at 5° C. for four weeks. Approximately 500 mg of the mix was also used to fill size 0 gelatin capsules obtained from either of two manufacturers (Shionogi and Capsugel), and the capsules were banded and then stored under the abovementioned conditions.

After one week, capsules filled with the TPGS-based formulation exhibited no cracking or deformation, although leakage was observed and almost all of the capsules were brittle.

However, capsules filled with the PEG6000-based formulation exhibited no leakage or embrittlement, even after 4 weeks, in addition to exhibiting no cracking or deformation. Based on this result, PEG6000 was selected as the excipient for subsequent tests.

Example 4

Machine Encapsulation of VB-201 with a PEG6000 Carrier

VB-201 gelatin capsules containing 25 mg or 100 mg VB-201 were prepared on a large scale (12,000-24,000) by machine encapsulation. PEG6000 was melted at 65° C. in a Schweizer mixer, and VB-201 was then incorporated as a powder that had been produced in a small scale bladed blender under nitrogen. The mix was mixed using paddle stirring and full speed high shear mixing.

The mix was degassed and transferred to the heated hopper of a Bosch full scale filling machine where the formulation was encapsulated at a target temperature of 65° C. The capsules were then banded and coated with an Acryl-EZE® enteric coating, as described in Example 1.

Additional batches of capsules with 5, 10 or 25 mg VB-201 were prepared on a smaller scale (3,400), using procedures similar to those described above. The VB-201 was incorporated into molten PEG6000 in a stainless vessel, mixed by a spatula, and then distributed using a bench scale high shear mixer. The mix was then degassed and encapsulated as described above, but capsules were not banded or coated.

After high shear mixing, the mixes did not appear by visual examination to have any inhomogeneity, although it was noticed that they had a "wallpaper paste" consistency. In addition, VB-201 became sticky on incorporation, and some lumps needed to be dispersed with a spatula before they would pass through the high shear head.

The VB-201 content was assayed in order to test the accuracy and uniformity of the VB-201 content, and the results are summarized in Table 2 below.

TABLE 2

VB-201 content and uniformity of capsules with PEG6000 carrier

| Batch No. | Scale of production | Target VB-201 content | VB-201 content (% of target) | Uniformity of VB-201 content (RSD = relative standard deviation) |
|---|---|---|---|---|
| 103/029/2 | 24,000 | 25 mg | 106.2 | 9/10 capsules within ±15% of mean 1 capsule 117.5% of mean |
| 103/029/3 | 12,000 | 100 mg | 105.3 | 10/10 capsules within ±15% of mean |
| 103/032/2 | 24,000 | 25 mg | 101.7 | 9/10 capsules within ±15% of mean 10/10 within ±25% of mean |
| 103/032/3 | 13,000 | 100 mg | 104.6 | 8/10 capsules within ±15% of mean 1/10 capsules outside ±25% of mean |
| VC2434 | 3,400 | 5 mg | 103.47 | Range: 80.33%-119.79% of target RSD = 11.08% Batch L1 value = 29.48 |
| VC2436 | 3,400 | 10 mg | 102.7 | Range: 92.70%-108.79% of target RSD = 4.80% Batch L1 value = 13.04 |
| VC2438 | 3,400 | 25 mg | 106.67 | Range: 99.00%-146.91% of target RSD = 13.41% Batch L1 value = 39.52 |

As shown in Table 2, the average VB-201 content in all of the batches was close to 100% of the target. However, the uniformity of content in some of the batches was relatively low. As the capsules had uniform weights, the relatively low uniformity indicated that inhomogeneities were present in the mixes.

It was hypothesized that inhomogeneities were present in the mixes due to the viscous lumps which were formed when VB-201 was added to molten PEG6000. Bench scale trials were therefore performed in which VB-201 was ground with PEG6000 before being added to PEG6000, in order to ease incorporation of the VB-201 into the PEG6000.

1 part ground VB-201 was combined with 1, 2 or 3 parts ground PEG6000 at room temperature to form a free flowing powder blend. These blends greatly increased the ease of incorporation of VB-201 into molten PEG6000 and a ratio of 2:1 PEG6000:VB-201 was selected as the best compromise for further trials.

Batches of capsules (3,400 capsules) were then prepared by incorporating the VB-201/PEG6000 blend into molten PEG6000 in a stainless vessel, mixed by a spatula, and then distributed using a bench scale high shear mixer. The mix was then degassed and encapsulated as described above. Capsules were not coated with an enteric coating.

Incorporation of VB-201 was considerably improved, with no viscous lumps being formed upon incorporation. No inhomogeneities were visible after mixing, and the mix was used to fill capsules at 65° C. without any difficulty.

The VB-201 content was assayed in order to test the accuracy and uniformity of the VB-201 content, and the results are summarized in Table 3 below.

TABLE 3

VB-201 content and uniformity of capsules prepared from VB-201 ground with PEG6000

| Batch No. | Target VB-201 content | VB-201 content (% of target) | Uniformity of VB-201 content (RSD = relative standard deviation) |
|---|---|---|---|
| VE2480 | 10 mg | 93.75 | Range: 57.49%-102.31% of target RSD = 15.06% Batch L1 value = 38.63 |
| VE2482 | 20 mg | 97.93 | Range: 72.55%-112.38% of target RSD = 8.95% Batch L1 value = 18.11 |

As shown in Table 3, the average VB-201 content in all of the batches was close to 100% of the target, but the content uniformity was poor.

Example 5

Hand Encapsulation of VB-201 with a PEG6000 Carrier

In order to improve homogeneity, capsules containing 10 mg VB-201 were prepared without the use of machine filling, in which material may separate, adhere and/or be filtered out of a mix.

A mix was prepared from a blend containing 1 part VB-201 and 2 parts PEG6000, using the procedures described in Example 4. Capsules were then hand-filled at a temperature of 65° C. using plastic disposable syringes with material taken from the outlet of the high shear head. All capsules were individually filled to the target weight, with the target VB-201 content being 10 mg. The VB-201 content was assayed in order to test the accuracy and uniformity of the VB-201 content. The average VB-201 content was 89.41% of the target content (10 mg), and the range of the VB-201 content was from 56.21% to 102.23% of the target content. Thus, the average VB-201 content was considerably below target and the results indicate that poor homogeneity is not due to machine filling per se.

Example 6

Effect of Temperature on Solubility of VB-201 in PEG6000

In order to further enhance the uniformity of VB-201 capsules, the effect of temperature on VB-201 solubility in PEG6000 was studied, so as to determine whether dissolution/precipitation contribute to poor homogeneity.

Nine pieces of caked, non-ground VB-201 were submerged in molten PEG6000 at 65° C. and stirred slowly using a paddle mixer. The mix was held for approximately two hours at this temperature, examined visually for the dissolution state of the VB-201, and three samples of the liquid PEG6000 were then taken for analysis. The temperature was then raised by 10° C. and the process was repeated. The process was repeated in 10° C. steps until the mix reached a final temperature of 105° C. The entire process lasted 30 hours.

After 30 hours and at a temperature of 105° C., the PEG6000 had slowly turned lightly yellow (normal for prolonged heating of PEG6000 in air), yet there was no significant visible dissolution of VB-201 or reduction in size of the VB-201 pieces. After taking the final analytical samples the VB-201 pieces were removed from the melt, dried from PEG6000, and weighed. The weight recorded (32 grams) indicated that there was no significant change from the initial weight (25 grams), when taking into consideration adherence of some PEG6000 to the solid VB-201.

After removing the solid VB-201, the PEG6000 was allowed to cool from 105° C. to 65° C. There was no precipitation of material from the mix.

Chemical analysis of the PEG6000 samples showed there was no detectable VB-201, indicating that the VB-201 concentration was less than approximately 0.5 mg/gram.

The above results indicate that VB-201 has negligible or no solubility in molten PEG6000, and that a dissolution/precipitation mechanism is not a cause of the variable homogeneity which was observed.

It was then observed that at a temperature of 28-30° C., the solid VB-201, before use or removal from containment bags, transformed from a brittle solid into a rubbery, stretchy, cohesive material.

It was further observed by careful examination after encapsulation and removal of remaining mix, that the walls of the filling machine hopper and the Schweizer mixer showed dimpling on the surface. The appearance of the walls suggested that particles were left on the wall, although no discrete particles were visible. Although the mix looks almost transparent, it is possible that the refractive index of PEG6000 and VB-201 are sufficiently similar such that particles are not visible.

In addition, the high shear head was observed to have rims of material left round its exit slots, a phenomenon which does not usually occur.

The above observations indicate that VB-201 became soft and sticky when added to molten PEG6000 due to the elevated temperature (at least 65° C.) of the molten PEG6000 required, and that the VB-201 was sufficiently soft so as to be extruded from the high shear head, rather than being dispersed. The mix then behaved in a manner similar to two immiscible liquids. Poor homogeneity of the mixes could have been caused by agglomeration, adhesion and/or separation of the VB-201 in the molten PEG6000.

The observation that VB-201 transforms from a brittle solid such as a free flowing powder into a rubbery, stretchy, cohesive material at a temperature of about 28-30° C. was confirmed by results obtained from differential scanning calorimetry and dynamic mechanical analysis.

Slow scan differential scanning calorimetry was performed for solid VB-201 as described in the Materials and Methods section.

As shown in FIG. 5, an endothermic transition occurred when the VB-201 was heated to about 25° C. As further shown therein, a corresponding transition occurred during cooling at a moderately lower temperature. The lower transition temperature during cooling suggests supercooling of the VB-201.

In order to determine whether the observed transition is due to removal of a volatile compound, thermogravimetric analysis was performed as described in the Materials and Methods section.

As shown in FIG. 6, no significant weight loss is observed when VB-201 was heated to about 25° C.

These results indicate that a phase transition of VB-201 occurs when heating to about 25° C., and that the observed transition is not due to removal of a volatile compound.

Powder-pocket dynamic mechanical analysis (DMA) of solid VB-201 was performed as described in the Materials and Methods section.

As shown in FIG. 7, the storage modulus of VB-201 gradually decreases upon heating above 0° C. The decrease ends abruptly at about 30° C. These findings indicate that the VB-201 gradually softens upon heating above 0° C., as the VB-201 begins to undergo a phase transition, and that the phase transition is complete at about 30° C.

As shown in FIG. 8, the tan δ value of VB-201 gradually increases upon heating above 0° C., and then falls abruptly at temperatures above about 25° C. As further shown therein, the temperature at which tan δ is maximal increases as the oscillation frequency is increased.

The above results are consistent with a glass transition (Tg) of an amorphous material, which typically appears as a step-like lowering of the storage modulus when the sample is heated through Tg, and as a large peak in tan δ. The frequency-dependency of the temperature at which tan δ is maximal indicates that the phase transition is not a crystalline-to-liquid transition, as such transitions are thermodynamically driven and therefore not associated with frequency dependency. However, glass transitions are kinetic and therefore may be frequency-dependent.

The above differential scanning calorimetry and dynamic mechanical analysis results indicate that VB-201 undergoes a phase transition at about 25° C., confirming the visual observation that VB-201 is transformed into a rubbery, stretchy, cohesive material at temperatures above about 25° C.

Example 7

Mixing of VB-201 with Additives and a PEG6000 Carrier

In order to identify a material that would coat the VB-201 granules and prevent them from sticking together in a mix, ground VB-201 was combined at room temperature with various additives before being mixed with molten PEG6000.

The following combinations were tested:
1) 2.5 grams of ground VB-201 wetted with 1 gram of Lauroglycol FCC;
2) 2.5 grams of ground VB-201 wetted with 1 gram of TWEEN 80;
3) 2.5 grams of VB-201 ground together with 5 grams of PEG6000, then wetted with 1 gram of Lauroglycol FCC;
4) 2.5 grams of VB-201 ground together with 5 grams of PEG6000, then wetted with 1 gram of TWEEN 80;
5) 2.5 grams of VB-201 ground together with 0.3 gram of magnesium stearate;
6) 2.5 grams of VB-201 ground together with 0.3 gram of magnesium stearate and 5 grams of PEG6000;
7) 1 part VB-201 ground together with 3 parts talc and 2 parts PEG2000;
8) 1 part VB-201 ground together with 3 parts talc;
9) 1 part VB-201 ground together with 2 parts talc;
10) 1 part VB-201 ground together with 1 part talc;
11) 1 part VB-201 ground together with 0.5 part talc; and
12) 1 part VB-201 ground together with 0.25 part talc.

Addition of Lauroglycol FCC or TWEEN 80 (with or without PEG6000) resulted in a sticky material, whereas addition of magnesium stearate or talc (with or without PEG6000) resulted in a free-flowing powder.

The combined material was then placed in a sealed amber glass jar, and placed in a stability cabinet at 40° C. After 1 hour at 40° C., all combinations appeared sticky and/or fused, except for combinations including talc, which remained free-flowing even after being stored for several hours (typically overnight) at 40° C., although the 1 part VB-201/0.25 part talc mixture agglomerated following 24 hours at 40° C.

The mixtures containing Lauroglycol FCC, TWEEN 80 or magnesium stearate were added to 50 grams of molten PEG6000 at 65° C. and high shear mixed. The samples were kept at a temperature of 65° C. and degassed, and were then examined visually. In all of the samples, the VB-201 formed a mass at the surface, and lumps were present. The samples were not used further.

In a similar test, all of the talc-containing powders which were free-flowing at 40° C. were incorporated into molten PEG6000 (at 65° C.) using a spatula. High shear mixing was not used, as the powders were readily distributed in the PEG6000 and appeared to form a uniform mix. All mixes were prepared at a concentration that would incorporate 20 mg of VB-201 in a total mass of 420 mg.

On being held overnight at 65° C., the talc slowly settled into a thick layer on the bottom. The talc was readily redistributed by brief stirring.

There was no sign of VB-201 on the surface of the PEG6000 after standing, granules of VB-201 were not seen on the vessel walls, nor did the mix have a "wallpaper paste" appearance as was seen in previously prepared VB-201/PEG6000 mixes without talc.

The VB-201/talc combination appeared to slowly settle to the bottom of the PEG6000, although VB-201 without talc rises under identical conditions. This indicates that the talc adhering to the VB-201 increases the average density of the VB-201/talc combination to above the density of PEG6000.

The abovementioned mixes were used to fill capsules by hand. The content of capsules prepared using the powder with a 1:1 ratio of VB-201/talc was analyzed. The average content of VB-201 in these capsules was 100.39% of the target (range: 97.04-103.49%), with a relative standard deviation of 2.38%.

These results indicate that VB-201 powder mixed with talc, at a ratio of at least 0.5:1 talc to VB-201, facilitates the preparation of capsules with the desired quantity of VB-201 and with high uniformity between capsules.

Example 8

Uniformity Over Time of VB-201 Capsules Prepared with Talc and PEG 6000

Two 5 kg technical scale batches of VB-201 capsules were prepared using the incorporation of talc described in Example 7.

Talc was incorporated at a ratio of 1:0.5 VB-201 to talc by grinding VB-201 with talc. The ground mix was added to molten PEG6000 at 70° C. and mixed using low shear mixing followed by 10 minutes of high shear mixing at low speed (50 on mixer readout) in a temperature controlled 20l Schweizer mixer. The mix was degassed and encapsulated using a Bosch 1500 L filling machine with paddle mixing (moderate speed) in the hoppers.

In the first technical batch filling continued over 30 minutes with analytical capsule samples being taken at the beginning, middle and end of the run. The filling machine speed was 30,300 capsules per hour per hopper. For each sample, ten capsules were analyzed for VB-201 content and uniformity of fill. The results are shown in Table 4 below:

TABLE 4

VB-201 content and uniformity of capsules prepared using 1:0.5 ratio of VB-201 to talc in PEG6000 (first batch)

| Sample | VB-201 consent (% of target) | Relative standard deviation (%) | Range (% of target) |
| --- | --- | --- | --- |
| Beginning of run | 102.53 | 3.68 | 97.43-108.63 |
| Middle of run | 106.86 | 5.34 | 95.26-113.24 |
| End of run | 86.89 | 14.17 | 67.43-101.38 |

As shown in Table 4, the content and uniformity of the capsules in the batch were relatively good for capsules from the beginning and middle of the run, both uniformity and accuracy of VB-201 content had deteriorated significantly by the end of the run.

These results suggest that VB-201 separated and began to sink in the hopper, adding additional VB-201 to the middle section and depleting VB-201 from the upper layer in the hopper. The enriched mix in the middle section was used to fill the capsules from the middle of the run, which had a high VB-201 content, and the depleted mix in the upper layer was used to fill the capsules from the end of the run, which had a low VB-201 content.

In order to confirm these results, a second technical batch was prepared with sub-division of the capsules produced in the batch into two sets of three sub-lots, giving six sub-lots in total. In addition, additional stirring was provided to determine whether this eliminated or reduced the apparent separation of VB-201.

For each set of three sub-lots, the filling machine hopper was filled with half of the mix described hereinabove, and capsules were filled with one sub-lot containing capsules prepared at the beginning, one sub-lot containing capsules prepared at the middle, and one sub-lot containing capsules prepared at the end. The remaining mix was retained, while stirring, in the Schweizer mixer.

Once the first set of three sub-lots (numbered sub-lots 1-3) was prepared using almost all of the mix in the hopper, the remaining half of the mix was transferred from the mixer to the hopper, and used to prepare a second set of three sub-lots (numbered sub-lots 4-6), using the same process described herein for the first set of three sub-lots.

For both sets, vigorous paddle mixing (maximum practical speed) was applied to the machine hopper. The speed of mixing of the second set was reduced slightly, as the speed used for the first set appeared to be so vigorous as to slightly impede the flow of mix into the filling pump (weight had to be continually increased as the hopper emptied).

All of the capsules of the batch were filled after a 70 minute period. However, a significant portion of this time period was due to transfer of the second half of the mix into the hopper. The filling machine speed was then reduced slightly to 18,000 capsules per hour per hopper. The final dregs remaining after the second set of sub-lots was completed were collected and designated as sub-lot 7.

For each sub-lot, ten capsules were analyzed for VB-201 content and uniformity of fill. The results are shown in Table 5 below:

TABLE 5

VB-201 content and uniformity of capsules prepared using 1:0.5 ratio of VB-201 to talc in PEG6000 (second batch)

| Sample | VB-201 content (% of target) | Relative standard deviation (%) | Range (% of target) |
|---|---|---|---|
| Sub-lot 1 (beginning) | 101.22 | 3.36 | 96.62-105.46 |
| Sub-lot 2 (middle) | 105.62 | 3.60 | 101.38-109.32 |
| Sub-lot 3 (end) | 95.62 | 12.96 | 73.99-107.60 |
| Sub-lot 4 (beginning) | 109.25 | 9.85 | 102.12-137.49 |
| Sub-lot 5 (middle) | 104.12 | 1.43 | 102.69-107.93 |
| Sub-lot 6 (end) | 94.86 | 17.05 | 74.91-131.10 |
| Sub-lot 7 (dregs) | 125.89 | 5.72 | 114.18-132.97 |

As shown in Table 5, the second batch showed a similar trend to that of the first batch.

The first two sub-lots from the first set (sub-lots 1 and 2) exhibited a VB-201 content close to the target, with relatively good uniformity, whereas the last sub-lot (sub-lot 3) exhibited decreased VB-201 content with low uniformity of content.

Similarly, the second set of sub-lots had a high VB-201 content and moderate uniformity of content in the first sub-lot (sub lot 4), a middle sub-lot that exhibited a VB-201 content close to the target, with excellent uniformity, and a third sub lot with a decreased VB-201 content and low uniformity of content. However, the second set was inferior to the first set, as sub-lot 4 exhibited significantly poorer accuracy and uniformity of content than did the corresponding sub-lot 1, and the low content and uniformity of sub-lot 6 was lower than even that of the corresponding sub-lot 3.

As further shown in Table 5, the last dregs (sub-lot 7) exhibited a very high VB-201 content.

The above results indicate that the accuracy and uniformity of VB-201 content decreased as a function of time spent by the mix in the machine hopper (e.g., sub-lots 3 and 6 were inferior to sub-lots 1, 2, 4 and 5).

The above results further indicate that the accuracy and uniformity of VB-201 content decreased as a function of time spent by the mix in the mixer (e.g., sub-lot 7 was inferior to sub-lots 4-6, which were inferior as a whole to sub-lots 1-3).

Thus, the above results suggest that the accuracy and uniformity of VB-201 content decrease over time, regardless of how the mix is handled during that time.

Example 9

Uniform Large Scale Batches of VB-201 Capsules Prepared with Talc and PEG 6000

As the results presented in Example 8 indicate that the accuracy and uniformity of VB-201 content of capsules decrease over time during preparation of capsules, the following encapsulation process was devised in order to meet pharmacopoeial standards. Briefly, capsules were filled rapidly with the talc-containing mix described hereinabove, and each batch of capsules was initially separated into sub-lots which were analyzed. Only satisfactory sub-lots were retained, and were then combined to provide a batch for release. Using these procedures, capsules with 20 mg VB-201 and 40 mg VB-201 were prepared.

VB-201 was ground with an equal weight of talc using a bladed bench scale grinder. The ground mix was added to molten PEG6000 at 70° C. and mixed, degassed and encapsulated as described in Example 8.

A small quantity of mix (suitable for 20 mg or 40 mg dosage units) was used to set the fill weight, the filling machine was pumped to dryness, and then all of the mix was transferred and the machine run at full speed (30,600 per hour per pump) without stopping until all the material was encapsulated. The product was collected in ten sub-lots of approximately 1000 capsules each. Filling took 21 and 23 minutes respectively for the 20 mg and 40 mg dosage units.

Batch size for both 20 mg and 40 mg dosage units was targeted at 11,400 capsules, with a 5-5.5 kg nominal mix quantity.

Ten capsule samples from each sub-lot were taken and analyzed for VB-201 content and uniformity of fill.

The agreed testing criteria were that every second sub-lot would be analyzed until a sub-lot failed. The sub-lot immediately preceding the failed sub-lot was then tested. All acceptable sub-lots up to the first sub-lot found unacceptable were combined to produce the batch for further release testing. The results of the sub-lot testing are shown in Table 6 below. The batch L1 value was 5.3 for the 20 mg capsules, and 3.7 for the 40 mg capsules (acceptance value was L1≤15).

TABLE 6

VB-201 content and uniformity of capsules in batch sub-lots for target dosage units of 20 mg and 40 mg VB-201

| Dosage unit | Sub-lot | VB-201 content (% of target) | Relative standard deviation (%) | Range (% of target) | Accept or Reject |
|---|---|---|---|---|---|
| 20 mg | 1 | | | | Accept |
| | 2 | 100.32 | 2.4 | 95.97-104.26 | Accept |
| | 3 | | | | Accept |
| | 4 | 101.74 | 3.2 | 94.23-106.20 | Accept |
| | 5 | | | | Accept |
| | 6 | 100.64 | 2.3 | 96.6-103.7 | Accept |
| | 1 | | | | Accept |

TABLE 6-continued

VB-201 content and uniformity of capsules in batch sub-lots for target dosage units of 20 mg and 40 mg VB-201

| Dosage unit | Sub-lot | VB-201 content (% of target) | Relative standard deviation (%) | Range (% of target) | Accept or Reject |
|---|---|---|---|---|---|
| | 8 | 99.49 | 1.8 | 97.2-102.6 | Accept |
| | 9 | 92.81 | 7.3 | 81.1-101.3 | Reject |
| | 10 | 113.2 | 12.7 | 77.2-129.1 | Reject |
| | 1-8 combined | 100.72 | 2.18 | 97.2-105.1 | Accept |
| 40 mg | 1 | | | | Accept |
| | 2 | 98.41 | 1.6 | 95.59-100.23 | Accept |
| | | | | | Accept |
| | 4 | 99.43 | 1.0 | 98.12-101.05 | Accept |
| | 5 | | | | Accept |
| | 6 | 100.38 | 1.0 | 98.98-102.05 | Accept |
| | 7 | | | | Accept |
| | 8 | 99.30 | 1.4 | 96.6-101.8 | Accept |
| | 9 | 99.91 | 2.1 | 96.7-102.4 | Accept |
| | 10 | 104.74 | 10.2 | 76.5-111.2 | Reject |
| | 1-9 combined | 98.53 | 1.57 | 95.2-101.5 | Accept |

As shown in Table 6, the batches prepared as described above yielded a satisfactory product, and technical batches resulting in the availability of 7746 capsules with 20 mg VB-201 and 8732 capsules with 40 mg VB-201 were obtained after all rejects, waste and quality control sampling.

This process is repeated with similar yield using a two pump operation, to thereby obtain a batch size twice as large with similar product quality.

Example 10

Encapsulation of VB-201 with PEG 6000, Talc and a Thixotropic Agent

As described in Example 8, the quality of a VB-201/PEG6000 mix for encapsulation decreases over time, possibly due to separation of VB-201. A thixotropic agent was added to the mix in order to improve mix homogeneity by increasing viscosity and thereby slowing separation processes. Fumed silica was used as a thixotropic agent.

Capsules containing 20 mg, 40 mg or 80 mg VB-201 were prepared from a mix containing equal amounts of VB-201 and talc in a mixture of molten PEG6000 with 2.5% Aerosil® 200 fumed silica ("Aerosil 200").

PEG6000 was heated in a Schweizer mixer at 70±2° C. The fumed silica was added to the molten PEG6000 and incorporated by high shear mixing. The mixture was then degassed. VB-201 and talc were ground at a 1:1 ratio (by weight) until a uniform powder mixture was obtained. The powder mixture was rapidly transferred into the mixer and stirred thoroughly with a spatula to wet and disperse the powder. The mix was then stirred using a paddle mixer, until all the material appeared uniformly distributed, and then with a high shear mixer, until the mix appeared homogeneous. The mix was then degassed.

The mix was then transferred to a hopper of a Bosch 1500 L filling machine for encapsulation. During encapsulation, the mix was kept at a constant temperature of 70±2° C. Capsugel size 0 capsules were filled with the mix. Each capsule contained 10 mg fumed silica, 390 mg PEG6000, the indicated amount of VB-201 (20, 40 or 80 mg) and an equal amount of talc. The following compositions containing the indicated ingredients were thus prepared:

Formulation 1: 20 mg VB-201; 20 mg talc; 10 mg Aerosil 200; 390 mg PEG6000.
Formulation 2: 40 mg VB-201; 40 mg talc; 10 mg Aerosil 200; 390 mg PEG6000.
Formulation 3: 80 mg VB-201; 80 mg talc; 10 mg Aerosil 200; 390 mg PEG6000.

One of every two sub-lots was analyzed. For each tested sub-lot, 6 capsules were taken for analysis.

The results of the analysis of 40 mg VB-201 capsules are shown in Table 7 below. Encapsulation lasted approximately 6 hours.

TABLE 7

VB-201 content (% of target) and relative standard deviation (RSD) in capsules prepared with talc and a thixotropic agent

| Section | 1 | 3 | 5 | 7 | 9 | 11 | 13 |
|---|---|---|---|---|---|---|---|
| 1 | 98.59 | 99.66 | 98.49 | 102.69 | 96.03 | 103.93 | 102.39 |
| 2 | 103.61 | 101.03 | 103.03 | 97.56 | 97.30 | 104.34 | 100.21 |
| 3 | 101.14 | 99.03 | 97.24 | 98.65 | 95.10 | 101.56 | 102.71 |
| 4 | 95.16 | 98.14 | 98.98 | 103.14 | 100.10 | 98.65 | 100.28 |
| 5 | 98.61 | 100.93 | 98.56 | 98.19 | 99.05 | 101.21 | 105.99 |
| 6 | 99.31 | 99.09 | 99.40 | 96.19 | 100.16 | 98.86 | 99.13 |
| Average VB-201 content | 99.40 | 99.65 | 99.28 | 99.40 | 97.96 | 101.43 | 101.79 |
| RSD | 2.8% | 1.1% | 2.0% | 2.9% | 2.2% | 2.4% | 2.4% |

Overall average VB-201 content = 99.84
Overall RSD = 2.5%

As shown in Table 7, the average VB-201 content was extremely close to the target amount (99.84% of the target), with high uniformity (RSD=2.5%). As further shown therein, there was little change in uniformity over the course of the 6 hours of the manufacturing process.

These results indicate that the thixotropic agent was effective for stabilizing the mix for the duration of the encapsulation and for increasing uniformity of the obtained capsules.

Example 11

Encapsulation of VB-201 with Poloxamer 188, Talc and a Thixotropic Agent

Peroxide impurities in PEG may potentially cause gelatin crosslinking, which may lead to deterioration of the dissolution performance of the finished product. The use of poloxamers as alternative carriers to PEG was therefore investigated.

VB-201 was encapsulated using a thermosoftening carrier, talc as an anti-adherent agent, and Aerosil® fumed silica as a thixotropic agent, as described in Example 10, except that poloxamer 188 (Lutrol® F 68) was used instead of PEG6000 as the thermosoftening carrier.

Capsules containing 20 mg, 40 mg or 80 mg VB-201 were prepared from a mix containing equal amounts of VB-201 and talc in a mixture of molten poloxamer 188 with 3% Aerosil® 200 fumed silica.

The fumed silica was mixed with molten poloxamer 188. VB-201 and talc were ground at a 1:1 ratio (by weight) until a uniform powder mixture was obtained. The mix was then encapsulated such that each capsule contained 12 mg fumed silica, 388 mg poloxamer 188, the indicated amount of VB-201 and an equal amount of talc.

An exemplary flow diagram for the VB-201 drug product manufacturing process is shown below:

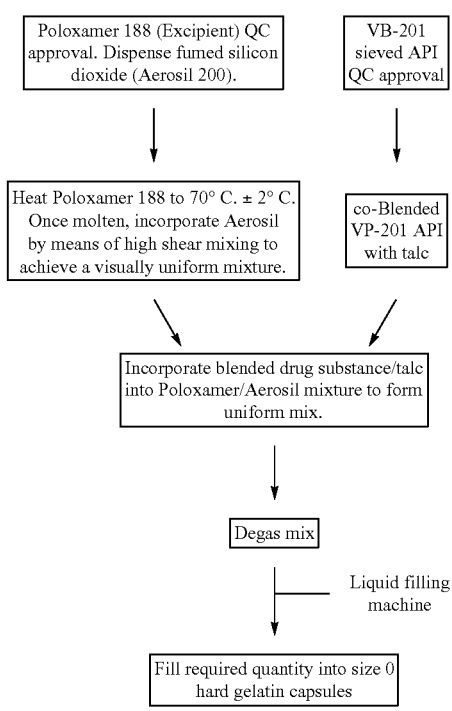

The following formulations were thus prepared:

Formulation 7: 40 mg VB-201 with 10 mg talc, 4 mg Aerosil 200 and 396 mg Poloxamer 188.

Formulation 8: 60 mg VB-201 with 15 mg talc, 4 mg Aerosil 200 and 396 mg Poloxamer 188.

Formulation 9: 80 mg VB-201 with 20 mg talc, 4 mg Aerosil 200 and 396 mg Poloxamer 188.

Each of the above compositions were added to a size 0, white gelatin capsule.

Example 13

Encapsulation of VB-201 with PEG 6000 and Talc (Without a Thixotropic Agent)

As described in Example 10, VB-201 was formulated with PEG6000 as the thermosoftening carrier with the difference that a thixotropic agent was not added. The following formulation containing 40 mg VB-201 was prepared from a mix containing equal amounts of VB-201 and talc in a mixture of molten PEG6000:

Formulation 10: 40 mg VB-201; 40 mg talc; 400 mg PEG6000.

The above composition was added to a size 0, white gelatin capsule.

In a similar fashion the following formulations can be prepared:

Formulation 11: 20 mg VB-201; 20 mg talc; 400 mg PEG6000.

Formulation 12: 60 mg VB-201; 60 mg talc; 400 mg PEG6000.

Formulation 13: 80 mg VB-201; 80 mg talc; 400 mg PEG6000.

The above compositions can be added to a size 0, white gelatin capsule.

The following formulations were thus prepared:

Formulation 4: 40 mg VB-201 with 40 mg talc, 12 mg Aerosil 200 and 388 mg Poloxamer 188.

Formulation 5: 20 mg VB-201 with 20 mg talc, 12 mg Aerosil 200 and 388 mg Poloxamer 188.

Formulation 6: 80 mg VB-201 with 80 mg talc, 12 mg Aerosil 200 and 388 mg Poloxamer 188.

Each of the above compositions were added to a size 0, white gelatin capsule.

The uniformity of 10 capsules containing 40 mg VB-201 was determined according to Chapter 2.9.40 of the European Pharmacopoeia.

The 10 individual capsules contained 105.3%, 102.8%, 103.1%, 106.5%, 102.1%, 107.9%, 102.2%, 103.0%, 106.1% and 102.0%, of the target amount of VB-201. The mean VB-201 content was 104.08% of the target amount (RSD=2.05%; L1 value=7.71).

These results indicate high uniformity of the prepared capsules.

Example 12

Encapsulation of VB-201 with Poloxamer 188, Talc and a Thixotropic Agent

VB-201 was encapsulated using poloxamer 188 as a thermosoftening carrier, talc as an anti-adherent agent, and Aerosil® fumed silica as a thixotropic agent, as described in Example 11, except that reduced amounts of talc and Aerosil 200 were used. Capsules containing 40 mg, 60 mg or 80 mg VB-201 were prepared from a mix containing talc and VB-201 in a weight ratio of talc:VB-201 of about 1:4 in a mixture of molten Poloxamer 188 with about 1% of Aerosil® 200 fumed silica.

Example 14

Encapsulation of Oxidized Phospholipids with Poloxamer 188, Talc and a Thixotropic Agent Other compounds structurally related to VB-201 may be formulated as described herein for VB-201. Exemplary compounds that can be formulated according to the present disclosure are described in international patent application publication WO2010/052718, the disclosure of which is incorporated herein by reference in its entirety. For example, the following compounds can be encapsulated using the procedures and formulations described in Examples 10-13 by replacing VB-201 with one or more of these compounds. For example, each of the below analogs can be encapsulated using poloxamer 188 as a thermosoftening carrier, talc as an anti-adherent agent, and Aerosil® fumed silica as a thixotropic agent, e.g., as described in Examples 11 and 12:

1-hexadecyl-2-(4'-methylcarboxybutyl)-glycero-3-phosphoethanolamine;

1-hexadecyl-2-(4'-methylcarboxybutyl)-glycero-3-phosphocholine (VB-208);

1-hexadecyl-2-(4'-carboxybutyl)-glycero-3-phosphoethanolamine (VB-202);

1-hexadecyl-2-(3'-carboxypropyl)-glycero-3-phosphoethanolamine (VB-206);

1-hexadecyl-2-(3'-carboxypropyl)-glycero-3-phosphocholine (VB-205);

1-hexadecyl-2-(6'-carboxyhexanyl)-glycero-3-phosphocholine (VB-203);

1-dodecyl-2-(4'-carboxybutyl)-glycero-3-phosphocholine (VB-209);

1-hexadecyl-2-(4'-carboxybutyl)-glycero-3-phosphoethanolamine-N-glutaric acid (VB-210);

1-(15'-carboxypentadecyl)-2-(4'-carboxybutyl)-glycero-3-phosphocholine (VB-213);

1-(15'-carboxypentadecyl)-2-(4'-carboxybutyl)-glycero-3-phosphoethanolamine (VB-214);

1-octadecyl-2-(4'-carboxybutyl)-glycero-3-phosphocholine (VB-215);

1-octadecyl-2-(4'-carboxybutyl)-glycero-3-phosphoethanolamine (VB-216);

1-hexadecyl-2-(2'-carboxyethyl)-glycero-3-phosphocholine (VB-217);

1-S-hexadecyl-2-(4'-carboxybutyl)-glycero-3-phosphocholine (1-S-VB-201);

1-S-hexadecyl-2-(4'-carboxybutyl)-glycero-3-phosphoethanolamine (1-S-VB-202);

1-(cis-9-hexadecenyl)-2-(4'-carboxybutyl)-glycero-3-phosphocholine;

1-octyl-2-(4'-carboxybutyl)-glycero-3-phosphocholine (VB-207);

1-octyl-2-(4'-carboxybutyl)-glycero-3-phosphoethanolamine;

1-eicosanyl-2-(4'-carboxybutyl)-glycero-3-phosphocholine (VB-219);

1-eicosanyl-2-(4'-carboxybutyl)-glycero-3-phosphoethanolamine (VB-220);

1-(2'-octyl)dodecyl-2-(4'-carboxybutyl)-glycero-3-phosphocholine (VB-221);

1-(2'-octyl)dodecyl-2-(4'-carboxybutyl)-glycero-3-phosphoethanolamine (VB-222); and 1-hexadecyl-2-(4'-carboxybutyl)-glycero-3-phosphoserine (VB-223).

Example 15

Pharmacokinetic (PK) Data of VB-201 from Formulations 10 and 4

Pharmacokinetic studies were performed using two different VB-201 formulations (formulation 10 of Example 13 and formulation 4 of Example 11). Single oral doses of mg VB-201 were administered to 26 human subjects for each formulation, and the VB-201 plasma concentrations were measured for a period of 144 hours after dosing for each subject.

Figure 9:
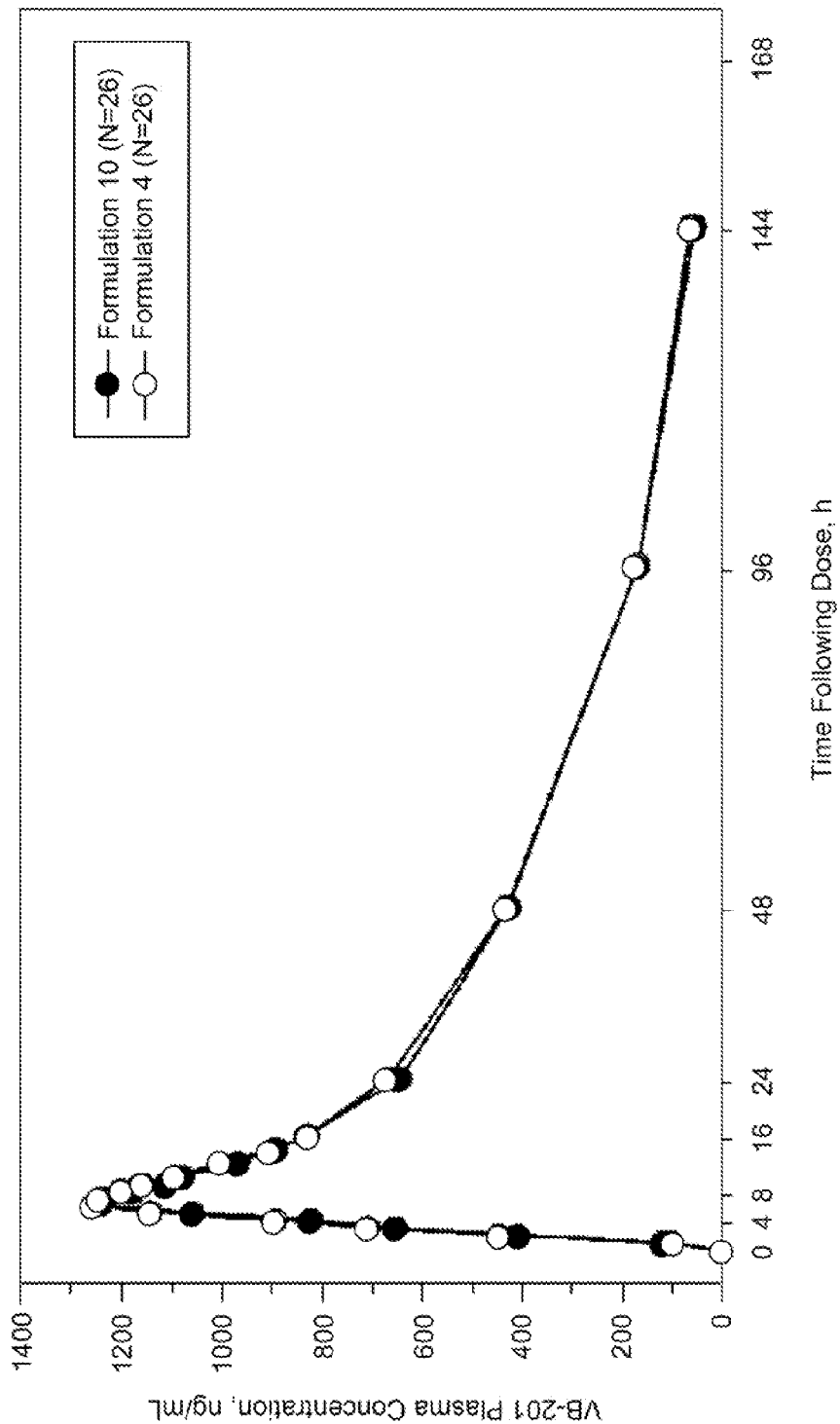
FIG. 9 is a graph showing the plasma concentrations (ng/mL) of VB-201 following a single 40 mg oral dose of VB-201 administered as formulation 10 of Example 13 and formulation 4 of Example 11 to human subjects.

As shown in FIG. 9, the mean plasma concentrations of VB-201, following administration of formulation 10 and formulation 4 to human subjects peaked at similar times (median $T_{max}$: 6-6.5 h) and at similar concentrations (mean $C_{max}$: 1,290-1,298 ng/mL). In the postabsorption/post-distribution phase, plasma concentrations of VB-201 declined in a similar mono-exponential fashion (not explicitly shown in FIG. 9). The mean terminal half-lives ($t_{1/2}$) after administration of both formulations were about 37 hours. VB-201 plasma concentrations were above the assay limit of quantification for at least 96 hours in all subjects.

Overall, the plasma pharmacokinetics resulting from administration of either formulation were remarkably similar in magnitude and in inter-subject variability of the calculated parameter. The relative bioavailability Fr ($AUC_\infty$ ratio of formulation 4 to formulation 10) and the $C_{max}$ ratio of formulation 4 relative to formulation 10 were 103% and 102%, respectively, and both of these PK parameter ratios exhibited similar intersubject variabilities (i.e., 16-20%). Results of statistical evaluations for bioequivalency for 40-mg, single, oral doses of VB-201, when administered as formulation 10 and formulation 4 are shown in Table 8 below:

TABLE 8

Summary of the 90% confidence intervals (CI) for the geometric mean ratio of VB-201 $C_{max}$ and AUC parameters

| Parameter | Formulation 10 (N = 26) | | | Formulation 4 (N = 26) | | |
|---|---|---|---|---|---|---|
| | Mean | SD | CV % | Mean | SD | CV % |
| $C_{max}$, ng/mL | 1289.74 | 232.25 | 18.01 | 1298.08 | 230.97 | 17.79 |
| $T_{max}^a$, h | 6.00 | (5.00-10.00) | NA | 6.50 | (5.00-9.00) | NA |
| $AUC_T$, ng · h/mL | 53200 | 12500 | 23.5 | 55000 | 13900 | 25.3 |
| $AUC_\infty$, ng · h/mL | 57500 | 12000 | 20.8 | 58900 | 14500 | 24.6 |
| CL/F, L/h | 0.725 | 0.154 | 21.3 | 0.725 | 0.205 | 28.3 |
| $\lambda_z$, l/h | 0.0185 | 0.00246 | 13.3 | 0.0186 | 0.00303 | 16.2 |
| $t_{1/2}^b$, h | 37.4 | 4.98 | 13.3 | 37.2 | 6.07 | 16.3 |
| Rsq | 0.997 | 0.00267 | 0.268 | 0.997 | 0.00515 | 0.517 |
| Fr, % | NA | NA | NA | 103 | 16.6 | 16.2 |
| $C_{max}$ Ratio, % | NA | NA | NA | 102 | 20.6 | 20.1 |

[a]Expressed as median and range.
[b]Expressed as harmonic mean and pseudo standard deviation based on jackknife variance.
NA = Not Applicable.

Table 9 presents results of statistical evaluations for bioequivalency between the formulation 4 and formulation 10 after 40-mg, single, oral doses of VB-201. For $C_{max}$, $AUC_T$, and $AUC_\infty$, the 90% confidence limits for the geometric mean ratios were within the acceptable bioequivalence range of 80% to 125%, indicating that formulation 4 is bioequivalent to Formulation 10. The statistical power of each of these three separate analyses was greater than 99%.

TABLE 9

Summary of the 90% Confidence Intervals (CI) for the Geometric Mean Ratio (GMR) of VB-201 $C_{max}$ and AUC Parameters

| Parameter | Formulation | Geometric Least Squares Mean | GMR[a] | 90% CI for GMR Lower | 90% CI for GMR Upper | p-value[b] | Power[c] |
|---|---|---|---|---|---|---|---|
| $C_{max}$, ng/mL | 10 | 1270.56 | | | | | |
| | 4 | 1275.14 | 100.36 | 94.01 | 107.14 | 0.926 | >99.9 |
| $AUC_T$, | 10 | 51700 | | | | | |
| | 4 | 53000 | 102.58 | 96.87 | 108.62 | 0.454 | >99.9 |
| $AUC_\infty$, | 10 | 56300 | | | | | |
| | 4 | 56900 | 101.01 | 95.66 | 106.66 | 0.754 | >99.9 |

[a]Geometric Mean Ratio of Formulation 4 (test) and Formulation 10 (reference); expressed as a percent.
[b]p-value for testing difference in natural log-transformed parameter between Formulation B (test) and Formulation A (reference).
[c]Expressed as a percent.

Statistical tests for differences between Formulations 10 and 4 were also performed for $T_{max}$ (using the Wilcoxon signed rank test) and for the terminal rate constant ($\lambda_z$, using the paired t-test). There were no formulation-related statistical differences in either of these PK parameters as shown in Table 10 below.

TABLE 10

Statistical Comparison of VB-201 Terminal Rate Constant ($\lambda_z$) and Time to Maximum Observed Plasma Concentration ($T_{max}$)

| Parameter | N | Formulation | Arithmetic Mean ($\lambda_z$) or Median ($T_{max}$) | SD ($\lambda_z$) or Range ($T_{max}$) | p-value[a] |
|---|---|---|---|---|---|
| $\lambda_z$, 1/h | 26 | 10 | 0.0185 | 0.00246 | 0.835 |
| | 26 | 4 | 0.0186 | 0.00303 | |
| $T_{max}$, h | 26 | 10 | 6.00 | 5.00-10.00 | 0.747 |
| | 26 | 4 | 6.50 | 5.00-9.00 | |

[a]Statistical inference between treatments.

Note:
$\lambda_z$ was statistically evaluated by a paired t-test and $T_{max}$ was statistically evaluated by the Wilcoxon signed rank test with significance set at ≤0.05 for both.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A pharmaceutical composition comprising an oxidized phospholipid having a structure according to Formula (1):

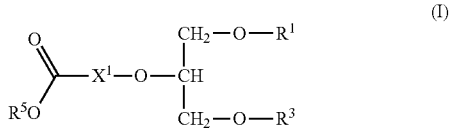

wherein
R[1] is $C_{14}$-$C_{20}$ straight or branched alkyl;
R[3] is selected from the group consisting of phosphorylethanolamine, phosphorylcholine, phosphorylethanolamine-N-glutaric acid, and phosphorylserine;
R[5] is selected from the group consisting of H, a negative charge, methyl, and ethyl; and
X[1] is $C_4$ or $C_5$ alkylene,
the composition further comprising a thermosoftening carrier and an anti-adherent agent, wherein said thermosoftening carrier has a melting point from about 40° C. to about 100° C., wherein the weight ratio of said anti-adherent agent to said oxidized phospholipid is about 1:5 to about 5:1, wherein said thermosoftening carrier is a poloxamer or a polyethylene glycol, and wherein said anti-adherent agent is selected from the group consisting of talc, magnesium stearate, cellulose, cellulose derivatives, lactose, gelatin, alginates, aluminum hydroxide, magnesium oxide, clays, attapulgite, bentonite, carrageenan, copovidone, hectorite, polymethacrylates, sodium docusate, erythritol, povidones, croscarmellose sodium, dextrates, starches, iron oxide, kaolin, silicates, corn flour, sugars, calcium carbonate, magnesium carbonate, calcium phosphate, calcium sulfate, bicarbonates, citrate salts, and titanium dioxide.

2. The pharmaceutical composition of claim 1, wherein said thermosoftening carrier is a poloxamer.

3. The pharmaceutical composition of claim 2, wherein said poloxamer is poloxamer 188.

4. The pharmaceutical composition of claim 1, wherein said thermosoftening carrier is a polyethylene glycol.

5. The pharmaceutical composition of claim 1, wherein said anti-adherent agent is talc.

6. The pharmaceutical composition of claim 1, further comprising a thixotropic agent.

7. The pharmaceutical composition of claim 6, wherein said thixotropic agent is selected from the group consisting of fumed silica, kieselguhr, gums, cellulose derivatives, starches, polymers, emulsifiers, and clay derivatives, attapulgite, mica, synthetic magnesium phyllosilicates, layered silicates, modified smectites, hectorite, and sepiolite.

8. The pharmaceutical composition of claim 7, wherein said thixotropic agent is a fumed silica.

9. The pharmaceutical composition of claim 6, wherein the concentration of said thixotropic agent, relative to the combined weight of said thermosoftening carrier and said thixotropic agent, is from about 0.25 weight percent to about 10 weight percent.

10. The pharmaceutical composition of claim 1, wherein said pharmaceutical composition is a liquid-fill composition.

11. The pharmaceutical composition of claim 1, wherein the oxidized phospholipid is 1-hexadecyl-2-(4'-carboxybutyl)-glycero-3-phosphocholine (VB-201).

12. A process for producing a pharmaceutical composition comprising an oxidized phospholipid having a structure according to Formula (I):

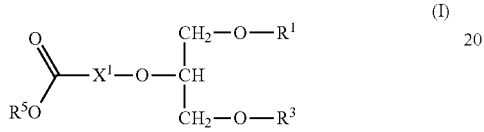

wherein $R^1$ is $C_{14}$-$C_{20}$ straight or branched alkyl;

$R^3$ is selected from the group consiting of phosphorylethanolamine, phosphorylcholine, phosphorylethanolamine-N-glutaric acid, and phosphorylserine;

$R^5$ is selected from the group consisting of H, a negative charge, methyl, and ethyl; and $X^1$ is $C_4$ or $C_5$ alkylene, a thermosoftening carrier, and an anti-adherent agent, wherein said thermosoftening carrier has a melting point from about 40° C. to about 100° C., wherein the weight ratio of said anti-adherent agent to said oxidized phospholipid is about 1:5 to about 5:1 wherein said thermosoftening carrier is a poloxamer or a polyethylene glycol, andwherein said anti-adherent agent is selected from the group consisting of talc, magnesium stearate, cellulose, cellulose derivatives, lactose, gelatin, alginates, aluminum hydroxide, magnesium oxide, clays, attapulgite, bentonite, carrageenan, copovidone, hectorite, polymethacrylates, sodium docusate, erythritol, povidones, croscarmellose sodium, dextrates, starches, iron oxide, kaolin, silicates, corn flour, sugars, calcium carbonate, magnesium carbonate, calcium phosphate, calcium sulfate, bicarbonates, citrate salts, and titanium dioxide, the process comprising heating said thermosoftening carrier to a temperature above the melting point of said thermosoftening carrier, milling the oxidized phospholipid with the anti-adherent agent, and contacting the oxidized phospholipid and the anti-adherent agent with the thermosoftening carrier, to thereby obtain said pharmaceutical composition.

13. A liquid-fill capsule comprising an oxidized phospholipid having a structure according to Formula (I):

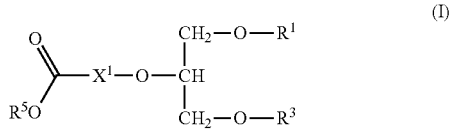

wherein $R^1$ is $C_{14}$-$C_{20}$ straight or branched alkyl;

$R^3$ is selected from the group consisting of phosphorylethanolamine, phosphorylcholine, phosphorylethanolamine-N-glutaric acid, and phosphorylserine;

$R^5$ is selected from the group consisting of H, a negative charge, methyl, and ethyl; and $X^1$ is $C_4$ or $C_5$ alkylene, the liquid-fill capsule further comprising a solid or semi-solid matrix, said matrix comprising a thermosoftening carrier and an anti-adherent agent, wherein said thermosoftening carrier has a melting point from about 40° C. to about 100° C., wherein the weight ratio of said anti-adherent agent to said oxidized phospholipid is about 1:5 to about 5:1 wherein said thermosoftening carrier is a poloxamer or a polyethylene glycol, andwherein said anti-adherent agent is selected from the group consisting of talc, magnesium stearate, cellulose, cellulose derivatives, lactose, gelatin, alginates, aluminum hydroxide, magnesium oxide, clays, attapulgite, bentonite, carrageenan, copovidone, hectorite, polymethacrylates, sodium docusate, erythritol, povidones, croscarmellose sodium, dextrates, starches, iron oxide, kaolin, silicates, corn flour, sugars, calcium carbonate, magnesium carbonate, calcium phosphate, calcium sulfate, bicarbonates, citrate salts, and titanium dioxide.

14. The capsule of claim 13, wherein said thermosoftening carrier is a poloxamer.

15. The capsule of claim 14, wherein said poloxamer is poloxamer 188.

16. The capsule of claim 13, wherein said thermosoftening carrier is a polyethylene glycol.

17. The capsule of claim 13, wherein said anti-adherent agent is talc.

18. The capsule of claim 13, wherein said matrix further comprises a thixotropic agent.

19. The capsule of claim 18, wherein said thixotropic agent is selected from the group consisting of a fumed silica, kieselguhr, gums, cellulose derivatives, starches, polymers, emulsifiers, and clay derivatives, attapulgite, mica, synthetic magnesium phyllosilicates, layered silicates, modified smectites, hectorite, and sepiolite.

20. The capsule of claim 19, wherein said thixotropic agent is a fumed silica.

21. The capsule of claim 18, wherein the concentration of said thixotropic agent, relative to the combined weight of said thermosoftening carrier and said thixotropic agent, is from about 0.25 weight percent to about 10 weight percent.

22. The capsule of claim 13, wherein said oxidized phospholipid is 1-hexadecyl-2-(4'-carboxybutyl)-glycero-3-phosphocholine (VB-201).

23. The capsule of claim 22, comprising from about 20 mg to about 80 mg VB-201.

24. A liquid-fill capsule comprising:
a thermosoftening carrier;
VB-201 from about 1 mg to about 100 mg;
an anti-adherent agent at a weight ratio from about 1:5 to 5:1 (anti-adherent agent:VB-201); and
a thixotropic agent at a concentration relative to the combined weight of said thermosoftening carrier and said thixotropic agent from about 0.25 weight percent to about 10 weight percent, wherein said thermosoftening carrier is a poloxamer or a polyethylene glycol, andwherein said anti-adherent agent is selected from the group consisting of talc, magnesium stearate, cellulose, cellulose derivatives, lactose, gelatin, alginates, aluminum hydroxide, magnesium oxide, clays, attapulgite, bentonite, carrageenan, copovidone, hectorite, polymethacrylates, sodium docusate, erythritol, povidones, croscarmellose sodium, dextrates, starches, iron oxide, kaolin, silicates, corn flour, sugars, calcium carbonate, magnesium carbonate, calcium phosphate, calcium sulfate, bicarbonates, citrate salts, and titanium dioxide.

25. The liquid-fill capsule of claim 13 comprising:
40 mg VB-201;
10 mg of an anti-adherent agent;
4 mg of a thixotropic agent; and
396 mg of a thermosoftening agent.

26. The liquid-fill capsule of claim 25 comprising:
40 mg VB-201;
10 mg talc;
4 mg fumed silicon dioxide; and
396 mg of poloxamer 188.

27. A method of treating an inflammatory disease or disorder, the method comprising administering to a subject in need thereof a pharmaceutically effective amount of the pharmaceutical composition of claim 1.

28. The pharmaceutical formulation of claim 24, wherein the formulation, when orally administered to a human subject at a single oral dose of about 40 mg of VB-201, provides a mean maximum plasma concentration ($C_{max}$) of VB-201 from about 1,000 ng/mL to about 1,600 ng/mL, and a median time to mean maximum plasma concentration ($T_{max}$) of VB-201 from about 5 hours to about 10 hours.

29. The pharmaceutical formulation of claim 28, wherein the formulation, when orally administered to a human subject at a single oral dose of about 40 mg of VB-201, provides a plasma concentration time curve with a mean area under the curve ($AUC_{\infty}$), ranging from about 45,000 to about 70,000 ng h/mL, and a mean half-live ($t\frac{1}{2}$) between about 32 and about 42 hours.

30. The pharmaceutical composition of claim 1, wherein the weight ratio of said anti-adherent agent to said oxidized phospholipid is about 1:4.

31. The liquid fill capsule of claim 13, wherein the weight ratio of said anti-adherent agent to said oxidized phospholipid is about 1:4.

32. The liquid-fill capsule of claim 13 comprising:
40 mg VB-201;
40 mg of an anti-adherent agent;
12 mg of a thixotropic agent; and
388 mg of a thermosoftening carrier.

33. The liquid-fill capsule of claim 32 comprising:
40 mg VB-201;
40 mg talc;
12 mg of fumed silicon dioxide; and
388 mg of a poloxamer 188.

34. The liquid-fill capsule of claim 13 comprising:
80 mg VB-201;
80 mg of an anti-adherent agent;
12 mg of a thixotropic agent; and
388 mg of a thermosoftening carrier.

35. The liquid-fill capsule of claim 34 comprising:
80 mg VB-201;
80 mg talc;
12 mg fumed silicon dioxide; and
388 mg of poloxamer 188.

36. The liquid-fill capsule of claim 13 comprising:
80 mg VB-201;
20 mg of an anti-adherent agent;
4 mg of a thixotropic agent; and
396 mg of a thermosoftening agent.

37. The liquid-fill capsule of claim 36 comprising:
80 mg VB-201;
20 mg talc;
4 mg fumed silicon dioxide; and
396 mg of poloxamer 188.

* * * * *